US009993545B2

(12) United States Patent
Weiner et al.

(10) Patent No.: US 9,993,545 B2
(45) Date of Patent: Jun. 12, 2018

(54) FOOT AND MOUTH DISEASE VIRUS (FMDV) CONSENSUS PROTEINS, CODING SEQUENCES THEREFOR AND VACCINES MADE THEREFROM

(71) Applicants: The Trustees of the University of Pennsylvania, Philadelphia, PA (US); Inovio Pharmaceuticals, Inc., Blue Bell, PA (US); David B. Weiner, Merion, PA (US); Jian Yan, Havertown, PA (US); Karuppiah Muthumani, Cherry Hill, NJ (US); Niranjan Y. Sardesai, Blue Bell, PA (US)

(72) Inventors: David B. Weiner, Merion, PA (US); Jian Yan, Wallingford, PA (US); Karuppiah Muthumani, Cherry Hill, NJ (US); Niranjan Y. Sardesai, Blue Bell, PA (US)

(73) Assignees: THE TRUSTEES OF THE UNIVERSITY OF PENNSYLVANIA, Philadelphia, PA (US); INOVIO PHARMACEUTICALS, INC., Plymouth Meeting, PA (US)

( * ) Notice: Subject to any disclaimer, the term of this patent is extended or adjusted under 35 U.S.C. 154(b) by 62 days.

(21) Appl. No.: 14/774,356

(22) PCT Filed: Mar. 17, 2014

(86) PCT No.: PCT/US2014/030809

§ 371 (c)(1),
(2) Date: Sep. 10, 2015

(87) PCT Pub. No.: WO2014/145951

PCT Pub. Date: Sep. 18, 2014

(65) Prior Publication Data

US 2016/0045589 A1 Feb. 18, 2016

Related U.S. Application Data

(60) Provisional application No. 61/794,197, filed on Mar. 15, 2013, provisional application No. 61/802,225, filed on Mar. 15, 2013.

(51) Int. Cl.

| | |
|---|---|
| ***C12N 7/00*** | (2006.01) |
| ***A61K 39/135*** | (2006.01) |
| ***A61K 39/12*** | (2006.01) |
| ***C07K 14/005*** | (2006.01) |
| *A61K 39/00* | (2006.01) |

(52) U.S. Cl.

CPC ............ *A61K 39/135* (2013.01); *A61K 39/12* (2013.01); *C07K 14/005* (2013.01); *C12N 7/00* (2013.01); *A61K 2039/53* (2013.01); *A61K 2039/552* (2013.01); *C12N 2770/32134* (2013.01)

(58) Field of Classification Search

None

See application file for complete search history.

(56) References Cited

U.S. PATENT DOCUMENTS

| | | | |
|---|---|---|---|
| 4,510,245 | A | 4/1985 | Cousens et al. |
| 4,722,848 | A | 2/1988 | Paoletti et al. |
| 4,790,987 | A | 12/1988 | Compans et al. |
| 4,797,368 | A | 1/1989 | Carter et al. |
| 4,920,209 | A | 4/1990 | Davis et al. |
| 5,017,487 | A | 5/1991 | Stunnenberg et al. |
| 5,077,044 | A | 12/1991 | Stocker |
| 5,110,587 | A | 5/1992 | Paoletti et al. |
| 5,112,749 | A | 5/1992 | Brey, III et al. |
| 5,174,993 | A | 12/1992 | Paoletti |
| 5,223,424 | A | 6/1993 | Cochran et al. |
| 5,225,336 | A | 7/1993 | Paoletti |
| 5,240,703 | A | 8/1993 | Cochran |
| 5,242,829 | A | 9/1993 | Panicali |
| 5,273,525 | A | 12/1993 | Hofmann |
| 5,294,441 | A | 3/1994 | Curtiss, III et al. |
| 5,294,548 | A | 3/1994 | McLinden et al. |
| 5,310,668 | A | 5/1994 | Ellis et al. |
| 5,387,744 | A | 2/1995 | Curtiss, III et al. |
| 5,389,368 | A | 2/1995 | Gurtiss, III |

(Continued)

FOREIGN PATENT DOCUMENTS

| | | |
|---|---|---|
| CN | 1737144 | 2/2006 |
| CN | 101070348 | 11/2007 |

(Continued)

OTHER PUBLICATIONS

Subramanian et al. Development of foot-and-mouth disease virus (FMDV) serotype O virus-like-particles (VLPs) vaccine and evaluation of its potency. Antiviral Res. Dec. 2012;96(3):288-95.*

Ramanathan et al. Coimmunization with an optimized IL15 plasmid adjuvant enhances humoral immunity via stimulating B cells induced by genetically engineered DNA vaccines expressing consensus JEV and WNV E DIII. Vaccine. Jul. 9, 2009;27(32):4370-80.*

Robertson et al. Nucleotide and amino acid sequence coding for polypeptides of foot-and-mouth disease virus type A12. J Virol. Jun. 1985;54(3):651-60.*

Baker et al., Protein Structure Predication and Structural Genomics, Science (2001) vol. 294, No. 5540, pp. 93-96.*

(Continued)

*Primary Examiner* — Michelle S Horning

(74) *Attorney, Agent, or Firm* — Riverside Law LLP

(57) ABSTRACT

The present invention relates to synthetic, consensus foot-and-mouth disease virus (FMDV) immunogenic proteins and nucleic acid molecule encoding such proteins, to vaccines against FMDV, to methods for inducing immune responses against FMVD, to methods for distinguishing between individuals infected with FMDV versus those vaccinated against FMDV, and methods of prophylactically and/or therapeutically immunizing individuals against FMDV.

10 Claims, 17 Drawing Sheets

(56) References Cited

U.S. PATENT DOCUMENTS

| | | | |
|---|---|---|---|
| 5,424,065 A | 6/1995 | Curtiss, III et al. | |
| 5,451,499 A | 9/1995 | Cochran | |
| 5,453,364 A | 9/1995 | Paoletti | |
| 5,462,734 A | 10/1995 | Letchworth, III et al. | |
| 5,470,734 A | 11/1995 | Sondermeijer et al. | |
| 5,474,935 A | 12/1995 | Chatterjee et al. | |
| 5,482,713 A | 1/1996 | Paoletti | |
| 5,580,859 A | 12/1996 | Feigner et al. | |
| 5,591,439 A | 1/1997 | Plotkin et al. | |
| 5,593,972 A | 1/1997 | Weiner et al. | |
| 5,643,579 A | 7/1997 | Hung et al. | |
| 5,650,309 A | 7/1997 | Wong-Staal et al. | |
| 5,676,594 A | 10/1997 | Joosten | |
| 5,698,202 A | 12/1997 | Ertl et al. | |
| 5,703,055 A | 12/1997 | Feigner et al. | |
| 5,739,118 A | 4/1998 | Carrano et al. | |
| 5,817,637 A | 10/1998 | Weiner et al. | |
| 5,830,876 A | 11/1998 | Weiner et al. | |
| 5,955,088 A | 9/1999 | Ghiasi et al. | |
| 5,962,428 A | 10/1999 | Carrano et al. | |
| 5,981,505 A | 11/1999 | Weiner et al. | |
| 6,034,298 A | 3/2000 | Lam et al. | |
| 6,042,836 A | 3/2000 | Berman et al. | |
| 6,110,161 A | 8/2000 | Mathiesen et al. | |
| 6,156,319 A | 12/2000 | Cohen et al. | |
| 6,261,281 B1 | 7/2001 | Mathiesen et al. | |
| 6,589,529 B1 | 7/2003 | Choi et al. | |
| 6,697,669 B2 | 2/2004 | Dev et al. | |
| 6,939,862 B2 | 9/2005 | Bureau et al. | |
| 6,958,060 B2 | 10/2005 | Mathiesen et al. | |
| 7,238,522 B2 | 7/2007 | Hebel et al. | |
| 7,245,963 B2 | 7/2007 | Draghia-Akli et al. | |
| 7,328,064 B2 | 2/2008 | Mathiesen et al. | |
| 8,409,588 B2 * | 4/2013 | Czub | C12N 7/00 424/204.1 |
| 2004/0001864 A1 | 1/2004 | King et al. | |
| 2004/0265955 A1 | 12/2004 | Fang et al. | |
| 2005/0052630 A1 | 3/2005 | Smith et al. | |
| 2005/0182005 A1 | 8/2005 | Tuschi et al. | |
| 2005/0287672 A1 | 12/2005 | Nordgren et al. | |
| 2006/0251677 A1 | 11/2006 | Bachmann et al. | |
| 2011/0236416 A1 | 9/2011 | Audonnet et al. | |
| 2012/0282217 A1 | 11/2012 | Weiner et al. | |

FOREIGN PATENT DOCUMENTS

| | | | |
|---|---|---|---|
| CN | 101121938 | 2/2008 | |
| CN | 101270155 | 9/2008 | |
| EP | 1632247 | 3/2006 | |
| WO | 1994/016737 | 8/1994 | |
| WO | 1999/66954 | 12/1999 | |
| WO | 2006063445 | 6/2006 | |
| WO | 2008/116368 | 10/2008 | |
| WO | 09/73330 | 6/2009 | |
| WO | 2011/054011 | 5/2011 | |
| WO | WO 2011112945 * | 9/2011 | A61K 39/135 |
| WO | 2012/032348 | 3/2012 | |

OTHER PUBLICATIONS

Attwood, T. The Babel of Bioinformatics, Science (2000) vol. 290, No. 5491, pp. 471-473.*

Kiyota et al. Genetic analysis of the VP4/VP2 coding region in human rhinovirus species C in patients with acute respiratory infectionin Japan. J Med Microbiol. Apr. 2013;62(Pt 4):610-7. Abs Only.*

GenBank: AY593816.1 (2005) FMDV.*

GenBank: AY593767.1 (2005) FMDV.*

GenBank: JF721437.1 (2011) FMDV.*

GenBank: AY593782.1 (2005) FMDV.*

Carrillo et al., "Comparative genomics of foot-and-mouth disease virus", Journal of Virology, 2005, 79(10):6487-6504.

Cooke, J. et al., "Serotype-specific differences in antigenic regions of foot-and-mouth disease virus (FMDV): a comprehensive statistical analysis", Infect Genet Evol. 2008, 8(6): 855-863.

Wang, C. et al., "Effective synthetic peptide vaccine for foot-and-mouth disease in swine", Vaccine. 2002, 20 (19-20):2603-10.

Mohapatra, J.K. et al., "Comparative genomics of serotype Asia 1 foot-and-mouth disease virus isolates from India sampled over the last decades", Virus Research, 2008, 136:16-29.

Cottam, E.M. et al., "Molecular Epidemiology of the Foot-and-Mouth Diease Viurs Outbreak in the United Kingdom in 2001", Journal of Virology, 2006, 80:11274-11282.

Martinez, M. et al., "Two mechanisms of antigenic diversification of foot-and-mouth disease virus", Virology.1991, 184(2):695-706.

Tosh et al., Phylogenetic analysis of serotype A foot-and-mouth disease virus isolated in India between 1977 and 2000, 2002, Archives of Virology, 147:493-513.

Kumar et al., Immunogenicity testing of novel engineered HIV-1 envelope Gp140 DNA vaccine construct, 2006, DNA and Cell Biology, 25(7):383-392.

GenBank Accession No. CAB62583, 2005; http://www.ncbi.nlm.nih.gov/protein/CAB62583.1.

Nagarajan et al., "Self replicating gene vaccine carrying P1-2A gene of FMDV serotype and its effects on the immune reponse of cattle", Indian J.Virol, 22(1): 50-58, 2011.

Fowler et al., "A DNA vaccination regime including protein boost and electroporation protects cattle against foot-and-mouth disease", Antiviral Research, 94(1): 25-34, 2012.

Li et al., "Dramatic improvement in FMD DNA vaccine efficacy and cross-serotype antibody induction in pigs following a protein boost", J Vaccine, 26(21): 2647-2656, 2008.

Du et al., "Immune responses of two recombinant adenoviruses expressing VP1 antigens of FMDV fused with porcine granulocyte macrophage colony-stimulating factor", Vaccine, 25(49): 8209-8219, 2007.

Cheung et al., "Comparison of the major antigen determinants of different serotypes of foot-and-mouth disease virus", J Virol, 48(2): 451-459, 1983.

Nagendrakumar et al., "Genetic analysis of foot-and-mouth disease virus serotype A of Indian origin and detection of positive selection and recombination in leader protease-and capsid-coding regions", Journal of Biosciences, 34(1): 85-101, 2009.

GenBank Accession No. EF185303, dated Jan. 15, 2007; https://www.ncbi.nlm.nih.gov/nuccore/EF185303.

GenBank Accession No. EF120387, dated Dec. 12, 2006; https://www.ncbi.nlm.nih.gov/nuccore/EF120387.

GenBank Accession No. EF120388, dated Dec. 12, 2006; https://www.ncbi.nlm.nih.gov/nuccore/EF120388.

GenBank Accession No. EF120389, dated Dec. 12, 2006; https://www.ncbi.nlm.nih.gov/nuccore/EF120389.

GenBank Accession No. EF120395, dated Dec. 12, 2006; https://www.ncbi.nlm.nih.gov/nuccore/EF120395.

GenBank Accession No. EF120396, dated Dec. 12, 2006; https://www.ncbi.nlm.nih.gov/nuccore/EF120396.

GenBank Accession No. EF120397, dated Dec. 12, 2006; https://www.ncbi.nlm.nih.gov/nuccore/EF120397.

Robertson B H et al, "Nucleotide and Amino-Acid Sequence Coding for Polypeptides of Foot-and-Mouth Disease Virus Type A-12", Journal of Virology, 1985, 54(3):651-660.

Ramanathan et al., "Coimmunization with an optimized IL 15 plasmid adjuvant enhances humoral immunity via stimulating B cells induced by genetically engineered DNA vaccines expressing consensus JEV and WNV E DIII," Vaccine, 2009, 27(32):4370-4380.

Subramanian et al., "Development of foot-and-mouth disease virus (FMDV) subtype O virus-like particles (VLPs) vaccine and evlauation of its potency," 2012, Antiviral Res. 96(3):288-95.

* cited by examiner

FMDV-As1-Shamir89

DNA gel analysis and Amino acid Sequence

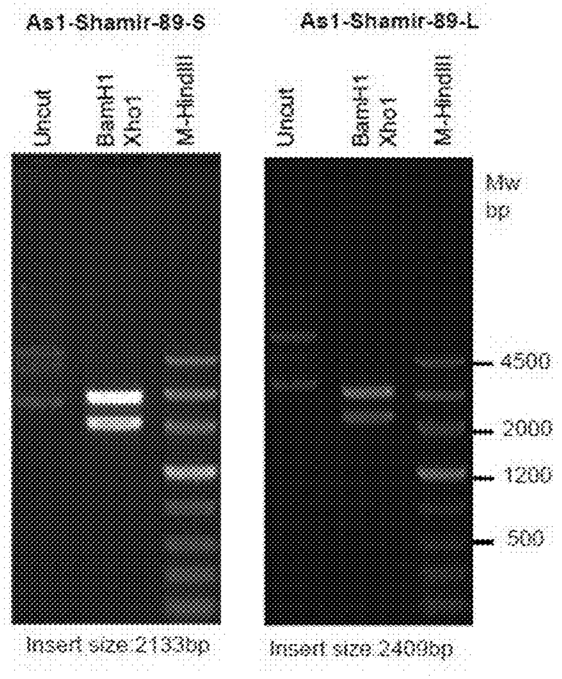

Long form AA sequence

MDWTWILFLVAAATRVHSGAGQSSPATGSQNQSGNTGSIINNYYMQQYQNSMDTQLGDN
AISGGSNEGSTDTTSTHTNNTQNNDWFSRLASSAFSGLFGALLArgrkrrsDKKTEETTLL
EDRILTTRNGHTTSTTQSSVGVTYGYAVAEDAVSGPNTSGLETRVQQAERFFKKHLFDW
TPNLAFGHCYYLELPTEHKGVYGSLMGSYAYMRNGWDIEVTAVGNQFNGGCLLVALVPE
LKELDTRQKYQLTLFPHQFINPRTNMTAHINVPYVGINRYDQYALHKPWTLVVMVVAPL
TVKTGGSEQIKVYMNAAPTYVHVAGELPSKErgrkrrsGIVPVACADGYGNMVTTDPKTAD
PVYGKVFNPPRTNLPGRFTNFLDVAEACPTFLRFGEVPFVKTVNSGDRLLAKFDVSLAA
GHMSNTYLAGLAQYYTQYSGTMNVHFMFTGPTDAKARYMVAYVPPGMTPPTDPEHAAHC
IHSEWDTGLNSKFTFSIPYLSAADYAYTASDVAETTSVQGWVCIYQITHGKAEGDALVV
SVSAGKDFEFRLPVDARQQrgrkrrsTTTTGESADPVTTTVENYGGETQTARRLHTDVAFI
LDRFVKLTAPKNIQTLDLMQIPSHTLVGALLRSATYYFSDLEVALVHTGPVTWVPNGAP
KDALNNQTNPTAYQKQPITRLALPYTAPHRVLATVYNGKTAYGETTSRRGDMAALAQRL
SARLPTSFNYGAVKADTITELLIRMKRAETYCPRPLLALDTTQDRRKQEIIAPEKQVLrg
rkrrsNFDLLKLAGDVESNPG-Stop

Note: Blue = VP4- missing in short form

FIG. 2

FMDV-A24cruzeiro

DNA gel analysis and Amino acid Sequence

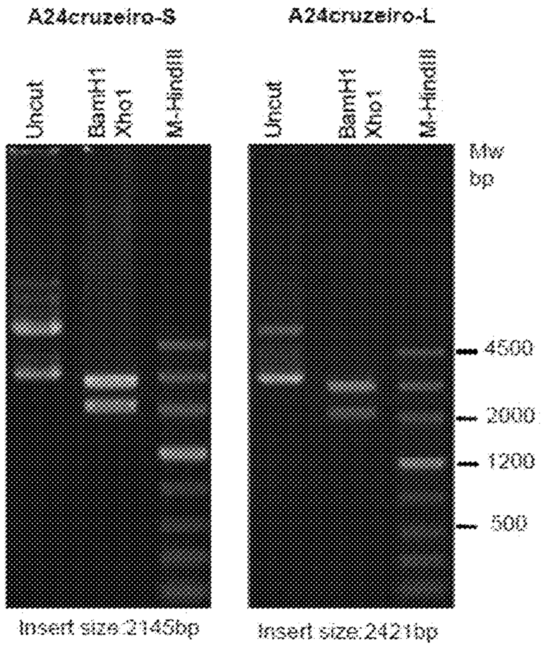

Long form AA sequence

MDWTWILFLVAAATRVHSGAGQSSPATGSQNQSGNTGSIINNYYMQQYQNSMDTQLGDN
AISGGSNEGSTDTTSTHTTNTQNNDWFSKLASSAFTGLFGALLArgrkrrsDKKTEETTLL
EDRILTTRNGHTTSTTQSSVGVTHGYSTEEDHVAGPNTSGLETRVVQAERFYKKYLFDW
TTDKAFGHLEKLELPSDHHGVFGHLVDSYAYMRNGWDVEVSAVGNQFNGGCLLVAMVPE
WKEFDTREKYQLTLFPHQFISPRTNMTAHITVPYLGVNRYDQYKKHKPWTLVVMVVSPL
TVNNTSAAQIKVYANIAPTYVHVAGELPSKErgrkrrsGIFPVACADGYGGLVTTDPKTAD
PAYGKVYNPPRTNYPGRFTNLLDVAEACPTFLCFDDGKPYVVTRTDDTRLLAKFDLSLA
AKHMSNTYLSGIAQYYTQYSGTINLHFMFTGSTDSKARYMVAYIPPGVETPPDTPERAA
HCIHAEWDTGLNSKFTFSIPYVSAADYAYTASDTAETINVQGWVCIYQITHGKAENDTL
VVSVSAGKDFELRLPIDPRQQrgrkrrsTTATGESADPVTTTVENYGGETQIQRRHHTDIG
FIMDRFVKIQSLSPTHVIDLMQTHQHGLVGALLRAATYYFSDLEIVVRHEGNLTWVPNG
APESALLNTSNPTAYNKAPFTRLALPYTAPHRVLATVYNGTSKYAVGGSGRRGDMGSLA
ARVVKQLPASFNYGAIKADAIHELLVRMKRAELYCPRPLLAIEVSSQDRHKQKIIAPAK
QLLrgrkrrsNFDLLKLAGDVESNPG-stop Note: Blue = VP4- missing in short form

FIG. 4

Cellular immune responses elicited by FMDV-As1-Shamir89 vaccines

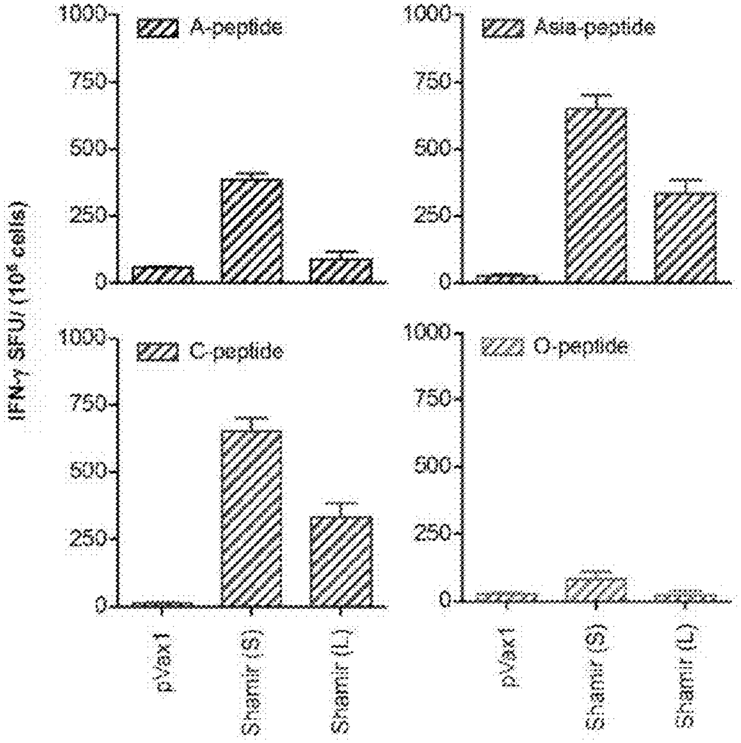

FMDV-As1-Shamir89-Long
Leader pep-VP4-VP2-VP3-VP1-2A

FMDV-As1-Shamir89-Short
Leader pep-VP2-VP3-VP1-2A

Groups of BalbC mice (n# 4/group) were immunized i.m. at week 0, 2 and week 4 with 25ug FMDV- DNA vaccine.

Subtype A, Asia, C and O-specific CD8+ T-lymphocyte responses were assessed by IFN-γ ELISpot assays to a pool of overlapping VP1 peptides.

Mean responses in all groups one week after the third immunization. Error bars indicate standard errors.

Combined FMDV- As1-Shamir 89-VPs immunization induced significant differences in cell-mediated immune responses and strongly react with Subtype A, Asia and C peptides

FIG. 10

Cellular immune responses elicited by FMDV-Sat2 vaccines

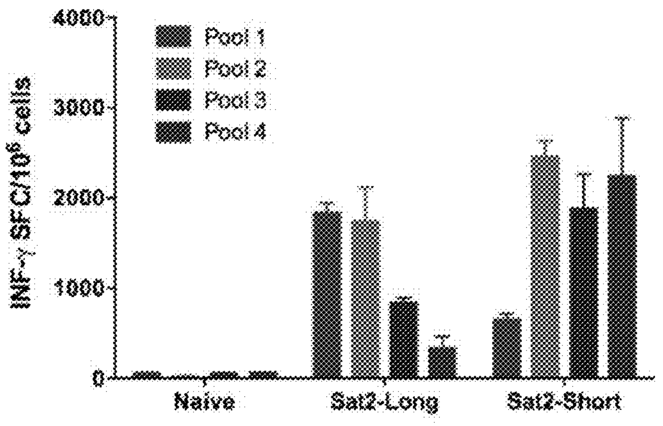

FMDV-As1-Sat2-Long
Leader pep-VP4-VP2-VP3-VP1-2A

FMDV-As1-Sat2-Short
Leader pep-VP2-VP3-VP1-2A

Groups of BalbC mice (n# 4/group) were immunized i.m. at week 0, 2 and week 4 with 25ug FMDV- DNA vaccine.

Subtype FMDV-Sat2 specific CD8" T-lymphocyte responses were assessed by IFN-γ ELISpot assays to a pool of overlapping entire vaccine peptides.

Mean responses in all groups one week after the third immunization. Error bars indicate standard errors.

Combined FMDV- Sat2-VPs immunization induced significant differences in cell-mediated immune responses and strongly react with Subtype Sat-2 peptides

FIG. 11

Abs binding (Total IgG)

FMDV – Immune Reagent Study

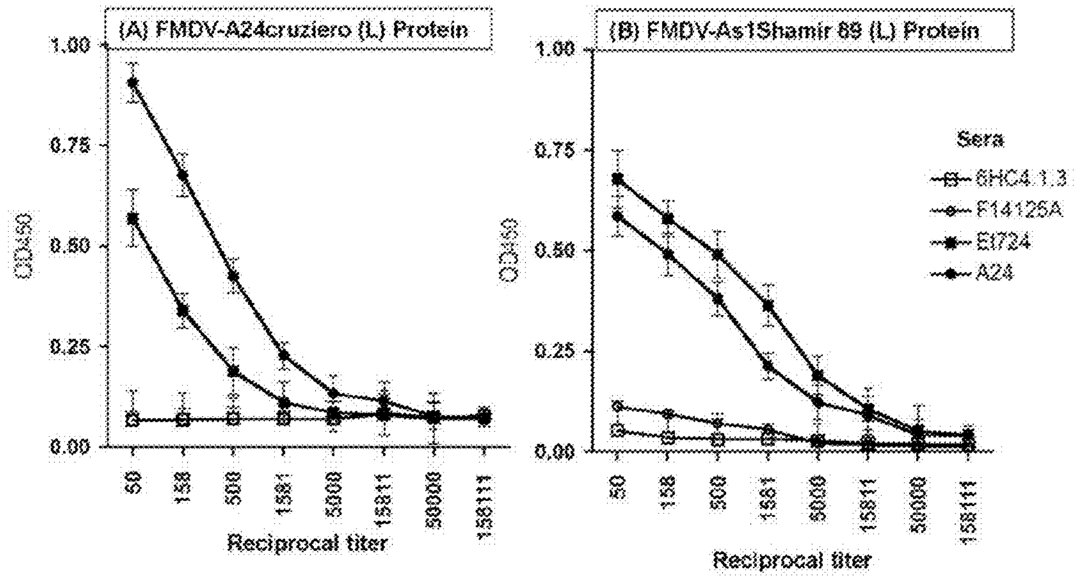

Abs binding by ELISA analysis. Protein lysates were prepared from (A) FMDV-A24crusoero (L) (B) FMDV-As1Shamir89 (L) transfected cells. 100ug of protein lysate was used to coat the plate. Wells were probed with the specific antibodies/sera at dilution indicated and levels of binding were determined by ELISA. Each data point is the average absorbance from triplicate wells.

FIG.14

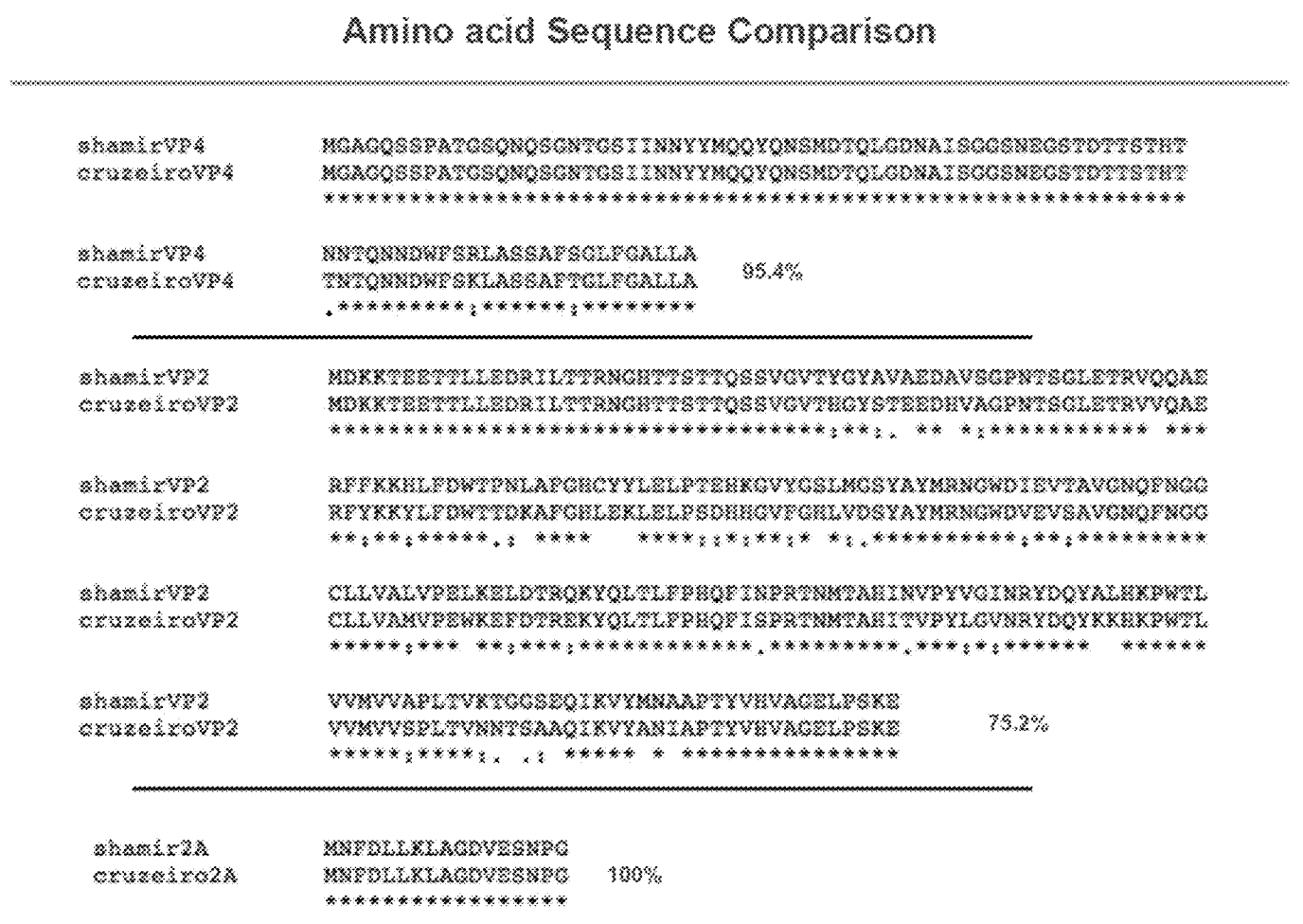

Amino acid Sequence Comparison

```
shamirVP4      MGAGQSSPATGSQNQSGNTGSIINNYYMQQYQNSMDTQLGDNAISGGSNEGSTDTTSTHT
cruzeiroVP4    MGAGQSSPATGSQNQSGNTGSIINNYYMQQYQNSMDTQLGDNAISGGSNEGSTDTTSTHT
               ************************************************************

shamirVP4      NNTQNNDWFSRLASSAFSGLFGALLA
cruzeiroVP4    TNTQNNDWFSKLASSAFTGLFGALLA     95.4%
               .*********:******:********
```

```
shamirVP2      MDKKTEETTLLEDRILTTRNGHTTSTTQSSVGVTYGYAVAEDAVSGPNTSGLETRVQQAE
cruzeiroVP2    MDKKTEETTLLEDRILTTRNGHTTSTTQSSVGVTHGYSTEEDHVAGPNTSGLETRVVQAE
               **********************************:**:. ** *:*********** ***

shamirVP2      RFFKKHLFDWTPNLAFGHCYYLELPTEHKGVYGSLMGSYAYMRNGWDIEVTAVGNQFNGG
cruzeiroVP2    RFYKKYLFDWTTDKAFGHLEKLELPSDHHGVFGHLVDSYAYMRNGWDVEVSAVGNQFNGG
               **:**:*****.: ****    ****::*:**:* *:.**********:**:*********

shamirVP2      CLLVALVPELKELDTRQKYQLTLFPHQFINPRTNMTAHINVPYVGINRYDQYALHKPWTL
cruzeiroVP2    CLLVAMVPEWKEFDTREKYQLTLFPHQFISPRTNMTAHITVPYLGVNRYDQYKKHKPWTL
               *****:*** **:***:************.*********.***:*:******  ******

shamirVP2      VVMVVAPLTVKTGGSEQIKVYMNAAPTYVHVAGELPSKE
cruzeiroVP2    VVMVVSPLTVNNTSAAQIKVYANIAPTYVHVAGELPSKE     75.2%
               *****:****:.  .: ***** * ***************
```

```
shamir2A       MNFDLLKLAGDVESNPG
cruzeiro2A     MNFDLLKLAGDVESNPG   100%
               *****************
```

FIG. 15

FOOT AND MOUTH DISEASE VIRUS (FMDV) CONSENSUS PROTEINS, CODING SEQUENCES THEREFOR AND VACCINES MADE THEREFROM

CROSS-REFERENCE TO RELATED APPLICATIONS

This application is the U.S. national stage application filed under 35 U.S.C. § 371 claiming benefit to International Patent Application No. PCT/US14/030809, filed Mar. 17, 2014, which is entitled to priority under 35 U.S.C. § 119(e) to U.S. Provisional Application Nos. 61/794,197, filed Mar. 15, 2013 and 61/802,225, filed Mar. 15, 2013, each of which is hereby incorporated by reference in its entirety.

FIELD OF THE INVENTION

The present invention relates to synthetic, consensus foot-and-mouth disease virus (FMDV) immunogenic proteins and nucleic acid molecule encoding such proteins, to vaccines against FMDV, to methods for inducing immune responses against FMVD, to methods for distinguishing between individuals infected with FMDV versus those vaccinated against FMDV, and methods of prophylactically and/or therapeutically immunizing individuals against FMDV.

BACKGROUND OF THE INVENTION

Foot-and-mouth disease (FMD) is a highly contagious disease of domestic and wild cloven-hoofed animals including cattle, swine, goats and deer which rapidly replicates in the host and spreads to in-contact susceptible animals. The disease is characterized by fever, lameness, and vesicular lesions of the tongue, feet, snout, and teats resulting in high morbidity, but low mortality in adult animals. FMDV infection drives an acute vesicular disease in cattle, buffaloes, sheep, goats and pigs, which may develop into persistent infection (excluding pigs). FMDV can infect many other mammalian species, including antelopes, elephants, hedgehogs, among others. It is though that the original FMDV natural host might be the African buffalo since: i) it is persistently infected and ii) disease is rarely observed.

The causative agent of FMD is the foot-and-mouth disease virus (FMDV), a Group IV (+) ssRNA virus of the Aphthovirus genus, of the Picornaviridae family. FMDV occurs in seven major serotypes: O, A, C, SAT-1, SAT-2, SAT-3, and Asia-1. These serotypes are regionally restricted with the O serotype most common world-wide. The single-stranded, positive-sense RNA genome of FMDV is approximately 8500 bases surrounded by an icosahedral capsid with 60 copies each of four structural proteins VP1-VP4. The viral proteins are antigenically highly variable within its several subtypes including A, Asia 1, O, C, SAT1, SAT2, and SAT3.

FMD is economically devastating and infection of cloven-hoofed livestock can result in significant losses. Recent outbreaks have resulted in billions of dollars lost. Outbreaks have recently occurred in a number of previously disease free countries including Taiwan in 1997, United Kingdom and Netherlands in 2001, and the emergence in several South American countries has risen the awareness of the economically destructive virus. Furthermore, there is worldwide concern that a possible economic terrorist attack employing FMDV to target countries with large livestock industries, such as the US $100 billion/year livestock industry.

Previous measures to control FMDV include slaughter of the infected or in-contact animals and decontamination. Countries that slaughter their livestock due to a FMDV outbreak can only resume livestock activities if the countries have FMDV free status for 3 months after the last outbreak. Countries usually use vaccination of the animals to treat an FMDV outbreak as a last resort because countries that have vaccinated and do not slaughter the animals must wait an entire year to regain FMD free status. Countries, however, are looking to vaccinate their animals before any FMDV outbreak and would be able to retain their FMD free status.

In the past, FMDV vaccines included chemically inactivated whole virus antigen in conjunction with an adjuvant; however, there are disadvantages to this because it requires expensive high-containment manufacturing facilities to produce the vaccine. Over the past 25-30 years investigators have been trying to develop a vaccine that provides protection after a single inoculation. These efforts include the use of VP1 purified from virus particles, bioengineered VP1, VP1 peptides, chemically synthesized VP1 peptides, live vectors expressing VP1 epitopes, inoculation with DNA encoding VP1 epitopes, and using the full capsid protein VP1-VP4 produced from FMDV-infected cultures or delivery of the VP1-VP4 capsid via replication defective human adenovirus type 5 (Ad5) vector. All of these approaches present only a limited number of epitopes across all the subtypes of the FMDV viruses to the inoculated animal.

Accordingly, there is a need in the art for a vaccine and methods of diagnosing FMDV infected mammals that is suitable to provide protection against a plurality of epitopes of FMDV across the various subtypes of FDMV.

SUMMARY OF THE INVENTION

Nucleic acid molecule comprising sequences encoding viral protein VP4 linked at its C terminus to a protease cleavage site linked at its C terminus to viral protein VP2 linked at its C terminus to a protease cleavage site linked at its C terminus to viral protein VP3 linked at its C terminus to a protease cleavage site linked to viral protein VP1 at its C terminus to a protease cleavage site linked to viral protein 2A are disclosed. The nucleic acid molecule may further comprise a nucleic acid sequence that encodes a leader sequence at the 5' end of coding sequence for viral protein VP4. In some embodiments, the coding sequence for viral protein VP4 is omitted. In some embodiments, the coding sequence for viral protein 2A is omitted. In some embodiments, the coding sequence that encodes the N terminal leader sequence is omitted. In some embodiments, the coding sequence that encodes the N terminal leader sequence is an Ig leader sequence such as an IgG or IgE leader sequence. In some embodiments the cleavage site is recognized by furin.

Plasmids comprising the nucleic acid molecules are provided including plasmids in which the viral proteins are from an FMDV subtype selected from the group consisting of A, Asia1, C, O, SAT1, SAT2 and SAT3. The vaccine comprising four plasmids wherein the viral proteins encoding be nucleic acid sequence are from each FMDV subtype of the group consisting of A, Asia1, C, and O are provided. In some embodiments, vaccines comprising seven plasmids wherein the viral proteins encoding be nucleic acid sequence from each FMDV subtype of the group consisting of A, Asia1, C, O, SAT1, SAT2 and SAT3 are also provided. In some embodiments, vaccines comprising fewer than seven, i.e. one, two, three, four, five or six plasmids are provided in which the viral proteins encoding be nucleic acid sequence from FMDV subtypes selected from the group consisting of A, Asia1, C, O, SAT1, SAT2 and SAT3.

Nucleic acid molecule comprising sequences encoding viral protein VP4 linked at its C terminus to sequences encoding a protease cleavage site linked at its C terminus to sequences encoding viral protein VP2 linked at its C terminus to sequences encoding a protease cleavage site linked at its C terminus to sequences encoding viral protein VP3 linked at its C terminus to sequences encoding a protease cleavage site linked to sequences encoding viral protein VP1 linked at its C terminus to sequences encoding viral protein 2A are disclosed herein are referred to long versions or "long". Nucleic acid molecule comprising sequences encoding viral protein VP2 linked at its C terminus to sequences encoding a protease cleavage site linked at its C terminus to sequences encoding viral protein VP3 linked at its C terminus to sequences encoding a protease cleavage site linked to sequences encoding viral protein VP1 linked at its C terminus to sequences encoding viral protein 2A are disclosed herein are referred to short versions or "short". In both long and short versions, coding sequence for the protease cleavage site that linked to the 3' end of the coding sequence encoding viral protein VP1 and coding sequence for viral protein 2A linked may be omitted. In both long and short versions, coding sequence for an N terminal leader sequence is linked the N terminal of the coding sequence for viral protein VP4 in the case of a long version and the coding sequence for viral protein VP2 in the case of the long sequence. The N terminal leader is preferable an Ig leader such as an IgG or an IgE signal sequence. In some embodiments the cleavage site is recognized by furin.

In some embodiments, plasmids comprising the nucleic acid molecules are provided including plasmids in which the viral proteins are from an FMDV subtype selected from the group consisting of A, Asia1, C, O, SAT1, SAT2 and SAT3. In some embodiments, the vaccine comprising four plasmids wherein the viral proteins encoding be nucleic acid sequence are from each FMDV subtype of the group consisting of A, Asia1, C, and O are provided. In some embodiments, vaccines comprising seven plasmids wherein the viral proteins encoding be nucleic acid sequence from each FMDV subtype of the group consisting of A, Asia1, C, O, SAT1, SAT2 and SAT3 are also provided.

Methods of generating an immune response against FMDV in an individual by administering to the individual one of the disclosed vaccines are provided.

Methods of preventing infection be FMDV in an individual by administering to the individual one of the disclosed vaccines are provided.

Provided herein is an isolated nucleic acid comprising a sequence encoding the consensus amino acid sequence of at least VP1-VP3, and preferably, VP1-VP4 of foot-and-mouth disease virus that elicits a cross-reactive immune response in a vaccinated subject against multiple subtypes of FMD, including A, Asia 1, C, O, SAT1, SAT2, SAT3, SAT4. The nucleic acid may comprise a sequence selected from the group consisting of (a) a construct derived from FMDV-A24cruzeiro comprising a nucleotide sequence set forth in SEQ ID NO: 1 encoding VP-4-VP2-VP3-VP1 (long) as set forth in SEQ ID NO:2; (b) a construct derived from FMDV-A24cruzeiro comprising a nucleotide sequence set forth in SEQ ID NO: 3 encoding VP2-VP3-VP1 (short) as set forth in SEQ ID NO:4; (c) a construct derived from FMDV-As1-Shamir89 comprising a nucleotide sequence set forth in SEQ ID NO: 5 encoding VP-4-VP2-VP3-VP1 (long) as set forth in SEQ ID NO:6; (d) a construct derived from FMDV-As1-Shamir89 comprising a nucleotide sequence set forth in SEQ ID NO: 7 encoding VP2-VP3-VP1 (short) as set forth in SEQ ID NO:8; (e) a construct derived from FMDV-SAT2 comprising a nucleotide sequence set forth in SEQ ID NO: 9 encoding VP-4-VP2-VP3-VP1 (long) as set forth in SEQ ID NO:10; (f) a construct derived from FMDV-STA2 comprising a nucleotide sequence set forth in SEQ ID NO: 11 encoding VP2-VP3-VP1 (short) as set forth in SEQ ID NO:12;

Provided herein are nucleic acid molecules such as those selected from the group consisting of: a) an FMDV-A24cruzeiro derived modified nucleotide sequence such as that set forth in SEQ ID NO: 1 (FMDV-A24cruzeiro-long) inserted into a plasmid such as pVAX having the sequence set forth in SEQ ID NO:13; b) an FMDV-A24cruzeiro derived modified nucleotide sequence such as that set forth in SEQ ID NO: 3 (FMDV-A24cruzeiro-short) inserted into a plasmid such as pVAX having the sequence set forth in SEQ ID NO:14; c) an FMDV-As1-Shamir89 derived modified nucleotide sequence such as that set forth in SEQ ID NO: 5 (FMDV-As1-Shamir89-long) inserted into a plasmid such as pVAX having the sequence set forth in SEQ ID NO:15; and d) an FMDV-As1-Shamir89 derived modified nucleotide sequence such as that set forth in SEQ ID NO: 7 (FMDV-As1-Shamir89-long) inserted into a plasmid such as pVAX having the sequence set forth in SEQ ID NO:16.

Nucleic acid molecules in compositions may comprise the following nucleic acid sequences, and/or fragments thereof, and/or homologous sequences to the sequences, and/or fragments of such homologous sequences; the nucleic acid sequence being: a) a nucleic acid sequences derived from FMDV-As1-Shamir89 that encodes VP4 such as that set forth in SEQ ID NO: 17; b) a nucleic acid sequences derived from FMDV-A24cruzeiro that encodes VP4 such as that set forth in SEQ ID NO: 18; c) a nucleic acid sequences derived from FMDV-As1-Shamir89 that encodes VP2 such as that set forth in SEQ ID NO: 19; d) a nucleic acid sequences derived from FMDV-A24cruzeiro that encodes VP2 such as that set forth in SEQ ID NO: 20; e) a nucleic acid sequences derived from FMDV-As1-Shamir89 that encodes 2A such as that set forth in SEQ ID NO: 21; f) a nucleic acid sequences derived from FMDV-A24cruzeiro that encodes 2A such as that set forth in SEQ ID NO: 22; g) a nucleic acid sequences derived from FMDV-As1-Shamir89 that encodes VP3 such as that set forth in SEQ ID NO: 23; h) a nucleic acid sequences derived from FMDV-A24cruzeiro that encodes VP3 such as that set forth in SEQ ID NO: 24; i) a nucleic acid sequences derived from FMDV-As1-Shamir89 that encodes VP1 such as that set forth in SEQ ID NO: 25; j) a nucleic acid sequences derived from FMDV-A24cruzeiro that encodes VP2 such as that set forth in SEQ ID NO: 26.

The amino acid sequence of the cleavage site recognized by the protease furin is sequence forth in SEQ ID NO:27.

In some embodiments, constructs may include a C3 consensus coding sequence (SEQ ID NO:28) which encodes a C3 protease consensus protein (SEQ ID NO:29).

Also provided herein is a vaccine capable of generating in a mammal an immune response against a plurality of foot-and-mouth disease virus (FMDV) subtypes where the vaccine comprises a DNA plasmid comprising a promoter operably linked to a coding sequence that encodes a consensus FMDV antigen comprising capsid proteins VP1-VP4 from one or more FMDV subtypes and a pharmaceutically acceptable excipient wherein the DNA plasmid is capable of expressing the consensus FMDV antigen in a cell of the mammal in a quantity effective to elicit a broad cross reactive immune response in the mammal. The vaccine may generate an immune response against FMDV subtypes A, Asia 1, C, O, SAT1, SAT2, SAT3 or combinations thereof.

Also provided herein is a vaccine capable of generating in a mammal an immune response against a plurality of foot-and-mouth disease virus (FMDV) subtypes where the vaccine comprises one or more DNA plasmids comprising a promoter operatively linked to a coding sequence that encodes a consensus FMDV antigen comprising capsid proteins VP1-VP4 from one or more FMDV subtypes selected from the group consisting of subtypes A, Asia 1, C, O, SAT1, SAT2, SAT3, or a combination thereof and a pharmaceutically acceptable excipient thereof wherein the DNA plasmids are capable of expressing a consensus FMDV antigen in a cell of the mammal in a quantity effective to elicit an immune response in the mammal. The vaccine may be administered to a mammal such as swine, ruminant, human or a primate. The vaccine may elicit an immune response in a mammal such as a humoral, cellular, or both a humoral and cellular response.

Also provided herein is a vaccine capable of generating in a mammal an immune response against a plurality of FDMV subtypes where the vaccine comprises an antigen comprising one or more consensus amino acid sequences encoding capsid proteins VP1-VP4 of foot-and-mouth-disease virus (FMDV) subtypes A, Asia 1, C, O, SAT1, SAT2, or SAT3 and a pharmaceutically acceptable excipient thereof. The pharmaceutically acceptable excipient may be an adjuvant selected from the group consisting of IL-2 and IL-15. The pharmaceutically acceptable excipient of the vaccine may be transfection facilitating agent. The transfection facilitating agent may be a polyanion, polycation or a lipid such as poly-L-glutamate at a concentration of less than 6 mg/ml. The vaccine may be administered to a mammal such as a swine, ruminant, human or primate. The vaccine may elicit an immune response in a mammal such as a humoral, cellular, or both a humoral and cellular response.

Also provided herein is a method for eliciting an immune response against a plurality of FMDV virus subtypes in a mammal comprising delivering the DNA plasmid vaccine described herein to the tissue of the mammal and electroporating cells of the tissue with a pulse of energy at a constant current effective to permit entry of the DNA plasmid into the cells. The delivery of the DNA plasmid vaccines described herein may be accomplished by a method may comprise injecting the DNA plasmid vaccine into the intradermic, subcutaneous, or muscle tissue. The DNA plasmid of the method may be delivered by presetting the current and the pulse of energy is at a constant current that equals the present current. The electroporation step of the method may further comprise measuring the impedance in the electroporated cells, adjusting the energy level of the pulse of energy relative to the measured impedance to maintain a constant current in the electroporated cells wherein the measuring and adjusting step occurs within a lifetime of the pulse of energy. The electroporating step may further comprise delivering the pulse of energy to a plurality of electrodes according to a pulse sequence pattern that delivers the pulse of energy in a decentralized pattern.

Also provided is a method of diagnosing a mammals infected with FMDV wherein the method comprises isolating a fluid sample from the mammal, isolating antibodies from the fluid sample of the mammal, and comparing the antibodies isolated with a control mammal that has been inoculated with the vaccine described herein, wherein the control mammal only has antibodies to FMDV VP1-VP4 proteins and the infected FMDV mammal has antibodies to FMDV VP1-V4 proteins and FMDV nonstructural proteins. The nonstructural proteins may be FMDV 2C, 3A, and 3D polymerase.

Methods of eliciting an immune response against one or more FMDV virus subtypes in a mammal are provided. The methods comprising using a vaccine disclosed here and, in some embodiments, may include the steps of administering a nucleic acid molecule encoding a protein having FMDV immunogenic sequence to the tissue of the mammal; and electroporating cells of the tissue with a pulse of energy at a constant current effective to permit entry of the DNA plasmid into the cells.

A method of diagnosing a mammals infected with FMDV in mammal vaccinated according to processes disclosed herein are also provided. The methods comprise isolating a fluid sample from the vaccinated mammal and detecting the presence of FMDV proteins not included in said vaccine and/or antibodies against FMDV proteins not included in said vaccine. The presence of such FMDV proteins and/or antibodies against such FMDV proteins indicates the vaccinated mammal has been infected with FMDV.

BRIEF DESCRIPTION OF DRAWINGS

FIG. 2 shows a pair of stained gels showing cloning of As1-Shamir89-S (left—SEQ ID NO:7) and As1-Shamir89-L (right-SEQ ID NO:5) and the amino acid sequence for FMDV-As1-Shamir89-L long form (SEQ ID NO:6 is a FMDV-As1-Shamir89-L long form sequence). The sequence included the IgE leader sequence at the N terminus shaded, the proteolytic cleavage sites in lower case and the VP4 sequences in bold type between the IgE leader and first proteolytic cleavage site. The VP1 sequence is shown in bold type between the third and fourth proteolytic cleavage site and a 2a sequence between the last (fourth) proteolytic cleavage site and stop.

FIG. 4 shows a pair of stained gels showing cloning of A24cruzeiro-S (left—SEQ ID NO:3) and A24cruzeiro-L (right—SEQ ID NO:1) and the amino acid sequence for FMDV-A24cruzeiro-L long form (SEQ ID NO:2 is a FMDV-A24cruzeiro-L long form sequence). The sequence included the IgE leader sequence at the N terminus shaded, the proteolytic cleavage sites in lower case and the VP4 sequences is shown between the IgE leader and first proteolytic cleavage site. The VP1 sequence shown between the third and fourth proteolytic cleavage site and a 2a sequence between the last (fourth) proteolytic cleavage site and stop.

FIG. 10 shows data of cellular immune responses elicited by FMDV-As1-Sharma89-L and FMDV-As1-Sharma89-S vaccines.

FIG. 11 shows data of cellular immune responses elicited by FMDV-Sat2-L and FMDV-Sat2-S vaccines.

FIG. 14 shows data of ELISA analysis of antibody binding using protein lysates prepared from FMDV-A24cruzeiro-L transfected cells and FMDV-As1-Sharma89-L transfected cells.

FIG. 15 shows amino acid sequence comparisons between sharir and cruzeiro sequences. Shamir VP4 sequences (SEQ ID NO:17) are shown compared cruzeiro VP4 sequences (SEQ ID NO:18); Shamir VP2 sequences (SEQ ID NO:19) are shown compared cruzeiro VP2 sequences (SEQ ID NO:20); and Shamir 2A sequences (SEQ ID NO:21) are shown compared cruzeiro 2A (SEQ ID NO:22).

DETAILED DESCRIPTION

Figure 1:
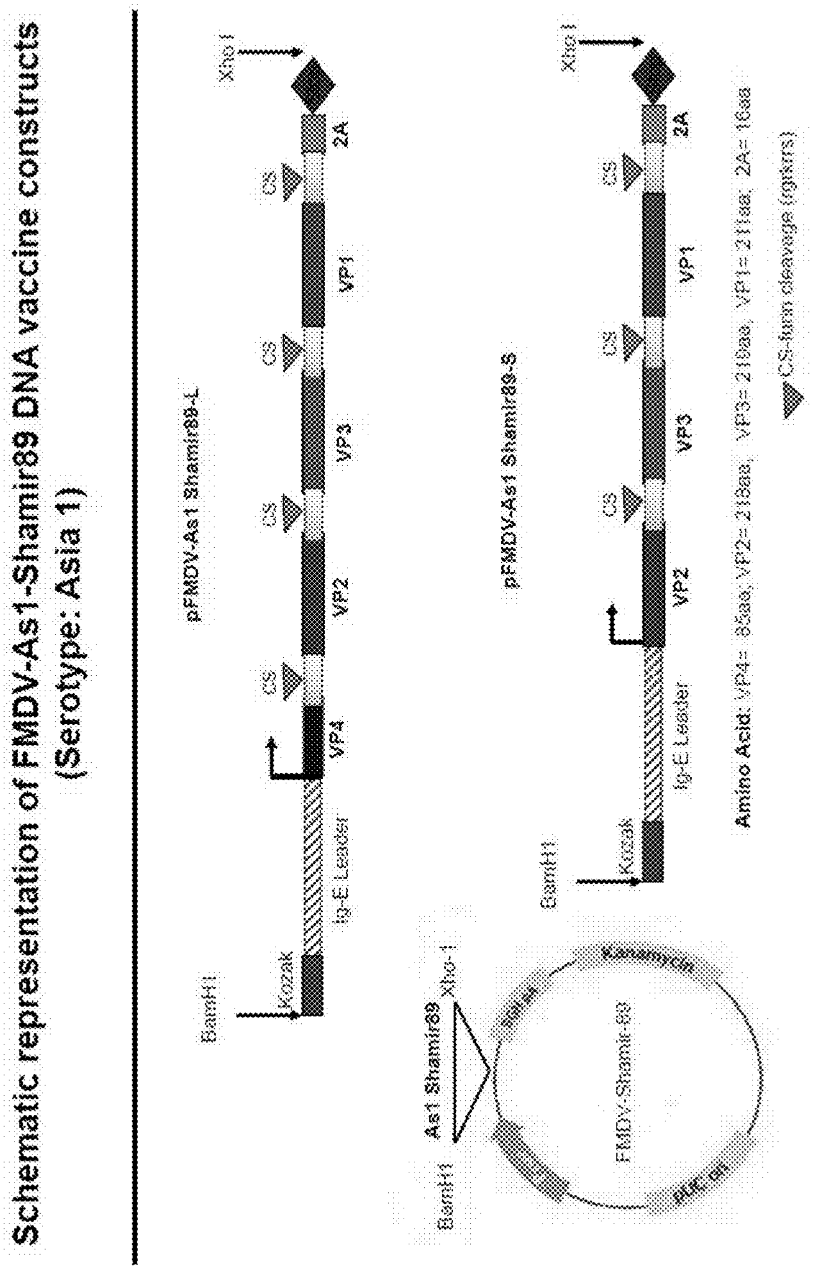
FIG. 1 shows schematic representation of a FMDV-As1-Shamir-89 DNA vaccine constructs for Serotype Asia 1, indicating that an As1 Shamir89 insert is clones into a BamH1 and Xho-1 sites. A plasmid map is based upon the plasmid pVAX. Examples of the FMDV-As1-Shamir insert may be the long form, which is shown in FIG. 1 as pFMDV-As1 Shamir-89-L or the short form, which is shown in FIG. 1 as pFMDV-As1 Shamir-89-S.

Consensus amino acid sequences have been generated for fusion proteins comprising multiple FMDV proteins and individual FMDV proteins from various serotypes. Nucleic acid molecules encoding the proteins have also been generated In one aspect of the present invention, there are fusion proteins comprising FMDV proteins VP1, VP2, VP3, VP4 and/or 2A and/or 3C and nucleic acid sequences encoding these proteins, which can be generated and used in a vaccine to provide protection of mammals against foot-and-mouth disease across one or more subtypes of FMDV, including A, Asia 1, O, C, SAT1, SAT2, and SAT3. Preferably, the VP1 gene is a consensus for a selected subtype of FMDV, e.g., described herein is a FMDV-Sat2 wherein the VP1 is a Sat2 consensus VP1.

While not being bound by scientific theory, a vaccine directed against the consensus amino acid sequences of VP1, VP2, VP3, and/or VP4 for one or more subtypes of FMDV will present a large repertoire of epitopes that are effective in eliciting an effective immune response (either humoral, cellular or both) against a majority of the species within each subtype of FMDV. While not being bound by scientific theory, VP1 is an excellent immunogenic target for a vaccine directed against the consensus amino acid sequences of VP1. VP1 is a predominant immunogen.

Constructs of some embodiments include a long form and a short form. Constructs of some embodiments provide viral proteins VP1, VP2, VP3, and VP4 in a specific order: VP4-VP2-VP3-VP1. An optional tail, 2A is also provided. The constructs have an optional IgE leader sequence. When expressed, a proteolytic cleavage site "CS" is provided between each of VP4, VP2, VP3, VP1 and when present 2A. The protease which can process the site may be furin in some embodiments or a FMDV protease in some embodiments. Other protease sites may be used. The site must be recognized by a protease commonly found in cells where the vaccine is expressed.

In one aspect of the present invention, there are fusion proteins comprising consensus FMDV proteins VP1, VP2, VP3, VP4 and/or 2A and/or 3C and nucleic acid sequences encoding these proteins, which can be generated and used in a vaccine to provide protection of mammals against foot-and-mouth disease across one or more subtypes of FMDV, including A, Asia 1, O, C, SAT1, SAT2, and SAT3.

In another aspect of the present invention, there are fusion proteins comprising consensus FMDV proteins VP1 and nucleic acid sequences encoding these proteins, from two different subtypes which can be generated and used in a vaccine to provide protection of mammals against foot-and-mouth disease across one or more subtypes of FMDV, including A, Asia 1, O, C, SAT1, SAT2, and SAT3.

In another aspect of the present invention, there are consensus FMDV proteins VP1 and nucleic acid sequences encoding them which can be generated and used in a vaccine to provide protection of mammals against foot-and-mouth disease across one or more subtypes of FMDV, including A, Asia 1, O, C, SAT1, SAT2, and SAT3.

1. Definitions

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

a. Adjuvant

"Adjuvant" as used herein may mean any molecule added to the DNA plasmid vaccines described herein to enhance antigenicity of the foot-and-mouth disease virus (FMDV) antigen encoded by the DNA plasmids and encoding nucleic acid sequences described hereinafter.

b. Antibody

"Antibody" may mean an antibody of classes IgG, IgM, IgA, IgD or IgE, or fragments, fragments or derivatives thereof, including Fab, F(ab')2, Fd, and single chain antibodies, diabodies, bispecific antibodies, bifunctional antibodies and derivatives thereof. The antibody may be an antibody isolated from the serum sample of mammal, a polyclonal antibody, affinity purified antibody, or mixtures thereof which exhibits sufficient binding specificity to a desired epitope or a sequence derived therefrom.

c. Coding Sequence

"Coding sequence" or "encoding nucleic acid" as used herein may mean refers to the nucleic acid (RNA or DNA molecule) that comprise a nucleotide sequence which encodes a protein. The coding sequence may further include initiation and termination signals operably linked to regulatory elements including a promoter and polyadenylation signal capable of directing expression in the cells of an individual or mammal to which the nucleic acid is administered.

d. Complement

"Complement" or "complementary" as used herein may mean a nucleic acid may mean Watson-Crick (e.g., A-T/U and C-G) or Hoogsteen base pairing between nucleotides or nucleotide analogs of nucleic acid molecules.

e. Consensus or Consensus Sequence

"Consensus" or "consensus sequence" as used herein may mean a synthetic nucleic acid sequence, or corresponding polypeptide sequence, constructed based on analysis of an alignment of multiple subtypes of a particular influenza antigen, that can be used to induce broad immunity against multiple subtypes or serotypes of a particular influenza antigen. Consensus FMDV antigens may include VP1, VP2, VP3, VP4, and C2 protease nucleotide and amino acid sequences. Also, synthetic antigens such as fusion proteins may be manipulated to consensus sequences (or consensus antigens).

f. Constant Current

"Constant current" as used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

g. Current Feedback or Feedback

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

h. Decentralized Current

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

i. Electroporation

"Electroporation," "electro-permeabilization," or "electro-kinetic enhancement" ("EP") as used interchangeably herein may refer to the use of a transmembrane electric field pulse to induce microscopic pathways (pores) in a biomembrane; their presence allows biomolecules such as plasmids, oligonucleotides, siRNA, drugs, ions, and water to pass from one side of the cellular membrane to the other.

j. Feedback Mechanism

"Feedback mechanism" as used herein may refer to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. A feedback mechanism may be performed by an analog closed loop circuit.

k. Fragment

"Fragment" as used herein may mean a portion or a nucleic acid that encodes a polypeptide capable of eliciting an immune response in a mammal substantially similar to that of the non-fragment for at least one FMDV subtype such as A, Asia 1, C, O, SAT1, SAT2, or SAT3. The fragments may comprise at least 10%, at least 20%, at least 30%, at least 40%, at least 50%, at least 60%, at least 70%, at least 80%, at least 90% or at least 95% of a FMDV protein encoded by a nucleic acid sequence of SEQ ID NOS: 1, 3, 5, 7, 9 or 11. The DNA fragments may be 30 or more nucleotides in length, 45 or more, 60 or more, 75 or more, 90 or more, 120 or more, 150 or more, 180 or more, 210 or more, 240 or more, 270 or more, 300 or more, 360 or more, 420 or more, 480 or more, 540 or more, 600 or more, 660 or more, 720 or more, 780 or more, 840 or more, 900 or more, 960 or more, 1020 or more, 1080 or more, 1140 or more, 1200 or more, 1260 or more, 1320 or more, 1380 or more, 1440 or more, 1500 or more, 1560 or more, 1620 or more, 1680 or more, 1740 or more, 1800 or more, 1860 or more, 1820 or more, 1880 or more, 1940 or more, 2000 or more, 2600 or more, 2700 or more, 2800 or more, 2900 or more, 2910 or more, 2920 or more, 2930 or more, 2931 or more, 2932 or more, 2933 or more, 2934 or more, 2935 or more, 2936 or more, 2937 or more, or 2938 or more in length DNA fragments may comprise coding sequences for the immunoglobulin leader such as IgE or IgG sequences.

DNA fragments may be fewer than 10 nucleotides, fewer than 20, fewer than 30, fewer than 40, fewer than 50, fewer than 60, fewer than 75, fewer than 90, fewer than 120, fewer than 150, fewer than 180, fewer than 210, fewer than 240, fewer than 270, fewer than 300, fewer than 360, fewer than 420, fewer than 480, fewer than 540, fewer than 600, fewer than 660, fewer than 720, fewer than 780, fewer than 840, fewer than 900, fewer than 960, fewer than 1020, fewer than 1080, fewer than 1140, fewer than 1200, fewer than 1260, fewer than 1320, fewer than 1380, fewer than 1440, fewer than 1500, fewer than 1560, fewer than 1620, fewer than 1680, or fewer than 1740 nucleotides, fewer than 1800, fewer than 1860, fewer than 1820, fewer than 1880, fewer than 1940, fewer than 2000, fewer than 2600, fewer than 2700, fewer than 2800, fewer than 2900, fewer than 2910, fewer than 2920, fewer than 2930, fewer than 2931, fewer than 2932, fewer than 2933, fewer than 2934, fewer than 2935, fewer than 2936, fewer than 2937, or fewer than 2938.

"Fragment" may also mean a polypeptide fragment that is capable of eliciting an immune response in a mammal substantially similar to that of the non-fragment for at least one FMDV subtype such as A, Asia 1, C, O, SAT1, SAT2, or SAT3. The fragment may be polypeptide fragment selected from at least one of the various encoding polypeptide sequences of the present invention, including SEQ ID NOs: 2, 4, 6, 8, 10, 12. Polypeptide fragment may be analyzed to contact at least one antigenic epitope as provided by a publicly available database such as the Los Alamos National Laboratory's FMDV Sequence Database. Fragments of proteins may comprise at least 10%, at least 20%, at least 30%, at least 40%, at least 50%, at least 60%, at least 70%, at least 80%, at least 90% or at least 95% of an FMDV protein set forth in the polyproteins shown in SEQ ID NOs: 2, 4, 6, 8, 10 or 12. Polypeptides may comprise amino acid sequences for the immunoglobulin leader such as IgE or IgG. The polypeptide fragments may be 30 or more amino acids in length, 45 or more, 60 or more, 75 or more, 90 or more, 120 or more, 150 or more, 180 or more, 210 or more, 240 or more, 270 or more, 300 or more, 360 or more, 420 or more, 480 or more, 540 or more, 600 or more, 660 or more, or 710 amino acids or more in length Polypeptide fragments may be fewer than 10 amino acids, fewer than 20, fewer than 30, fewer than 40, fewer than 50, fewer than 60, fewer than 75, fewer than 90, fewer than 120, fewer than 150, fewer than 180, fewer than 210, fewer than 240, fewer than 270, fewer than 300, fewer than 360, fewer than 420, fewer than 480, fewer than 540, fewer than 600, fewer than 660, fewer than 700, fewer than 701, fewer than 702, fewer than 703, fewer than 704, fewer than 705, fewer than 706, fewer than 707, fewer than 708, fewer than 709, or fewer than 710 amino acids in length.

l. Homology

Homology of multiple sequence alignments may be generated using ClustalW.

m. Identical

"Identical" or "identity" as used herein in the context of two or more nucleic acids or polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

n. Impedance

"Impedance" as used herein may be used when discussing the feedback mechanism and can be converted to a current value according to Ohm's law, thus enabling comparisons with the preset current.

o. Immune Response

"Immune response" as used herein may mean the activation of a host's immune system, e.g., that of a mammal, in response to the introduction of FMDV consensus antigen via the provided DNA plasmid vaccines. The immune response can be in the form of a cellular or humoral response, or both.

p. Nucleic Acid

"Nucleic acid" or "oligonucleotide" or "polynucleotide" as used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. The 2'-OH-group may be replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. Modified nucleotides also include nucleotides conjugated with cholesterol through, e.g., a hydroxyprolinol linkage as described in Krutzfeldt et al., Nature (Oct. 30, 2005), Soutschek et al., Nature 432:173-178 (2004), and U.S. Patent Publication No. 20050107325, which are incorporated herein by reference. Modified nucleotides and nucleic acids may also include locked nucleic acids (LNA), as described in U.S. Patent No. 20020115080, which is incorporated herein by reference. Additional modified nucleotides and nucleic acids are described in U.S. Patent Publication No. 20050182005, which is incorporated herein by reference. Modifications of the ribose-phosphate backbone may be done for a variety of reasons, e.g., to increase the stability and half-life of such molecules in physiological environments, to enhance diffusion across cell membranes, or as probes on a biochip. Mixtures of naturally occurring nucleic acids and analogs may be made; alternatively, mixtures of different nucleic acid analogs, and mixtures of naturally occurring nucleic acids and analogs may be made.

q. Operably Linked

"Operably linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

r. Promoter

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

s. Stringent Hybridization Conditions

"Stringent hybridization conditions" as used herein may mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

t. Substantially Complementary

"Substantially complementary" as used herein may mean that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or that the two sequences hybridize under stringent hybridization conditions.

u. Substantially Identical

"Substantially identical" as used herein may mean that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or with respect to nucleic acids, if the first sequence is substantially complementary to the complement of the second sequence.

v. Subtype or Serotype

"Subtype" or "serotype" as used herein interchangeably and in reference to FMDV viruses, and means genetic variants of a FMDV virus antigen such that one subtype is recognized by an immune system apart from a different subtype.

w. Variant

"Variant" used herein with respect to a nucleic acid may mean (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

x. Vector

"Vector" used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

2. FMDV Proteins and Coding Sequences

The genomes for each of subtypes A, C, O, Asia, SAT1, SAT2 and SAT3 are found in GenBank at the following accession number:

A: JF749843
C: NC_002554
O: JF749851
Asia: DQ533483
SAT-1: JF749860
SAT-2: JF749862
SAT-3: NC_011452.

These can be used to locate coding sequences for each of VP1, VP2, VP3 and VP4 for each of subtypes A, C, O, Asia, SAT1, SAT2 and SAT3. Similarly, as noted above, WO 2011/054011 discloses FMDV vaccines with VP1, VP2, VP3, VP4 from FMDV subtypes A, C, O, Asia, SAT1, SAT2 and SAT3, albeit using a different design. One skilled in the art could identify coding sequences for each of FMDV proteins VP1, VP2, VP3, VP4 from subtypes A, C, O, Asia, SAT1, SAT2 and SAT3, using the information in WO 2011/054011 and GenBank.

Homologous proteins which are 95% or more, 96% or more, 97% or more, 98% or more, or 99% or more homologous to FMDV proteins VP1, VP2, VP3, or VP4 from subtypes A, C, O, Asia, SAT1, SAT2 or SAT3, may be used in some constructs.

Fragments of FMDV proteins VP1, VP2, VP3, or VP4 from subtypes A, C, O, Asia, SAT1, SAT2 or SAT3, having 95% or more, 96% or more, 97% or more, 98% or more, or 99% or more of the full length sequence of may be used in some constructs.

Fragments of proteins which are 95% or more, 96% or more, 97% or more, 98% or more, or 99% or more homologous to FMDV proteins VP1, VP2, VP3, or VP4 from subtypes A, C, O, Asia, SAT1, SAT2 or SAT3, and which have 95% or more, 96% or more, 97% or more, 98% or more, or 99% or more of the full length sequence of may be used in some constructs.

Coding sequences for these FMDV proteins, homologous proteins, fragments of FMDV proteins and fragments of homologous proteins may be used in constructs.

A native proteolytic cleavage site can be present in between each of the consensus antigen sequences, such as the amino acid sequence: RGRKRRS.

Provided herein is an antigen capable of eliciting an immune response in a mammal against one or more foot-and-mouth disease virus (FMDV) subtypes. The antigen may be a FMDV antigen comprising capsid protein VP1, VP2, VP3, VP4, a consensus thereof, a variant thereof, a fragment thereof or a combination thereof. The FMDV antigen may be from FMDV subtype A, Asia 1, C, O, SAT1, SAT2, or SAT3. The FMDV antigen may contain at least one antigenic epitope that may be effective against particular FMDV immunogens against which an immune response can be induced. The empty viral capsid proteins VP1-VP4 of the FMDV antigen provides an entire repertoire of immunogenic sites and epitopes present in an intact FMDV virus. The consensus FMDV antigen sequence may be derived from FMDV antigen sequences from a plurality of FMDV viruses of one FMDV subtype. The consensus FMDV antigen may comprise VP1, VP2, VP3, and VP4 FMDV subtype consensus protein sequences, which may be a consensus VP1-VP4 protein. The consensus VP1-VP4 protein may comprise at least one FMDV protein 3C cleavage site. The protein 3C cleavage site may be present in between each of consensus VP1, VP2, VP3, and VP4 sequences of the consensus VP1-4 protein. Cleavage of the consensus VP1-VP4 protein by protein 3C may cleave the consensus VP1-VP4 protein to produce a consensus VP1-, a consensus VP2-, a consensus VP3-, and a consensus VP4 protein. Alternatively, a native proteolytic cleavage site can be present in between each of the consensus antigen sequences, such as the amino acid sequence: RGRKRRS.

In some embodiments, proteins are 80% homologous. In some embodiments, proteins are 90% homologous. In some embodiments, proteins are 95% homologous. In some embodiments, proteins are 96% homologous. In some embodiments, proteins are 97% homologous. In some embodiments, proteins are 98% homologous. In some embodiments, proteins are 99% homologous.

Provided herein are coding sequences of antigens capable of eliciting an immune response in a mammal against one or more foot-and-mouth disease virus (FMDV) subtypes. The antigen may be a FMDV antigen comprising capsid protein VP1, VP2, VP3, VP4, a consensus thereof, a variant thereof, a fragment thereof or a combination thereof. The FMDV antigen may be from FMDV subtype A, Asia 1, C, O, SAT1, SAT2, or SAT3. The FMDV antigen may contain at least one antigenic epitope that may be effective against particular FMDV immunogens against which an immune response can be induced. The empty viral capsid proteins VP1-4 of the FMDV antigen provides an entire repertoire of immunogenic sites and epitopes present in an intact FMDV virus. The consensus FMDV antigen sequence may be derived from FMDV antigen sequences from a plurality of FMDV viruses of one FMDV subtype. The consensus FMDV antigen may comprise VP1, VP2, VP3, and VP4 FMDV subtype consensus protein sequences, which may be a consensus VP1-4 protein. The consensus VP1-4 protein may comprise at least one FMDV protein 3C cleavage site. The protein 3C cleavage site may be present in between each of consensus VP1, VP2, VP3, and VP4 sequences of the consensus VP1-4 protein. Cleavage of the consensus VP1-4 protein by protein 3C may cleave the consensus VP1-4 protein to produce a consensus VP1-, a consensus VP2-, a consensus VP3-, and a consensus VP4 protein. Alternatively, a native proteolytic cleavage site can be present in between each of the consensus antigen sequences, such as the amino acid sequence: RGRKRRS. Coding sequences for fusion proteins comprising consensus of protease 3C are provided.

Additionally, coding sequences may encode proteins may be fragments of the proteins described herein. In some embodiments, coding sequences encode proteins that are 20% of the consensus protein. In some embodiments, coding sequences encode proteins that are 30% of the consensus protein. In some embodiments, coding sequences encode proteins that are 40% of the consensus protein. In some embodiments, coding sequences encode proteins that are 50% of the consensus protein. In some embodiments, coding sequences encode proteins that are 60% of the consensus protein. In some embodiments, coding sequences encode proteins that are 70% of the consensus protein. In some embodiments, coding sequences encode proteins that are 85% of the consensus protein. In some embodiments, coding sequences encode proteins that are 90% of the consensus protein. In some embodiments, coding sequences encode proteins that are 95% of the consensus protein. In some embodiments, coding sequences encode proteins that are 96% of the consensus protein. In some embodiments, coding sequences encode proteins that are 97% of the consensus protein. I Additionally, coding sequences may encode proteins that are homologous to the proteins provided herein. In some embodiments, coding sequences encode proteins that are 80% homologous. In some embodiments, coding sequences encode proteins that are 90% homologous. In some embodiments, coding sequences encode proteins that are 95% homologous. In some embodiments, coding sequences encode proteins that are 96% homologous. In some embodiments, coding sequences encode proteins that are 97% homologous. In some embodiments, coding sequences encode proteins that are 98% homologous. In some embodiments, coding sequences encode proteins that are 99% homologous.

Additionally, coding sequences encode proteins that are fragments of proteins homologous to proteins described herein. In some embodiments, coding sequences encode proteins that are 20% of the homologous protein. In some embodiments, coding sequences encode proteins that are 30% of the homologous protein. In some embodiments, coding sequences encode proteins that are 40% of the homologous protein. In some embodiments, coding sequences encode proteins that are 50% of the homologous protein. In some embodiments, coding sequences encode proteins that are 60% of the homologous protein. In some embodiments, coding sequences encode proteins that are 70% of the homologous protein. In some embodiments, coding sequences encode proteins that are 80% of the homologous protein. In some embodiments, coding sequences encode proteins that are 90% of the homologous protein. In some embodiments, coding sequences encode proteins that are 95% of the homologous protein. In some embodiments, coding sequences encode proteins that are 96% of the homologous protein. In some embodiments, coding sequences encode proteins that are 97% of the homologous protein. In some embodiments, coding sequences encode proteins that are 98% of the homologous protein. In some embodiments, coding sequences encode proteins that are 99% of the homologous protein.

3. Plasmid

Provided herein is a vector that is capable of expressing one or more FMDV antigens in the cell of a mammal in a quantity effective to elicit an immune response in the mammal. The vector may comprise heterologous nucleic acid encoding the FMDV antigen. The vector may be a plasmid. The plasmid may be useful for transfecting cells with nucleic acid encoding a FMDV antigen, which the transformed host cell is cultured and maintained under conditions wherein expression of the FMDV antigen takes place.

The plasmid may comprise a nucleic acid encoding a FMDV antigen selected from the proteins provided herein, fragments thereof, homologous sequences thereof and fragments of homologous. The plasmid may further comprise an initiation codon or leader sequence, which may be upstream of the coding sequence, and a stop codon, which may be downstream of the coding sequence. The initiation and termination codon may be in frame with the coding sequence.

The plasmid may also comprise a promoter that is operably linked to the coding sequence. The promoter operably linked to the coding sequence a may be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, or human metalothionein. The promoter may also be a tissue specific promoter, such as a muscle or skin specific promoter, natural or synthetic. Examples of such promoters are described in US patent application publication no. US20040175727, the contents of which are incorporated herein in its entirety.

The plasmid may also comprise a polyadenylation signal, which may be downstream of the coding sequence. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 plasmid (Invitrogen, San Diego, Calif.).

The plasmid may also comprise an enhancer upstream of the coding sequence. The enhancer may be human actin, human myosin, human hemoglobin, human muscle creatine or a viral enhancer such as one from CMV, FMDV, RSV or EBV. Polynucleotide function enhances are described in U.S. Pat. Nos. 5,593,972, 5,962,428, and WO94/016737, the contents of each are fully incorporated by reference.

The plasmid may also comprise a mammalian origin of replication in order to maintain the plasmid extrachromosomally and produce multiple copies of the plasmid in a cell. The plasmid may be pVAX1, pCEP4 or pREP4 from Invitrogen (San Diego, Calif.), which may comprise the Epstein Barr virus origin of replication and nuclear antigen EBNA-1 coding region, which may produce high copy episomal replication without integration. The backbone of the plasmid may be pAV0242. The plasmid may be a replication defective adenovirus type 5 (Ad5) plasmid.

The plasmid may also comprise a regulatory sequence, which may be well suited for gene expression in a cell into which the plasmid is administered. The coding sequence may comprise a codon, which may allow more efficient transcription of the coding sequence in the host cell.

The coding sequence may comprise an Ig leader sequence. The leader sequence may be 5' of the coding sequence. The consensus protein encoded by this sequence may comprise an N-terminal Ig leader followed by a consensus protein. The N-terminal Ig leader may be IgE or IgG.

The plasmid may be pSE420 (Invitrogen, San Diego, Calif.), which may be used for protein production in *Escherichia coli* (*E. coli*). The plasmid may also be pYES2 (Invitrogen, San Diego, Calif.), which may be used for protein production in *Saccharomyces cerevisiae* strains of yeast. The plasmid may also be of the MAXBAC™ complete baculovirus expression system (Invitrogen, San Diego, Calif.), which may be used for protein production in insect cells. The plasmid may also be pcDNA I or pcDNA3 (Invitrogen, San Diego, Calif.), which maybe used for protein production in mammalian cells such as Chinese hamster ovary (CHO) cells.

Plasmids may comprise one or more coding sequences encoding one or more of VP1, VP2, VP3, VP4, and 3C from one or more subtypes such as Asia, A, O, C, SAT1, SAT2 and SAT3.

In some embodiments, a plasmid comprises coding sequences for multiple distinct consensus FMDV antigens VP1, VP2, VP3, VP4 and 3C from subtype Asia, A, O, C, SAT1, SAT2 or SAT3.

In some embodiments, a plasmid comprises coding sequences for multiple distinct consensus FMDV antigens VP1, VP2, VP3 and VP4 from subtype Asia, A, O, C, SAT1, SAT2 or SAT3.

In some embodiments, a plasmid comprises coding sequences for two distinct consensus FMDV antigen VP1 from two of subtypes Asia, A, O, and C such as VP1 from subtype Asia VP1 from subtype O, or a VP1 from t subtype A and VP1 from subtype C.

In some embodiments, a plasmid comprises coding sequences for a consensus FMDV antigen VP1 such as VP1 subtype Asia, VP1 subtype A, VP1 subtype O or VP1 subtype C.

The coding sequence can be encoded by a distinct DNA plasmid, all regulated by an operably linked promoter, e.g., a DNA plasmid having an encoding sequence regulated by one or mote promoters the encoding sequence comprising multiple consensus FMDV antigens.

The vector can be pVAX1 or a pVax1 variant with changes such as the variant plasmid described herein. The variant pVax1 plasmid is a 2998 basepair variant of the backbone vector plasmid pVAX1 (Invitrogen, Carlsbad Calif.). The CMV promoter is located at bases 137-724. The T7 promoter/priming site is at bases 664-683. Multiple cloning sites are at bases 696-811. Bovine GH polyadenylation signal is at bases 829-1053. The Kanamycin resistance gene is at bases 1226-2020. The pUC origin is at bases 2320-2993.

Based upon the sequence of pVAX1 available from Invitrogen, the following mutations were found in the sequence of pVAX1 that was used as the backbone for plasmids 1-6 set forth herein:

C>G241 in CMV promoter

C>T 1942 backbone, downstream of the bovine growth hormone polyadenylation signal (bGHpolyA)

A>—2876 backbone, downstream of the Kanamycin gene

C>T 3277 in pUC origin of replication (Ori) high copy number mutation (see Nucleic Acid Research 1985)

G>C 3753 in very end of pUC Ori upstream of RNASeH site

Base pairs 2, 3 and 4 are changed from ACT to CTG in backbone, upstream of CMV promoter.

The backbone of the vector can be pAV0242. The vector can be a replication defective adenovirus type 5 (Ad5) vector.

The plasmid may also comprise a regulatory sequence, which may be well suited for gene expression in a cell into which the plasmid is administered. The coding sequence may comprise a codon that may allow more efficient transcription of the coding sequence in the host cell.

The coding sequence may also comprise an Ig leader sequence. The leader sequence may be 5' of the coding sequence. The consensus antigens encoded by this sequence may comprise an N-terminal Ig leader followed by a consensus antigen protein. The N-terminal Ig leader may be IgE or IgG.

The plasmid may be pSE420 (Invitrogen, San Diego, Calif.), which may be used for protein production in *Escherichia coli* (*E. coli*). The plasmid may also be pYES2 (Invitrogen, San Diego, Calif.), which may be used for protein production in *Saccharomyces cerevisiae* strains of yeast. The plasmid may also be of the MAXBAC™ complete baculovirus expression system (Invitrogen, San Diego, Calif.), which may be used for protein production in insect cells. The plasmid may also be pcDNA I or pcDNA3 (Invitrogen, San Diego, Calif.), which may be used for protein production in mammalian cells such as Chinese hamster ovary (CHO) cells.

4. Vaccine

While not being bound by scientific theory, a vaccine that can be used to elicit an immune response (humoral, cellular, or both) broadly against FMDV may comprise one or more coding sequences set forth above, i.e. nucleic acid sequences that encodes one or more proteins VP1, VP2, VP3, CVP4 and 2A from subtypes selected from the group consisting of: FMDV subtypes such as A, Asia 1, C, O, SAT1, SAT2, SAT3, or combinations thereof. In some embodiment. The vaccine may also comprise a nucleic acid encoding a FMDV C3 protease, which may be a consensus C3 protease nucleic acid.

This includes:

an isolated nucleic acid comprising a sequence encoding the consensus amino acid sequence of at least VP1-VP3, and preferably, VP1-4 of foot-and-mouth disease virus that elicits a cross-reactive immune response in a vaccinated subject against multiple subtypes of FMD, including A, Asia 1, C, O, SAT1, SAT2, SAT3, SAT4. The nucleic acid may comprise a sequence selected from the group consisting of (a) SEQ ID NO: 1; a nucleotide sequence encoding SEQ ID NO:2; (b) SEQ ID NO:3; a nucleotide sequence encoding SEQ ID NO:4; (c) SEQ ID NO:5; a nucleotide sequence encoding SEQ ID NO:6; d) SEQ ID NO:7; a nucleotide sequence encoding SEQ ID NO:8; e) SEQ ID NO:9; a nucleotide sequence encoding SEQ ID NO:10; and f) SEQ ID NO:11; a nucleotide sequence encoding SEQ ID NO:12.

Provided herein is a vaccine capable of generating in a mammal an immune response against one or more FMDV subtypes. The vaccine may comprise the plasmid as discussed above. The vaccine may comprise a plurality of the plasmids each directed to one or more FMDV subtypes such as A, Asia 1, C, O, SAT1, SAT2, SAT3, or combinations thereof. The vaccine may also comprise the FMDV antigens themselves directed against one or more FMDV subtypes such as A, Asia 1, C, O, SAT1, SAT2, SAT3, or combinations thereof. The vaccine may also comprise plasmids directed to FMDV subtypes from particular regions in the world, for example, Asia, Europe and sub-Africa. Alternatively or in addition, the vaccine may comprise proteins of one or more FMDV subtypes such as A, Asia 1, C, O, SAT1, SAT2, SAT3, or combinations thereof. The vaccine may also comprise the FMDV antigens themselves directed against one or more FMDV subtypes such as A, Asia 1, C, O, SAT1, SAT2, SAT3, or combinations thereof. The vaccine may also comprise plasmids and/or proteins directed to FMDV subtypes from particular regions in the world, for example, Asia, Europe and sub-Africa. The vaccine may be provided to induce a therapeutic or prophylactic immune response.

Provided herein are pharmaceutical compositions according to the present invention which comprise about 1 nanogram to about 10 mg of DNA. In some embodiments, pharmaceutical compositions according to the present invention comprise from between: 1) at least 10, 15, 20, 25, 30, 35, 40, 45, 50, 55, 60, 65, 70, 75, 80, 85, 90, 95 or 100 nanograms, or at least 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995 or 1000 micrograms, or at least 1.5, 2, 2.5, 3, 3.5, 4, 4.5, 5, 5.5, 6, 6.5, 7, 7.5, 8, 8.5, 9, 9.5 or 10 mg or more; and 2) up to and including 15, 20, 25, 30, 35, 40, 45, 50, 55, 60, 65, 70, 75, 80, 85, 90, 95 or 100 nanograms, or up to and including 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995, or 1000 micrograms, or up to and including 1.5, 2, 2.5, 3, 3.5, 4, 4.5, 5, 5.5, 6, 6.5, 7, 7.5, 8, 8.5, 9, 9.5 or 10 mg. In some embodiments, pharmaceutical compositions according to the present invention comprise about 5 nanogram to about 10 mg of DNA. In some embodiments, pharmaceutical compositions according to the present invention comprise about 25 nanogram to about 5 mg of DNA. In some embodiments, the pharmaceutical compositions contain about 50 nanograms to about 1 mg of DNA. In some embodiments, the pharmaceutical compositions contain about 0.1 to about 500 micrograms of DNA. In some embodiments, the pharmaceutical compositions contain about 1 to about 350 micrograms of DNA. In some embodiments, the pharmaceutical compositions contain about 5 to about 250 micrograms of DNA. In some embodiments, the pharmaceutical compositions contain about 10 to about 200 micrograms of DNA. In some embodiments, the pharmaceutical compositions contain about 15 to about 150 micrograms of DNA. In some embodiments, the pharmaceutical compositions contain about 20 to about 100 micrograms of DNA. In some embodiments, the pharmaceutical compositions contain about 25 to about 75 micrograms of DNA. In some embodiments, the pharmaceutical compositions contain about 30 to about 50 micrograms of DNA. In some embodiments, the pharmaceutical compositions contain about 35 to about 40 micrograms of DNA. In some embodiments, the pharmaceutical compositions contain about 100 to about 200 microgram DNA. In some embodiments, the pharmaceutical compositions comprise about 10 microgram to about 100 micrograms of DNA. In some embodiments, the pharmaceutical compositions comprise about 20 micrograms to about 80 micrograms of DNA. In some embodiments, the pharmaceutical compositions comprise about 25 micrograms to about 60 micrograms of DNA. In some embodiments, the pharmaceutical compositions comprise about 30 nanograms to about 50 micrograms of DNA. In some embodiments, the pharmaceutical compositions comprise about 35 nanograms to about 45 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms of DNA. In some preferred embodiments, the pharmaceutical compositions contain about 100 to about 200 microgram DNA.

The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

Preferably the pharmaceutical composition is a vaccine, and more preferably a DNA vaccine.

The vaccine may be a DNA vaccine. The DNA vaccine may comprise a plurality of the same or different plasmids comprising nucleic acid coding sequences for one or more of consensus prostate antigens. The DNA vaccine may comprise one or more nucleic acid sequences that encode one or more of consensus prostate antigens. When the DNA vaccine comprises coding sequences of more than one consensus prostate antigens all such sequences may be present on a single plasmid, or each such sequences may be present on a different plasmids.

In some embodiments, vaccines may comprise nucleic acid sequences that encode one or more of consensus prostate antigens in combination with one or more of consensus prostate antigens.

DNA vaccines are disclosed in U.S. Pat. Nos. 5,593,972, 5,739,118, 5,817,637, 5,830,876, 5,962,428, 5,981,505, 5,580,859, 5,703,055, and 5,676,594, which are incorporated herein fully by reference. The DNA vaccine can further comprise elements or reagents that inhibit it from integrating into the chromosome. The vaccine can be an RNA of the prostate antigen. The RNA vaccine can be introduced into the cell.

The vaccine can be a recombinant vaccine comprising the genetic construct or antigen described above. The vaccine can also comprise one or more consensus prostate antigens in the form of one or more protein subunits, or one or more attenuated viral particles comprising one or more consensus antigens. The attenuated vaccine can be attenuated live vaccines, killed vaccines and vaccines that use recombinant vectors to deliver foreign genes that encode one or more consensus prostate antigens, and well as subunit and protein vaccines. Examples of attenuated live vaccines, those using recombinant vectors to deliver prostate antigens, subunit vaccines and glycoprotein vaccines are described in U.S. Pat. Nos. 4,510,245; 4,797,368; 4,722,848; 4,790,987; 4,920,209; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference. Vaccines may comprise plasmids in combination with other vaccine components such as FMDV proteins or expression vectors encoding proteins.

The vaccine provided may be used to induce immune responses including therapeutic or prophylactic immune responses. Antibodies and/or killer T cells may be generated which are directed to the consensus prostate antigen. Such antibodies and cells may be isolated.

The vaccine may further comprise a pharmaceutically acceptable excipient. The pharmaceutically acceptable excipient may be functional molecules as vehicles, adjuvants, carriers, or diluents. The pharmaceutically acceptable excipient may be a transfection facilitating agent, which may include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the vaccine at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the DNA plasmid vaccines may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient may be an adjuvant. The adjuvant may be other genes that are expressed in alternative plasmid or are delivered as proteins in combination with the plasmid above in the vaccine. The adjuvant may be selected from the group consisting of: α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial *thymus*-expressed chemokine (TECK), mucosae-associated epithelial chemokine (MEC), IL-12, IL-15, MHC, CD80, CD86 including IL-15 having the signal sequence deleted and optionally including the signal peptide from IgE. The adjuvant may be IL-12, IL-15, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof.

Other genes which may be useful adjuvants include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRCS, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The vaccine may further comprise a genetic vaccine facilitator agent as described in U.S. Ser. No. 021,579 filed Apr. 1, 1994, which is fully incorporated by reference.

The vaccine may be formulated according to the mode of administration to be used. An injectable vaccine pharmaceutical composition may be sterile, pyrogen free and particulate free. An isotonic formulation or solution may be used. Additives for isotonicity may include sodium chloride, dextrose, mannitol, sorbitol, and lactose. The vaccine may comprise a vasoconstriction agent. The isotonic solutions may include phosphate buffered saline. Vaccine may further comprise stabilizers including gelatin and albumin. The stabilizing may allow the formulation to be stable at room or ambient temperature for extended periods of time such as LGS or polycations or polyanions to the vaccine formulation.

5. Methods of Delivery The Vaccine

Provided herein is a method for delivering the vaccine for providing genetic constructs and proteins of the FMDV antigen which comprise epitopes that make them particular effective against immunogens of FMDV against which an immune response can be induced. The method of delivering the vaccine or vaccination may be provided to induce a therapeutic and prophylactic immune response. The vaccination process may generate in the mammal an immune response against a plurality of FMDV subtypes. The vaccine may be delivered to an individual to modulate the activity of the mammal's immune system and enhance the immune response. The delivery of the vaccine may be the transfection of the FMDV antigen as a nucleic acid molecule that is expressed in the cell and delivered to the surface of the cell upon which the immune system recognized and induces a cellular, humoral, or cellular and humoral response. The delivery of the vaccine may be use to induce or elicit and immune response in mammals against a plurality of FMDV viruses by administering to the mammals the vaccine as discussed above.

Upon delivery of the vaccine and plasmid into the cells of the mammal, the transfected cells will express and secrete consensus capsids for each of the plasmids injected from the vaccine. These secreted capsid proteins will be recognized as foreign by the immune system and antibodies will be made against them. These antibodies will be maintained by the immune system and allow for rapid clearing of subsequent FMDV challenge.

The vaccine may be administered to a mammal to elicit an immune response in a mammal. The mammal may be human, primate, non-human primate, cow, cattle, sheep, goat, antelope, bison, water buffalo, bison, bovids, deer, hedgehogs, elephants, llama, alpaca, mice, rats, and chicken.

a. Combination Treatments

The vaccine may be administered in combination with other proteins or genes encoding α-interferon, γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE, IL-12, IL-15, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRCS, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof or combinations thereof. The vaccine may also be administered in combination with CTACK protein, TECK protein, MEC protein or functional fragments thereof.

The vaccine may be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition may be administered as a suitably acceptable formulation in accordance with normal veterinary practice. The veterinarian can readily determine the dosing regimen and route of administration that is most appropriate for a particular animal. The vaccine may be administered by traditional syringes, needleless injection devices, "microprojectile bombardment gone guns", or other physical methods such as electroporation ("EP"), "hydrodynamic method", or ultrasound.

The plasmid of the vaccine may be delivered to the mammal by several well known technologies including DNA injection (also referred to as DNA vaccination) with and without in vivo electroporation, liposome mediated, nanoparticle facilitated, recombinant vectors such as recombinant adenovirus, recombinant adenovirus associated virus and recombinant vaccinia. The FMDV antigen may be delivered via DNA injection and along with in vivo electroporation.

b. Electroporation

Administration of the vaccine via electroporation of the plasmids of the vaccine may be accomplished using electroporation devices that can be configured to deliver to a desired tissue of a mammal a pulse of energy producing a constant current similar to a preset current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electronporation may be accomplished using the VGXP Cellectra™ system to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 μs, 20 μs, 10 μs or 1 μs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the DNA vaccines of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that may be used for facilitating delivery of the DNA vaccines include those provided in co-pending and co-owned U.S. patent application Ser. No. 11/874,072, filed Oct. 17, 2007, which claims the benefit under 35 USC 119(e) to U.S. Provisional Applications Ser. Nos. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

c. Method of Preparing Vaccine

Provided herein are methods for preparing the vaccine. In some embodiments, the methods are methods of preparing the vaccines comprising DNA plasmids. The DNA plasmids, after the final subcloning step into the mammalian expression plasmid, can be used to inoculate a cell culture in a large scale fermentation tank, using known methods in the art. The plasmid is transformed into a compatible host cell and cultured and maintained under conditions wherein expression of the FMDV antigen takes place. The FMDV antigen may be recovered from the culture either by lysing cells or from the culture medium and isolated. The isolated VP1-4 consensus proteins may be used in the vaccine as a natural source of antibodies. The FMDV antigen may be produce by recombinant techniques using automated synthesizers may also be employed to produce isolated essential pure FMDV antigen. These techniques may be useful for introducing variants of the FMDV antigen for particular subtypes of FMDV.

The DNA plasmids for use with the EP devices of the present invention can be formulated or manufactured using a combination of known devices and techniques, but preferably they are manufactured using an optimized plasmid manufacturing technique that is described in a licensed, co-pending U.S. provisional application U.S. Ser. No. 60/939,792, which was filed on May 23, 2007. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

EXAMPLES

Example 1

As set out in FIGS. 1-17 constructs of some embodiments have been made and tested. These figures show that vaccines were made and data was generated from their use.

Figure 7:
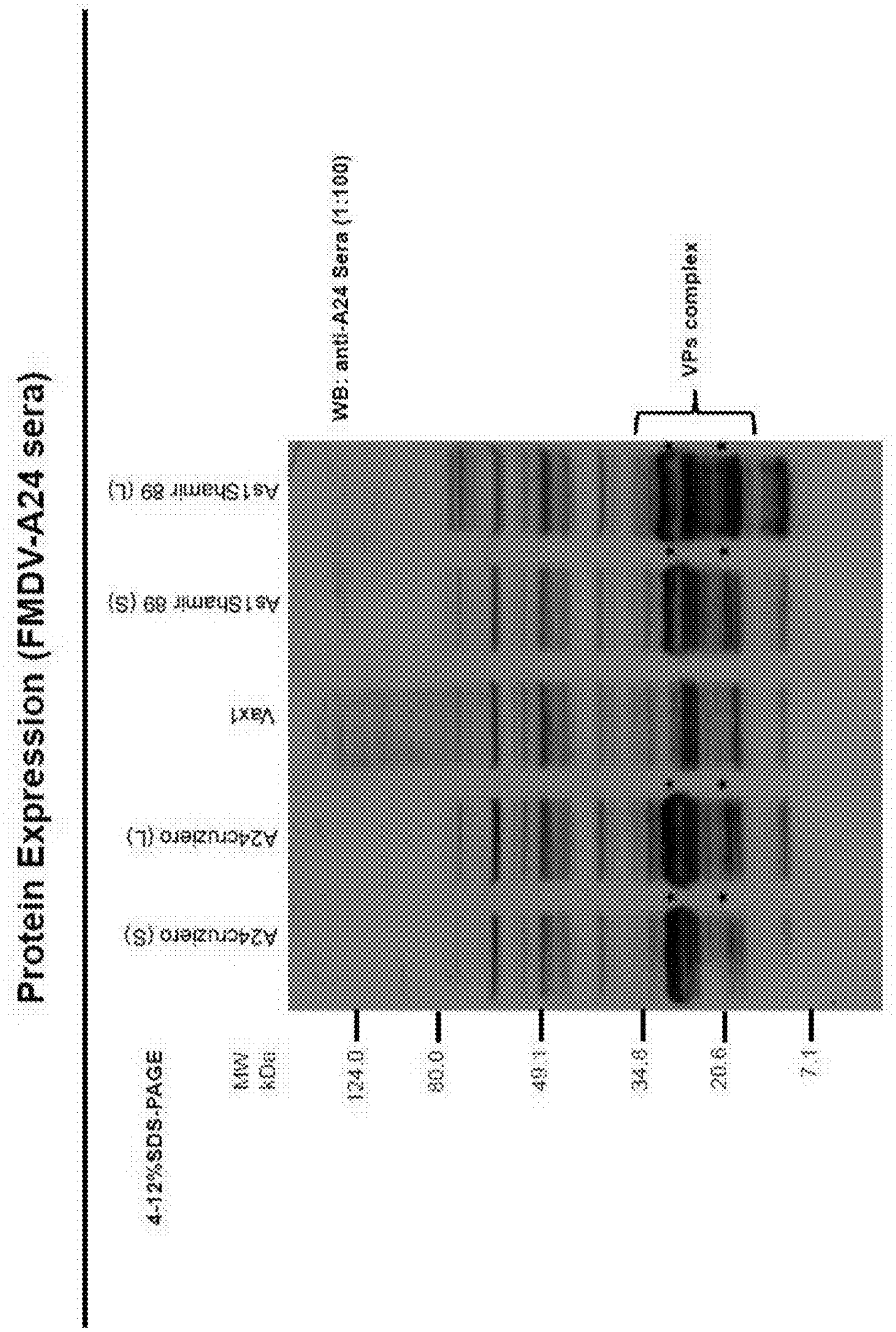
FIG. 7 shows experimental results of protein expression.
Figure 17:
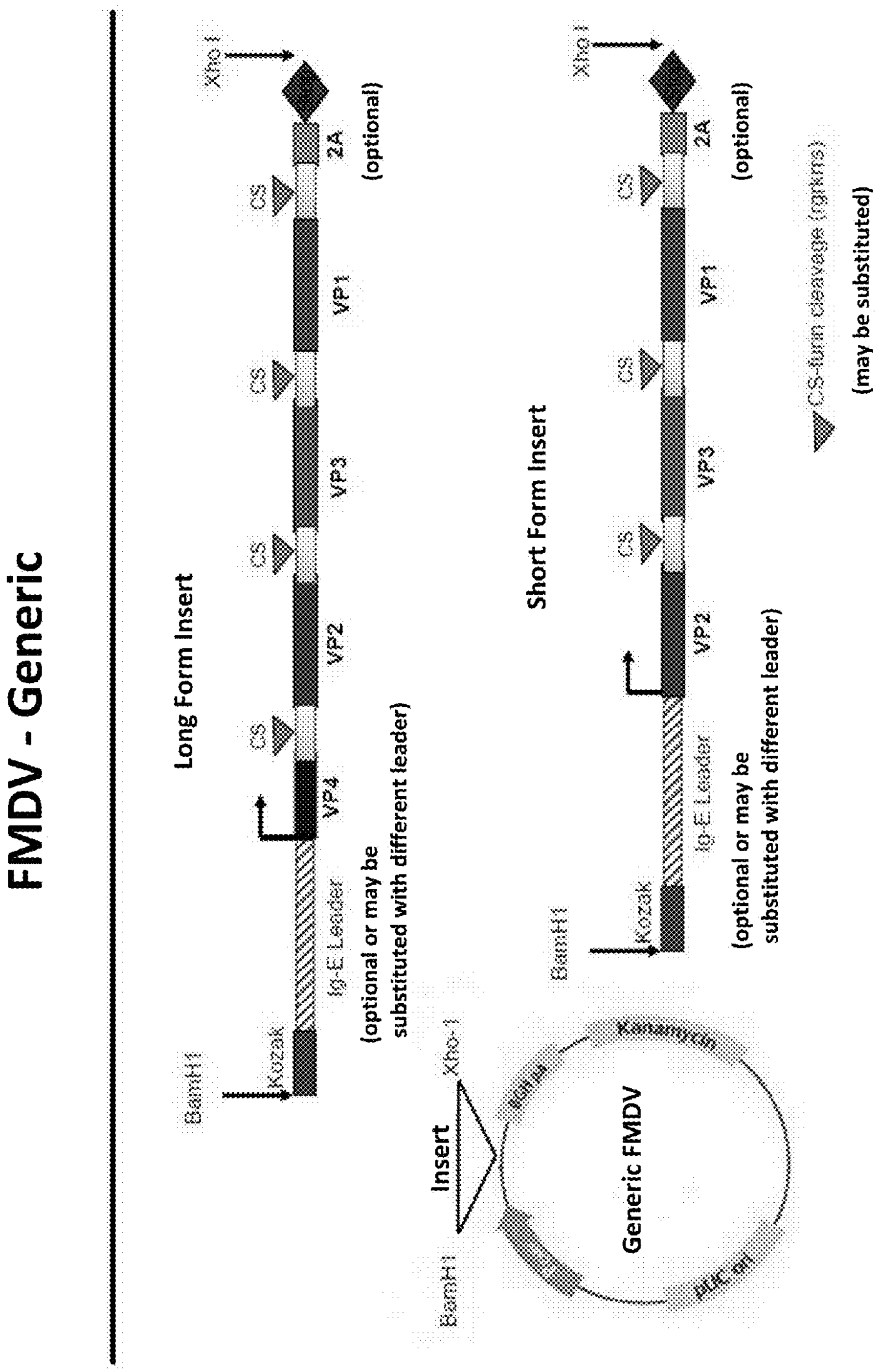
FIG. 17 shows schematic representation of a generic FMDV DNA vaccine construct, indicating that Insert is clones into a BamH1 and Xho-1 sites. A plasmid map of Generic FMDV vaccine is based upon the plasmid pVAX. Examples of the FMDV inserts may be the long form, which is shown in FIG. 17 as Long Form Insert or the short form, which is shown in FIG. 7 as Short Form Insert. The IgE leader shown in each form is indicated to be optional or may substituted with a different leader. The 2A sequence is indicated as optional and the furin cleavage site (rgrkrrs—SEQ ID NO:27) is indicated as being substitutable.

FIG. 17 shows schematic representation of a generic FMDV DNA vaccine construct, indicating that Insert is clones into a BamH1 and Xho-1 sites. A plasmid map of Generic FMDV vaccine is based upon the plasmid pVAX. Examples of the FMDV inserts may be the long form, which is shown in FIG. 17 as Long Form Insert or the short form, which is shown in FIG. 7 as Short Form Insert. The IgE leader shown in each form is indicated to be optional or may substituted with a different leader. The 2A sequence is indicated as optional and the furin cleavage site (rgrkrrs—SEQ ID NO:27) is indicated as being substitutable.

Figure 3:
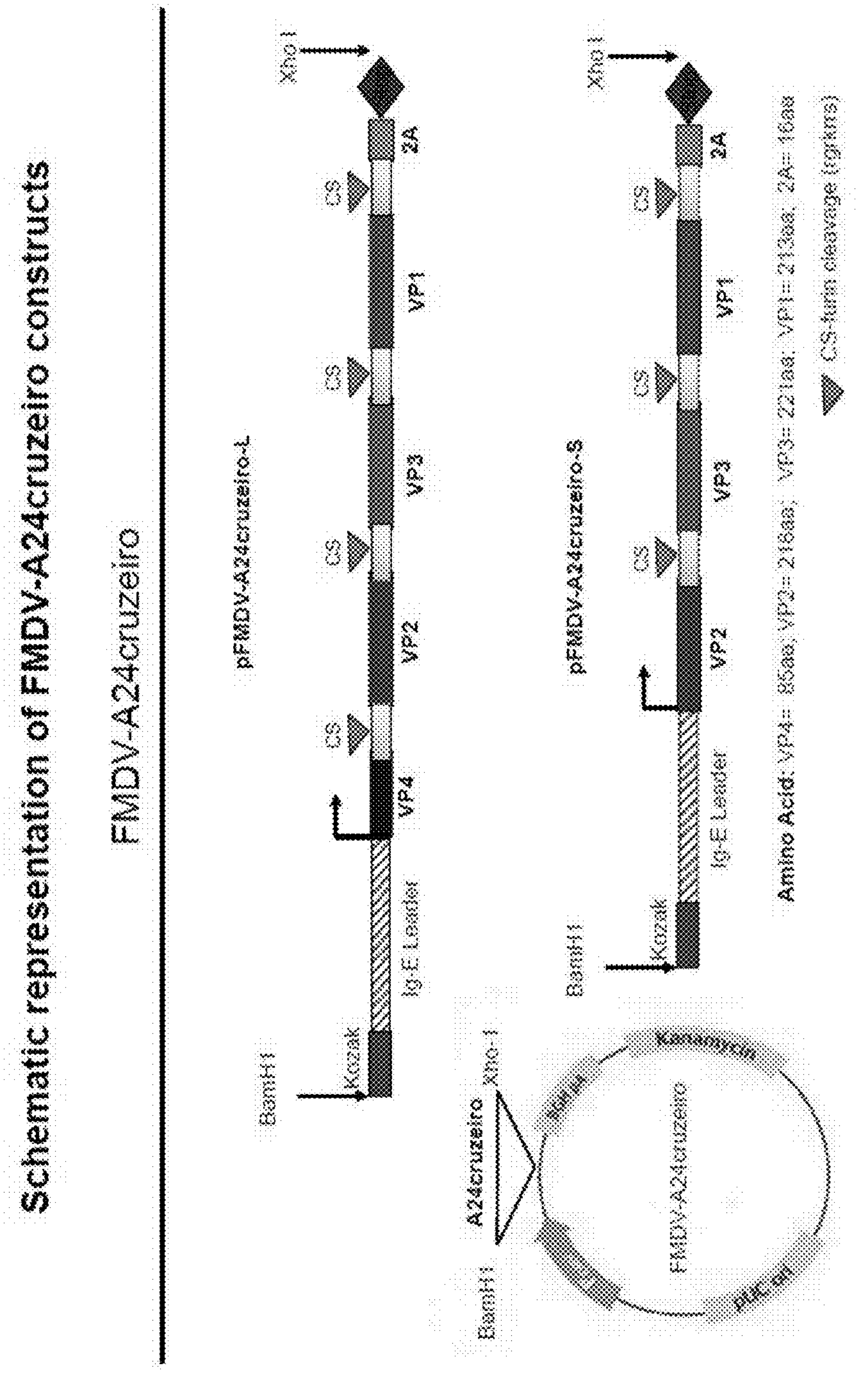
FIG. 3 shows schematic representation of a FMDV-A24cruzeiro DNA vaccine construct, indicating that an A24cruzeiro insert is clones into a BamH1 and Xho-1 sites. A plasmid map is based upon the plasmid pVAX. Examples of the FMDV-A24cruzeiro insert may be the long form, which is shown in FIG. 3 as pFMDV-A24cruzeiro-L or the short form, which is shown in FIG. 3 as pFMDV-A24cruzeiro-S.
Figure 5:
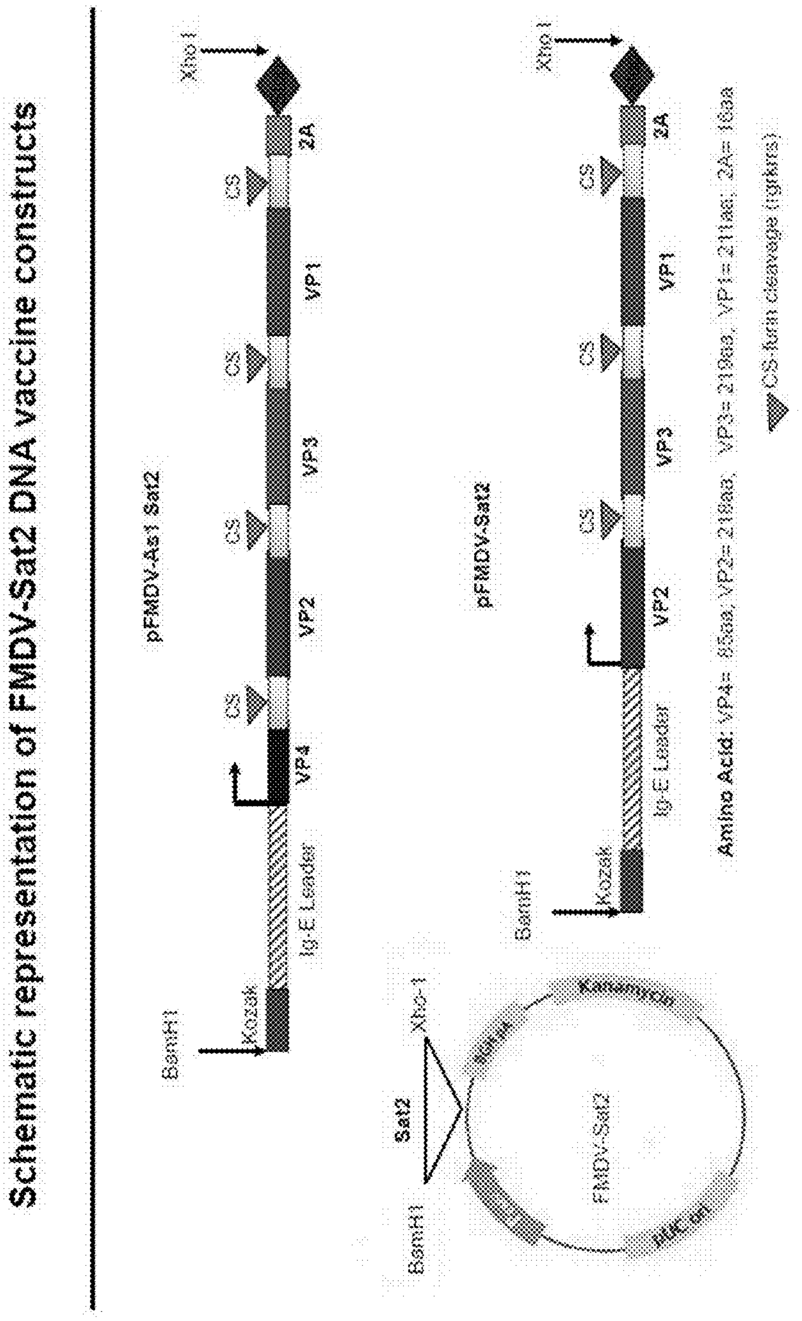
FIG. 5 shows schematic representation of a FMDV-Sat2 DNA vaccine construct, indicating that a Sat2 insert is clones into a BamH1 and Xho-1 sites. A plasmid map is based upon the plasmid pVAX. Examples of the FMDV-Sat insert may be the long form, which is shown in FIG. 5 as pFMDV-As1-Sat2-L or the short form, which is shown in FIG. 5 as pFMDV-Sat2-S.

FIG. 1 is an FMDV-As1-Shamir-89 version of the generic FMDV DNA vaccine shown in FIG. 17. FIG. 3 is an FMDV-A24cruzeiro DNA version of the generic FMDV DNA vaccine shown in FIG. 17. FIG. 5 is an FMDV-SAT2 DNA version of the generic FMDV DNA vaccine shown in FIG. 17. FIG. 1 shows the schematic representation of the FMDV-As1-Shamir-89 DNA vaccine constructs for Serotype Asia 1, indicating that an As1 Shamir89 insert is clones into a BamH1 and Xho-1 sites. The FMDV-A24cruzeiro DNA vaccine construct shown in FIG. 3 is clones BamH1 and Xho-1 sites. The FMDV-SAT DNA vaccine construct shown in FIG. 5 is clones BamH1 and Xho-1 sites. In each of FIGS. 1, 3 and 5, the plasmid map is based upon the plasmid pVAX. Examples of the FMDV-As1-Shamir insert may be the long form, which is shown in FIG. 1 as pFMDV-As1 Shamir-89-L or the short form, which is shown in FIG. 1 as pFMDV-As1 Shamir-89-S. Examples of the FMDV-A24cruzeiro insert may be the long form, which is shown in FIG. 3 as pFMDV-A24cruzeiro-L or the short form, which is shown in FIG. 3 as pFMDV-A24cruzeiro-S. Examples of the FMDV-SAT2 insert may be the long form, which is shown in FIG. 5 as pFMDV-As1 Sat2 long form or the short form, which is shown in FIG. 5 as pFMDV-Sat2 short form.

Figure 6:
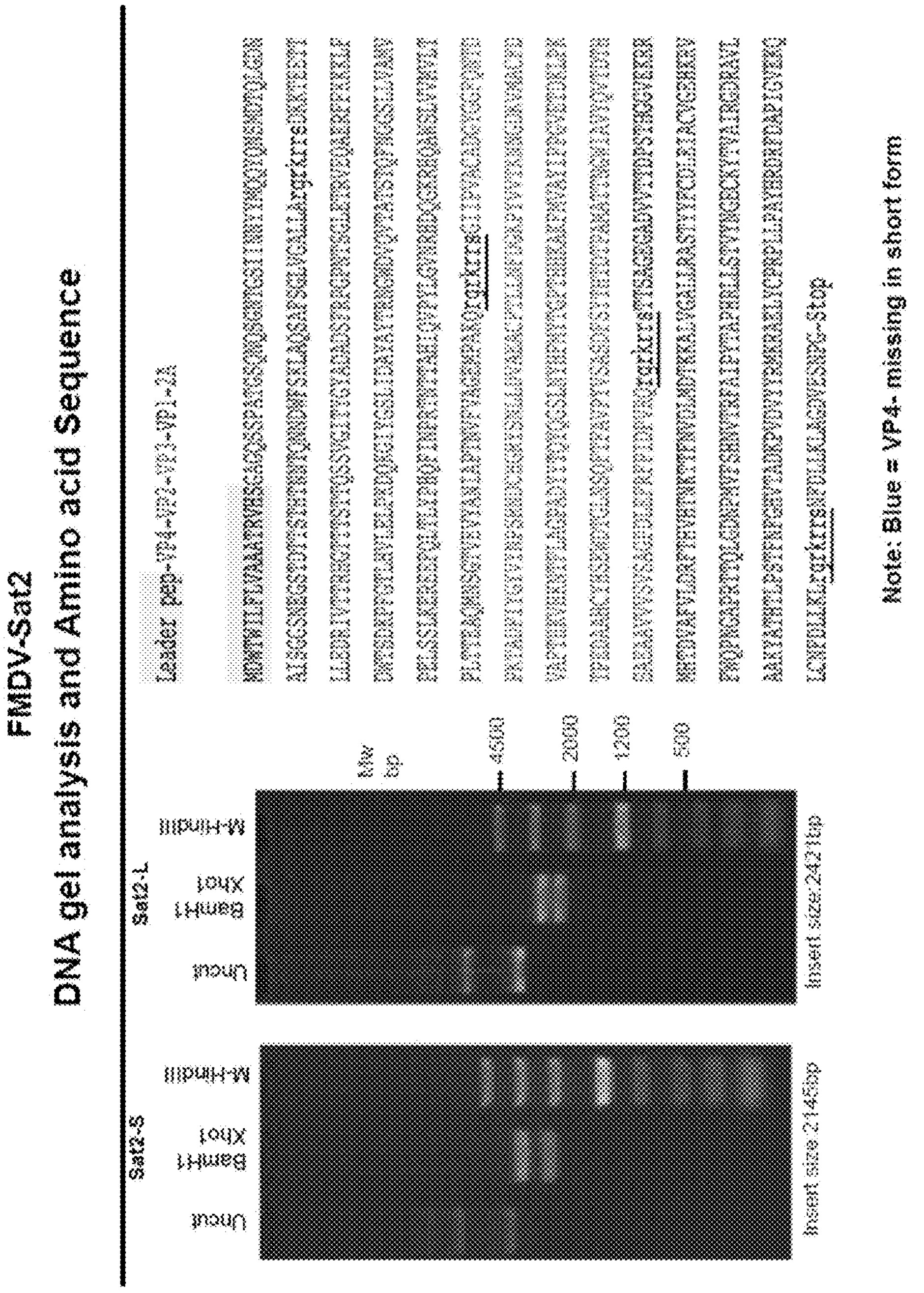
FIG. 6 shows a pair of stained gels showing cloning of Sat2-S (left—SEQ ID NO:11) and Sat2-L (right—SEQ ID NO:9) and the amino acid sequence for FMDV-Sat2-L long form (SEQ ID NO:10 is a FMDV-Sat2-L long form sequence). The sequence included the IgE leader sequence at the N terminus shaded, the proteolytic cleavage sites in lower case and the VP4 sequences is shown between the IgE leader and first proteolytic cleavage site. The VP1 sequence shown between the third and fourth proteolytic cleavage site and a 2a sequence between the last (fourth) proteolytic cleavage site and stop.

FIG. 2 shows a pair of stained gels showing cloning of As1-Shamir89-S (left—SEQ ID NO:7) and As1-Shamir89-L (right—SEQ ID NO:5); FIG. 4 shows a pair of stained gels showing cloning of A24cruzeiro-S (left—SEQ ID NO:3) and A24cruzeiro-L (right—SEQ ID NO:1). FIG. 6 shows a pair of stained gels showing cloning of Sat2-S (left—SEQ ID NO:11) and Sat2-L (right—SEQ ID NO:9). These data show that the inserts have been properly incorporated into the respective plasmids. FIG. 2 shows the amino acid sequence for FMDV-As1-Shamir89-L long form. FIG. 4 shows the amino acid sequence for FMDV-A24cruzeiro-L long form. FIG. 6 shows the amino acid sequence for FMDV-Sat2 long form. In each long form, the sequence included the IgE leader sequence at the N terminus shaded, the proteolytic cleavage sites in lower case and the VP4 sequences in bold type between the IgE leader and first proteolytic cleavage site. Between the first proteolytic cleavage site and the second proteolytic cleavage site is the coding sequence of VP2. Between the second proteolytic cleavage site and the third proteolytic cleavage site is the coding sequence of VP3. Between the third proteolytic cleavage site and the fourth proteolytic cleavage site is the coding sequence of VP1. The 2A sequence between the last (fourth) proteolytic cleavage site and stop.

FIG. 7 shows experimental results of protein expression. Western blots of protein on SDS gels compared protein expression from samples produced by FMDV-A24cruzeiro-S short form, FMDV-A24cruzeiro-L long form, pVAX, FMDV-As1-Shamir89-S short form and FMDV-As1-Shamir89-L long form The blot was probed with anti-A24 antisera.

Figure 8:
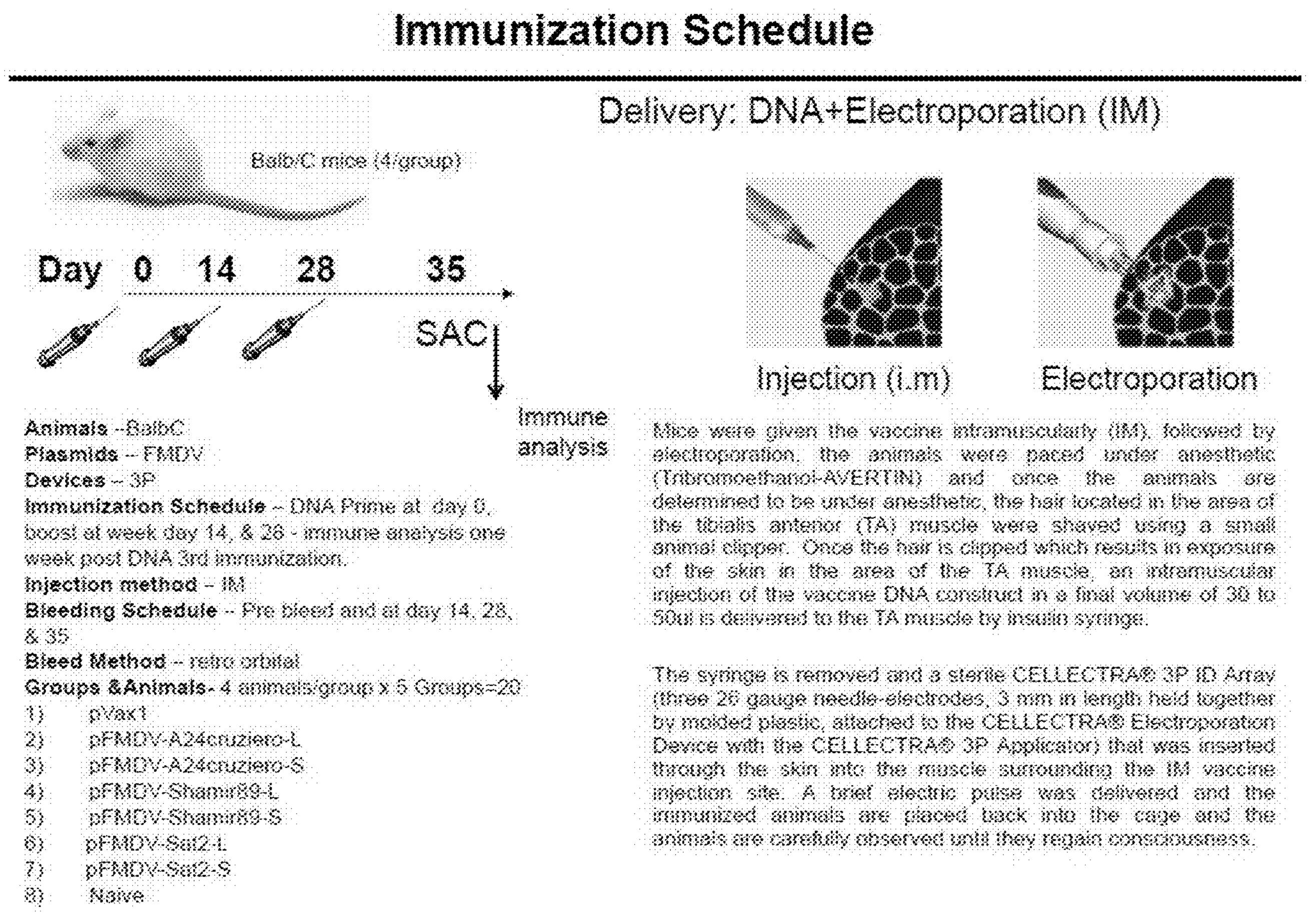
FIG. 8 shows an experimental protocol of immunization experiments using electroporation to evaluate immune responses following administration of 1) pVAX, 2) FMDV-A24cruzeiro-L, 3) FMDV-A24cruzeiro-S, 4) FMDV-Shamir89-L, 5) FMDV-Shamir89-S, FMDV-Sat2-L, FMDV-Sat2-S versus naïve.

FIG. 8 shows an experimental protocol of immunization experiments using electroporation to evaluate immune responses following administration of 1) pVAX, 2) FMDV-A24cruzeiro-L, 3) FMDV-A24cruzeiro-S, 4) FMDV-Shamir89-L, 5) FMDV-Shamir89-S, FMDV-Sat2-L, FMDV-Sat2-S versus naïve.

Figure 9:
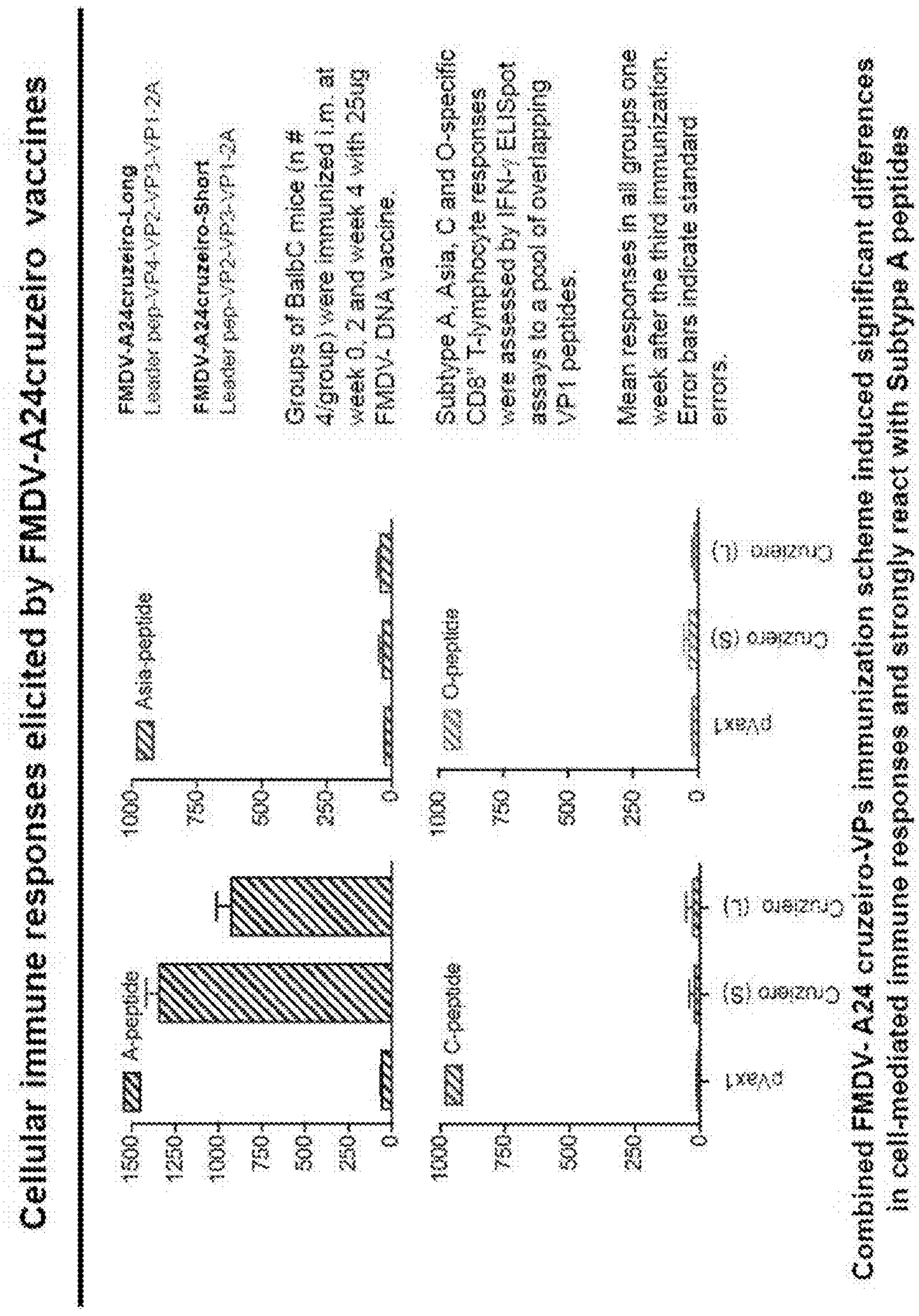
FIG. 9 shows data of cellular immune responses elicited by FMDV-A24cruzeiro-L and FMDV-A24cruzeiro-S vaccines.
Figure 12:
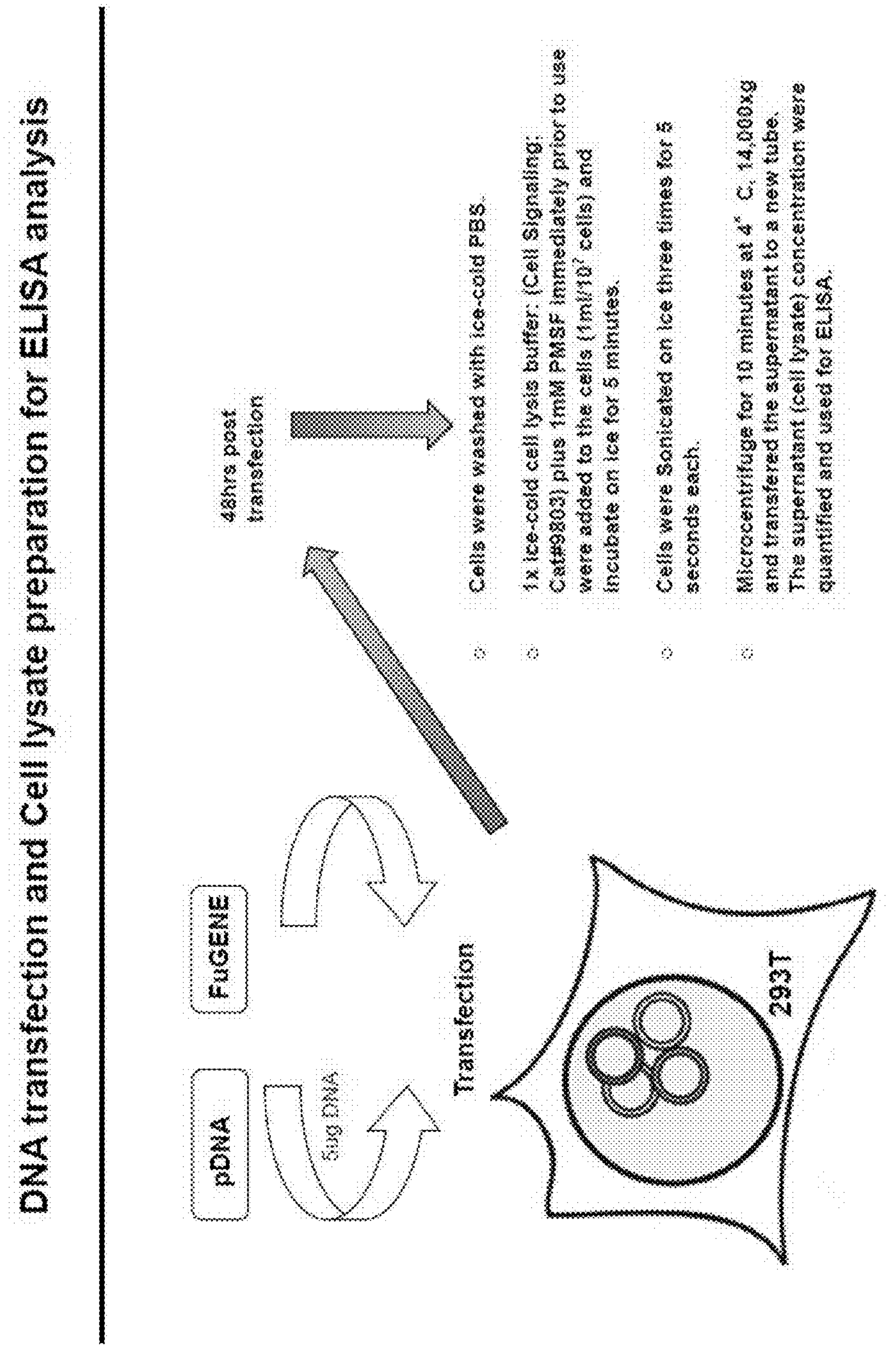
FIG. 12 shows an experimental protocol for DNA transfection and cell lysate preparation for ELISA analysis.
Figure 13:
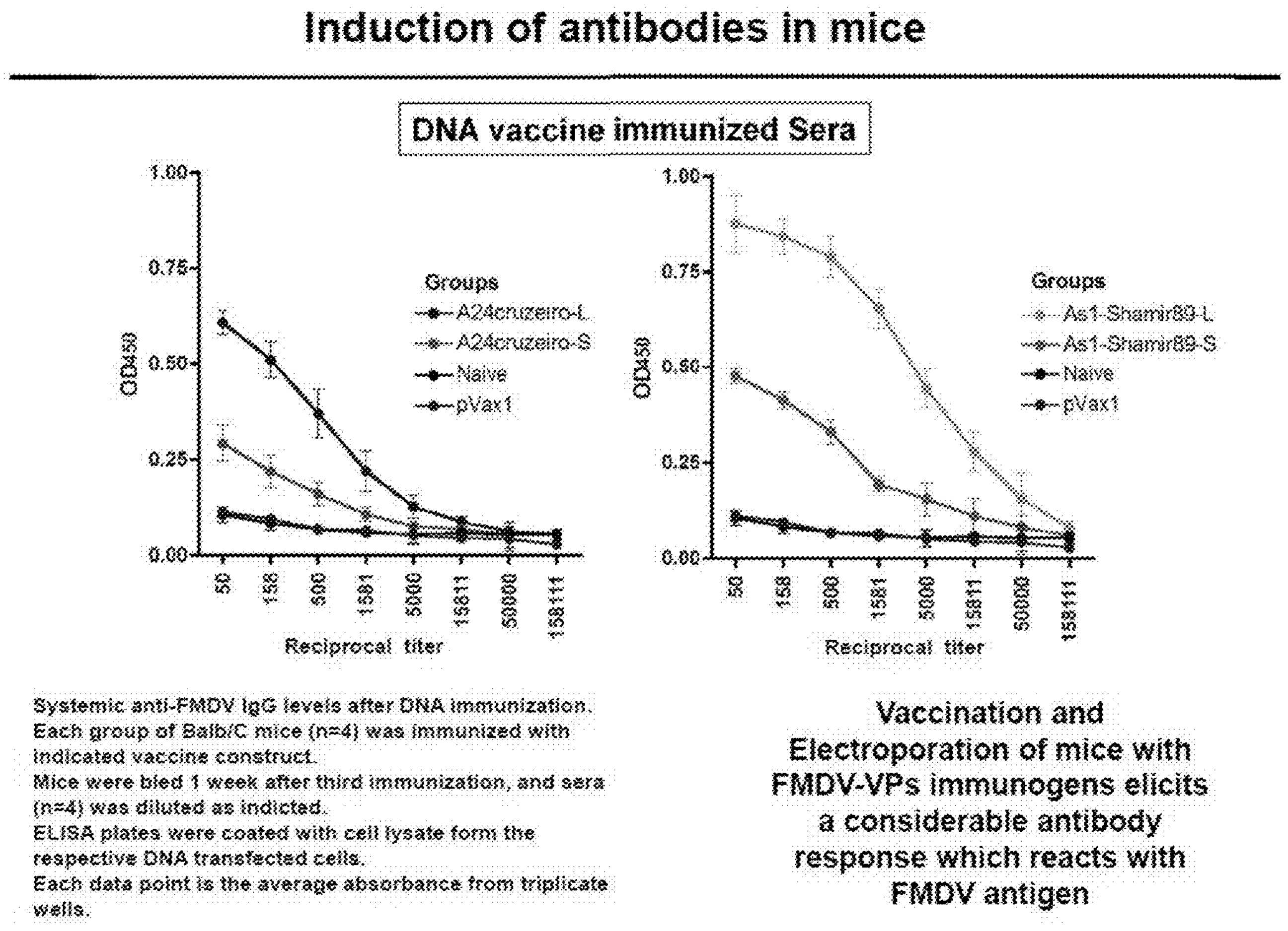
FIG. 13 shows data of antibody induction in mice elicited by FMDV-A24cruzeiro-L and FMDV-A24cruzeiro-S vaccines and by FMDV-As1-Sharma89-L and FMDV-As1-Sharma89-S vaccines.

FIG. 9 shows data of cellular immune responses elicited by FMDV-A24cruzeiro-L and FMDV-A24cruzeiro-S vaccines. FIG. 10 shows data of cellular immune responses elicited by FMDV-As1-Sharma89-L and FMDV-As1-Sharma89-S vaccines. FIG. 11 shows data of cellular immune responses elicited by FMDV-Sat2-L and FMDV-Sat2-S vaccines. FIG. 12 shows an experimental protocol for DNA transfection and cell lysate preparation for ELISA analysis. FIG. 13 shows data of antibody induction in mice elicited by FMDV-A24cruzeiro-L and FMDV-A24cruzeiro-S vaccines and by FMDV-As1-Sharma89-L and FMDV-As1-Sharma89-S vaccines. FIG. 14 shows data of ELISA analysis of antibody binding using protein lysates prepared from FMDV-A24cruzeiro-L transfected cells and FMDV-As1-Sharma89-L transfected cells. The FMDV vaccine were immunogenic in mice. Seroconversion was observed in all immunized animals. Long forms of the vaccines were more potent than short forms. Humoral responses appear most potent against the Shamir vaccine as compared to the Creuzeiro vaccine, however, both vaccines were potent. Cellular responses were more cross-reactive with the Shamir vaccine as compared to the Creuzeiro vaccine. Comparison with Bovine seropositive sera shows reasonable levels of immune reactivity was induced by the vaccines.

FIG. 15 shows amino acid sequence comparisons between sharir and cruzeiro sequences. Shamir VP4 sequences (SEQ ID NO:17) are shown compared cruzeiro VP4 sequences (SEQ ID NO:18); Shamir VP2 sequences (SEQ ID NO:19) are shown compared cruzeiro VP2 sequences (SEQ ID NO:20); and Shamir 2A sequences (SEQ ID NO:21) are shown compared cruzeiro 2A (SEQ ID NO:22).

Figure 16:
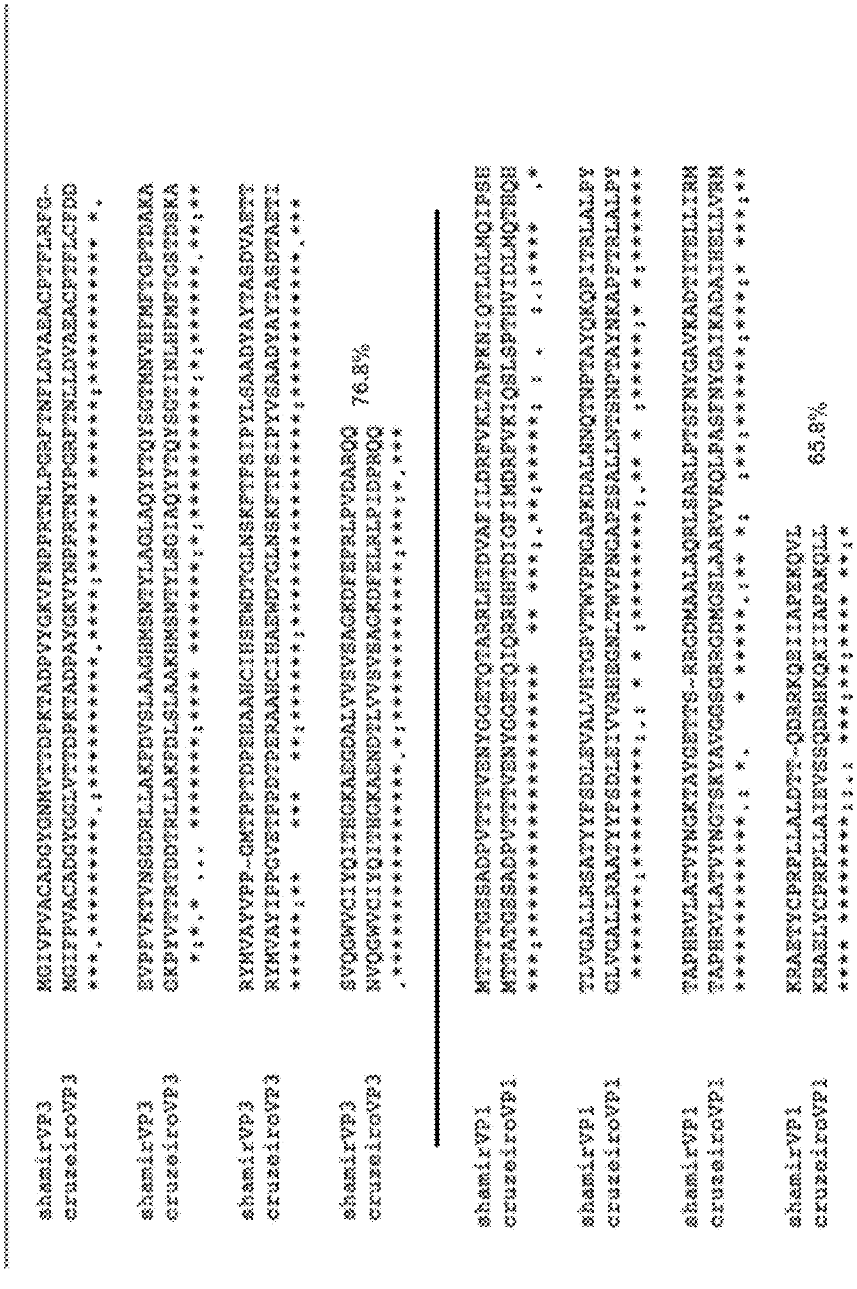
FIG. 16 shows amino acid sequence comparisons between sharir and cruzeiro sequences. Shamir VP3 sequences (SEQ ID NO:23) are shown compared cruzeiro VP3 sequences (SEQ ID NO:24); and Shamir VP1 sequences (SEQ ID NO:25) are shown compared cruzeiro VP1 sequences (SEQ ID NO:26).

FIG. 16 shows amino acid sequence comparisons between sharir and cruzeiro sequences. Shamir VP3 sequences (SEQ ID NO:23) are shown compared cruzeiro VP3 sequences (SEQ ID NO:24); and Shamir VP1 sequences (SEQ ID NO:25) are shown compared cruzeiro VP1 sequences (SEQ ID NO:26).

Example 2

Fourteen constructs have been designed for preparing an FMDV vaccine. Sequences from seven foot-and-mouth disease virus subtypes, A, Asia 1, C, O, SAT1, SAT2, SAT3, SAT4, are used. Two construct designs may be used—a long version and a short version. Accordingly there are long and short forms of constructs for each of subtypes, A, Asia 1, C, O, SAT1, SAT2, SAT3, SAT4, yielding 14 constructs. Vaccines may be produced using as few as 4 constructs, and typically 7.

A generic long form is shown in FIG. 17. Immunogen coding sequences are arranged in the order VP4, VP2, VP3, VP1. Coding sequences for protease cleavage sites separate each of the four viral proteins. Coding sequence may be provided for any optional IgE leader sequences provided. Likewise a FMDV peptide 2A tail is provided at the end including a protease cleavage site.

A generic short form is also shown in FIG. 17. Immunogen coding sequences are arranged in the order VP2, VP3, VP1. Coding sequences for protease cleavage sites separate each of the four viral proteins. Coding sequence may be provided for any optional IgE leader sequences provided. Likewise a 16 amino acid 2A tail is provided at the end including a protease cleavage site.

Constructs are inserted into plasmid expression vectors resulting in 14 plasmids.

In some embodiments, vaccines comprise A-long form, Asia 1-long, C-long form, O-long form, SAT1-long form, SAT2-long form, SAT3-long form, and SAT4-long form.

In some embodiments, vaccines comprise A-short form, Asia 1-short, C-short form, O-short form, SAT1-short form, SAT2-short form, SAT3-short form, and SAT4-short form.

In some embodiments, vaccines comprise A-long form, Asia 1-long, C-long form, and O-long form.

In some embodiments, vaccines comprise A-short form, Asia 1-short, C-short form, and O-short form.

The N terminus may be a leader sequence, such as IgE or IgG, or no leader.

The individual viral proteins are to be separated from each other by a protease which is commonly present in the cells where expression is desired.

WO 2011/054011 discloses FMDV vaccines. Included in the disclosure are amino acid sequences and coding sequences for the 28 sequences which can be included in various embodiments. The fourteen viral sequences are: VP1, VP2, VP3, and VP4 for each of FMDV subtypes A, Asia 1, O, C, SAT1, SAT2, and SAT3. The sequences disclosed therein may be used to generate constructs which can be included in vaccines.

Constructs include a long form and a short form. FIG. 1 shows a partially generic form of each. As shown in FIG. 17, in the present invention, constructs provide viral proteins VP1, VP2, VP3, and VP4 in a specific order: VP4-VP2-VP3-VP1. An optional tail, 2A is also provided. The constructs have an optional IgE leader sequence. When expressed, a proteolytic cleavage site "CS" is provided between each of VP4, VP2, VP3, VP1 and when present 2A. The protease which can process the site may be furin in some embodiments. Other protease sites may be used. The site must be recognized by a protease commonly found in cells where the vaccine is expressed.

In one aspect of the present invention, there are fusion proteins comprising consensus FMDV proteins VP1, VP2, VP3, VP4 and/or 3C and nucleic acid sequences encoding these proteins, which can be generated and used in a vaccine to provide protection of mammals against foot-and-mouth disease across one or more subtypes of FMDV, including A, Asia 1, O, C, SAT1, SAT2, and SAT3.

In another aspect of the present invention, there are fusion proteins comprising consensus FMDV proteins VP1 and nucleic acid sequences encoding these proteins, from two different subtypes which can be generated and used in a vaccine to provide protection of mammals against foot-and-mouth disease across one or more subtypes of FMDV, including A, Asia 1, O, C, SAT1, SAT2, and SAT3.

In another aspect of the present invention, there are consensus FMDV proteins VP1 and nucleic acid sequences encoding them which can be generated and used in a vaccine to provide protection of mammals against foot-and-mouth disease across one or more subtypes of FMDV, including A, Asia 1, O, C, SAT1, SAT2, and SAT3.

The invention claimed is:

1. A nucleic acid molecule comprising a nucleic acid sequence selected from the group consisting of SEQ ID NO:1, SEQ ID NO:3, SEQ ID NO:5, SEQ ID NO:7, SEQ ID NO:9, and SEQ ID NO:11.

2. A plasmid comprising a nucleic acid molecule of claim 1.

3. A vaccine comprising one or more plasmids of claim 2.

4. A nucleic acid molecule comprising one or more sequences selected from the groups consisting of:

a) a fragment of a sequence selected from the group consisting of an FMDV VP1 protein coding sequence, VP2 protein coding sequence, VP3 protein coding sequence and VP4 protein coding sequence, wherein the fragment comprises at least 70% of the length of the FMDV VP1 protein coding sequence, VP2 protein coding sequence, VP3 protein coding sequence or VP4 protein coding sequence;

b) a sequence at least 90% homologous to a sequence selected from the group consisting of an FMDV VP1 protein coding sequence, VP2 protein coding sequence, VP3 protein coding sequence and VP4 protein coding sequence; and c) a fragment of a sequence at least 90% homologous to a sequence selected from the group consisting of an FMDV VP1 protein coding sequence, VP2 protein coding sequence, VP3 protein coding sequence and VP4 protein coding sequence, wherein the fragment comprises at least 70% of the length of the sequence at least 90% homologous to a FMDV VP1 protein coding sequence, VP2 protein coding sequence, VP3 protein coding sequence or VP4 protein coding sequence;

wherein the FMDV VP1 protein coding sequence is the FMDV VP1 protein coding sequence in one selected from the group consisting of SEQ ID NO:1, SEQ ID NO:3, SEQ ID NO:5, SEQ ID NO:7, SEQ ID NO:9, and SEQ ID NO:11;

wherein the FMDV VP2 protein coding sequence is the FMDV VP2 protein coding sequence in one selected from the group consisting of SEQ ID NO:1, SEQ ID NO:3, SEQ ID NO:5, SEQ ID NO:7, SEQ ID NO:9, and SEQ ID NO:11;

wherein the FMDV VP3 protein coding sequence is the FMDV VP3 protein coding sequence in one selected from the group consisting of SEQ ID NO:1, SEQ ID NO:3, SEQ ID NO:5, SEQ ID NO:7, SEQ ID NO:9, and SEQ ID NO:11;

wherein the FMDV VP4 protein coding sequence is the FMDV VP4 protein coding sequence in one selected from the group consisting of SEQ ID NO:1, SEQ ID NO:5, and SEQ ID NO:9.

5. The nucleic acid molecule of claim 4, wherein the sequence is selected from the group consisting of an FMDV VP1 protein coding sequence, VP2 protein coding sequence, VP3 protein coding sequence and VP4 protein coding sequence.

6. The nucleic acid molecule of claim 4, wherein the fragment comprises at least 80% of the length of a sequence selected from the group consisting of an FMDV VP1 protein coding sequence, VP2 protein coding sequence, VP3 protein coding sequence and VP4 protein coding sequence; or wherein the fragment comprises at least 80% of the length of a sequence at least 90% homologous to a sequence selected from the group consisting of an FMDV VP1 protein coding sequence, VP2 protein coding sequence, VP3 protein coding sequence and VP4 protein coding sequence.

7. The nucleic acid molecule of claim 4, wherein the fragment comprises at least 90% of the length of a sequence selected from the group consisting of an FMDV VP1 protein coding sequence, VP2 protein coding sequence, VP3 protein coding sequence and VP4 protein coding sequence; or wherein the fragment comprises at least 90% of the length of a sequence at least 90% homologous to a sequence selected from the group consisting of an FMDV VP1 protein coding sequence, VP2 protein coding sequence, VP3 protein coding sequence and VP4 protein coding sequence.

8. The nucleic acid molecule of claim 4, wherein the fragment comprises at least 95% of the length of a sequence selected from the group consisting of an FMDV VP1 protein coding sequence, VP2 protein coding sequence, VP3 protein coding sequence and VP4 protein coding sequence; or wherein the fragment comprises at least 95% of the length of a sequence at least 90% homologous to a sequence selected from the group consisting of an FMDV VP1 protein coding sequence, VP2 protein coding sequence, VP3 protein coding sequence and VP4 protein coding sequence.

9. The nucleic acid molecule of claim 4, wherein the sequence is at least 95% homologous to a sequence selected from the group consisting of an FMDV VP1 protein coding sequence, VP2 protein coding sequence, VP3 protein coding sequence and VP4 protein coding sequence.

10. The nucleic acid molecule of claim 4, wherein the sequence is at least 98% homologous to a sequence selected from the group consisting of an FMDV VP1 protein coding sequence, VP2 protein coding sequence, VP3 protein coding sequence and VP4 protein coding sequence.

* * * * *

SEQUENCE LISTING

```
<160> NUMBER OF SEQ ID NOS: 29

<210> SEQ ID NO 1
<211> LENGTH: 2421
<212> TYPE: DNA
<213> ORGANISM: Artificial Sequence
<220> FEATURE:
<223> OTHER INFORMATION: FMDV-A24cruzeiro-Long nucleic acid

<400> SEQUENCE: 1

ggatccgcca ccatggattg gacatggatt ctgttcctgg tggctgctgc tactagagtg      60

cattcagggg ccggacagtc ttcacccgca accggatcac agaaccagag tggaaatacc     120

gggagcatca ttaacaatta ctatatgcag cagtaccaga acagcatgga cacacagctg     180

ggggataacg ccatcagcgg cggcagcaat gagggctcca cagataccac atctactcac     240

actaccaata cccagaacaa tgactggttc tctaaactgg caagctccgc cttcaccggc     300

ctctttggag ctctgctcgc aaggggaaga aagaggagaa gcgataagaa aacagaggaa     360

accaccctgc tggaggacag aatcctgacc acaagaaacg ggcacactac cagcacaact     420

cagtcttcag tgggcgtcac acacggatac tcaactgagg aagaccatgt ggccgggcca     480

aataccagtg gcctggagac acgagtggtc caggctgaaa ggttctacaa gaaatatctg     540

tttgactgga ccacagataa ggccttcggc cacctggaga aactggaact cccctcagac     600

caccacggcg tgttcggcca tctggtcgat agctacgcct atatgagaaa cggatgggac     660

gtggaggtct ccgctgtggg caaccagttc aatggcggat gcctgctcgt ggctatggtg     720

cccgagtgga aggaatttga taccagggaa aaataccagc tgacactctt cccacaccag     780

tttatctctc ctagaactaa catgaccgcc catattaccg tgccttatct gggcgtcaat     840

cggtacgacc agtataagaa acacaaacct tggaccctgg tggtcatggt ggtcagtccc     900

ctcacagtga acaatactag cgccgctcag atcaaggtct acgccaacat tgctccaacc     960

tatgtgcacg tcgcaggaga gctgccttcc aaggaacggg gacgcaaacg gcgctctggg    1020
```

-continued

```
atcttcccag tggcatgtgc tgacggatac ggagggctgg tcactaccga ccctaagacc   1080

gcagatcccg cctacggaaa agtgtataac ccacccagga ctaattaccc agggcggttc   1140

accaacctgc tcgatgtggc agaggcctgc cccaccttcc tgtgctttga cgatggcaag   1200

ccatacgtga caactcggac agacgatact cgcctgctcg ccaagtttga cctgagcctc   1260

gcagccaaac acatgtcaaa cacctacctg agtggaatcg cccagtacta tactcagtat   1320

tccgggacca ttaatctgca tttcatgttt accggctcta cagactcaaa ggctcgctac   1380

atggtggcat atatccctcc cggcgtcgag accccacctg atacacctga aagggctgca   1440

cactgcatcc atgccgagtg ggacacagga ctgaacagca agttcacttt ttccattccc   1500

tacgtgtctg ccgctgacta cgcttatacc gcatccgata ctgccgaaac cattaacgtg   1560

cagggatggg tctgtatcta ccagattact cacgggaaag ccgagaatga caccctggtg   1620

gtctccgtgt ctgctggcaa ggacttcgaa ctgcgcctcc ctatcgatcc ccgacagcag   1680

cgaggcagga agcgaaggag caccacagcc accggagagt ccgctgaccc tgtgactacc   1740

acagtcgaga actacggcgg agaaacacag attcagagac ggcaccatac tgacatcgga   1800

ttcattatgg atagatttgt gaagatccag tcactgagtc ccacccacgt gattgatctc   1860

atgcagacac accagcatgg actggtgggg gccctgctcc gagcagcaac ctactacttc   1920

agcgacctgg agatcgtggt ccgccatgaa ggcaacctga catgggtgcc aaatggagcc   1980

cctgagtcag ctctgctcaa cactagtaat cccaccgcat acaacaaagc cccgttcacc   2040

cggctggcac tcccctatac agccccacac cgcgtgctgg ccacagtcta caatggcact   2100

tctaagtatg ctgtgggcgg cagcggcagg aggggcgaca tggggtccct cgctgcacgg   2160

gtggtcaagc agctgccagc ttctttcaac tacggagcaa tcaaagctga cgcaattcac   2220

gagctgctcg tgcgcatgaa gcgagcagaa ctgtattgcc ccaggccact gctcgctatc   2280

gaggtgagta gccaggacag acataagcag aaaatcattg cccccgctaa gcagctgctc   2340

agaggccgga agagacgatc taattttgac ctgctcaagc tcgccggaga cgtggaatct   2400

aatcctggat gataactcga g                                             2421
```

```
<210> SEQ ID NO 2
<211> LENGTH: 799
<212> TYPE: PRT
<213> ORGANISM: Artificial Sequence
<220> FEATURE:
<223> OTHER INFORMATION: A24cruzeiro-Long amino acid

<400> SEQUENCE: 2

Met Asp Trp Thr Trp Ile Leu Phe Leu Val Ala Ala Ala Thr Arg Val
1               5                   10                  15

His Ser Gly Ala Gly Gln Ser Ser Pro Ala Thr Gly Ser Gln Asn Gln
            20                  25                  30

Ser Gly Asn Thr Gly Ser Ile Ile Asn Asn Tyr Tyr Met Gln Gln Tyr
        35                  40                  45

Gln Asn Ser Met Asp Thr Gln Leu Gly Asp Asn Ala Ile Ser Gly Gly
    50                  55                  60

Ser Asn Glu Gly Ser Thr Asp Thr Thr Ser Thr His Thr Thr Asn Thr
65                  70                  75                  80

Gln Asn Asn Asp Trp Phe Ser Lys Leu Ala Ser Ser Ala Phe Thr Gly
                85                  90                  95

Leu Phe Gly Ala Leu Leu Ala Arg Gly Arg Lys Arg Arg Ser Asp Lys
            100                 105                 110
```

-continued

```
Lys Thr Glu Glu Thr Thr Leu Leu Glu Asp Arg Ile Leu Thr Thr Arg
        115                 120                 125

Asn Gly His Thr Thr Ser Thr Thr Gln Ser Ser Val Gly Val Thr His
    130                 135                 140

Gly Tyr Ser Thr Glu Glu Asp His Val Ala Gly Pro Asn Thr Ser Gly
145                 150                 155                 160

Leu Glu Thr Arg Val Val Gln Ala Glu Arg Phe Tyr Lys Lys Tyr Leu
                165                 170                 175

Phe Asp Trp Thr Thr Asp Lys Ala Phe Gly His Leu Glu Lys Leu Glu
            180                 185                 190

Leu Pro Ser Asp His His Gly Val Phe Gly His Leu Val Asp Ser Tyr
        195                 200                 205

Ala Tyr Met Arg Asn Gly Trp Asp Val Glu Val Ser Ala Val Gly Asn
    210                 215                 220

Gln Phe Asn Gly Gly Cys Leu Leu Val Ala Met Val Pro Glu Trp Lys
225                 230                 235                 240

Glu Phe Asp Thr Arg Glu Lys Tyr Gln Leu Thr Leu Phe Pro His Gln
                245                 250                 255

Phe Ile Ser Pro Arg Thr Asn Met Thr Ala His Ile Thr Val Pro Tyr
            260                 265                 270

Leu Gly Val Asn Arg Tyr Asp Gln Tyr Lys Lys His Lys Pro Trp Thr
        275                 280                 285

Leu Val Val Met Val Val Ser Pro Leu Thr Val Asn Asn Thr Ser Ala
    290                 295                 300

Ala Gln Ile Lys Val Tyr Ala Asn Ile Ala Pro Thr Tyr Val His Val
305                 310                 315                 320

Ala Gly Glu Leu Pro Ser Lys Glu Arg Gly Arg Lys Arg Arg Ser Gly
                325                 330                 335

Ile Phe Pro Val Ala Cys Ala Asp Gly Tyr Gly Gly Leu Val Thr Thr
            340                 345                 350

Asp Pro Lys Thr Ala Asp Pro Ala Tyr Gly Lys Val Tyr Asn Pro Pro
        355                 360                 365

Arg Thr Asn Tyr Pro Gly Arg Phe Thr Asn Leu Leu Asp Val Ala Glu
    370                 375                 380

Ala Cys Pro Thr Phe Leu Cys Phe Asp Asp Gly Lys Pro Tyr Val Thr
385                 390                 395                 400

Thr Arg Thr Asp Asp Thr Arg Leu Leu Ala Lys Phe Asp Leu Ser Leu
                405                 410                 415

Ala Ala Lys His Met Ser Asn Thr Tyr Leu Ser Gly Ile Ala Gln Tyr
            420                 425                 430

Tyr Thr Gln Tyr Ser Gly Thr Ile Asn Leu His Phe Met Phe Thr Gly
        435                 440                 445

Ser Thr Asp Ser Lys Ala Arg Tyr Met Val Ala Tyr Ile Pro Pro Gly
    450                 455                 460

Val Glu Thr Pro Pro Asp Thr Pro Glu Arg Ala Ala His Cys Ile His
465                 470                 475                 480

Ala Glu Trp Asp Thr Gly Leu Asn Ser Lys Phe Thr Phe Ser Ile Pro
                485                 490                 495

Tyr Val Ser Ala Ala Asp Tyr Ala Tyr Thr Ala Ser Asp Thr Ala Glu
            500                 505                 510

Thr Ile Asn Val Gln Gly Trp Val Cys Ile Tyr Gln Ile Thr His Gly
        515                 520                 525

Lys Ala Glu Asn Asp Thr Leu Val Val Ser Val Ser Ala Gly Lys Asp
```

```
    530                 535                 540

Phe Glu Leu Arg Leu Pro Ile Asp Pro Arg Gln Gln Arg Gly Arg Lys
545                 550                 555                 560

Arg Arg Ser Thr Thr Ala Thr Gly Glu Ser Ala Asp Pro Val Thr Thr
                565                 570                 575

Thr Val Glu Asn Tyr Gly Gly Glu Thr Gln Ile Gln Arg Arg His His
            580                 585                 590

Thr Asp Ile Gly Phe Ile Met Asp Arg Phe Val Lys Ile Gln Ser Leu
        595                 600                 605

Ser Pro Thr His Val Ile Asp Leu Met Gln Thr His Gln His Gly Leu
    610                 615                 620

Val Gly Ala Leu Leu Arg Ala Ala Thr Tyr Tyr Phe Ser Asp Leu Glu
625                 630                 635                 640

Ile Val Val Arg His Glu Gly Asn Leu Thr Trp Val Pro Asn Gly Ala
                645                 650                 655

Pro Glu Ser Ala Leu Leu Asn Thr Ser Asn Pro Thr Ala Tyr Asn Lys
            660                 665                 670

Ala Pro Phe Thr Arg Leu Ala Leu Pro Tyr Thr Ala Pro His Arg Val
        675                 680                 685

Leu Ala Thr Val Tyr Asn Gly Thr Ser Lys Tyr Ala Val Gly Gly Ser
    690                 695                 700

Gly Arg Arg Gly Asp Met Gly Ser Leu Ala Ala Arg Val Val Lys Gln
705                 710                 715                 720

Leu Pro Ala Ser Phe Asn Tyr Gly Ala Ile Lys Ala Asp Ala Ile His
                725                 730                 735

Glu Leu Leu Val Arg Met Lys Arg Ala Glu Leu Tyr Cys Pro Arg Pro
            740                 745                 750

Leu Leu Ala Ile Glu Val Ser Ser Gln Asp Arg His Lys Gln Lys Ile
        755                 760                 765

Ile Ala Pro Ala Lys Gln Leu Leu Arg Gly Arg Lys Arg Arg Ser Asn
    770                 775                 780

Phe Asp Leu Leu Lys Leu Ala Gly Asp Val Glu Ser Asn Pro Gly
785                 790                 795


<210> SEQ ID NO 3
<211> LENGTH: 2145
<212> TYPE: DNA
<213> ORGANISM: Artificial Sequence
<220> FEATURE:
<223> OTHER INFORMATION: A24cruzeiro-Short nucleic acid

<400> SEQUENCE: 3

ggatccgcca ccatggactg gacctggatt ctgttcctcg tcgccgccgc aacacgggtg      60

cattcagaca aaaagaccga agagactaca ctcctggagg atagaatcct gaccacacgg     120

aacggccaca ctacctccac aactcagagc tccgtgggcg tcacacacgg atacagcact     180

gaggaagacc atgtggccgg gccaaatacc tccggcctgg agacaagggt ggtccaggct     240

gaaagattct acaagaagta tctcttcgac tggaccacag ataaggcctt cggacacctg     300

gagaaactgg aactcccctc tgaccaccac ggcgtgttcg gccatctggt cgattcatac     360

gcctatatga ggaacggatg ggacgtggag gtctccgctg tgggcaacca gttcaatggc     420

ggatgcctgc tcgtggctat ggtgcccgag tggaaggaat ttgataccag ggaaaaatac     480

cagctgacac tcttcccaca ccagtttatc tctcctagaa ctaacatgac cgcccatatt     540

acagtgcctt atctgggcgt caatcggtac gaccagtata agaaacacaa accttggacc     600
```

```
ctggtggtca tggtggtgag ccccctgaca gtgaacaata cttctgccgc tcagatcaag    660

gtctacgcaa acattgcccc aacctatgtg cacgtcgccg gcgagctgcc ttcaaaggaa    720

cgcggacgaa aaaggagaag tggatcttc ccagtggcat gtgctgacgg atacggcgga    780

ctggtcacta ccgaccctaa gaccgctgat cccgcatacg ggaaagtgta taacccaccc    840

aggactaatt acccaggccg cttcaccaat ctgctcgatg tggcagaggc ctgccccacc    900

ttcctgtgct ttgacgatgg caagccatac gtgacaactc gcacagacga tactcgactg    960

ctcgccaagt ttgacctgag cctcgcagcc aaacacatga gcaacaccta cctgtccgga   1020

atcgcccagt actatactca gtatagcggg accattaatc tgcatttcat gtttaccggc   1080

tcaacagaca gtaaagcccg ctacatggtg gcttatatcc ctcccggagt cgagacccca   1140

cctgatacac ctgaaagggc tgcacactgc atccatgccg agtgggacac agggctgaac   1200

tctaagttca ctttttcaat tccctacgtg agtgccgctg actacgccta taccgccagc   1260

gatactgccg agaccatcaa cgtgcaggga tgggtctgta tctaccagat tactcacggg   1320

aaagccgaga atgacaccct ggtggtgagc gtgagcgccg gaaaggactt cgaactgcga   1380

ctccctatcg atccaaggca gcagaggggc agaaagcggc gctctaccac agcaaccgga   1440

gagtcagccg accctgtgac taccacagtc gagaactacg gaggggaaac acagattcag   1500

cgaaggcacc ataccgacat cgggttcatt atggatagat ttgtgaagat ccagtccctg   1560

tctcccacac acgtgattga tctcatgcag acccaccagc atggactggt gggggccctg   1620

ctccgagcag caacatacta cttcagcgac ctggagatcg tggtccgcca tgaaggcaac   1680

ctgacctggg tgccaaatgg agcacctgag agcgccctgc tcaacacttc caatcccacc   1740

gcttacaaca aagcaccctt caccagactg gctctcccct atacagcacc acaccgggtg   1800

ctggcaacag tctacaatgg gactagtaag tatgcagtgg gcggaagcgg cagacgggga   1860

gatatggggt ccctcgctgc acgggtggtc aagcagctgc cagcctcttt caactacggc   1920

gctatcaaag ctgacgcaat tcacgagctg ctcgtgcgaa tgaagagggc tgaactgtat   1980

tgcccccgcc cactgctcgc aatcgaggtg tcttcacagg accgacataa gcagaaaatc   2040

attgcccccg ctaagcagct gctcaggggc aggaaaagac gcagtaattt cgacctcctc   2100

aagctcgcag gcgacgtgga atctaacccc ggctgataac tcgag                   2145
```

```
<210> SEQ ID NO 4
<211> LENGTH: 707
<212> TYPE: PRT
<213> ORGANISM: Artificial Sequence
<220> FEATURE:
<223> OTHER INFORMATION: A24cruzeiro-Short amino acid

<400> SEQUENCE: 4

Met Asp Trp Thr Trp Ile Leu Phe Leu Val Ala Ala Ala Thr Arg Val
1               5                   10                  15

His Ser Asp Lys Lys Thr Glu Glu Thr Thr Leu Leu Glu Asp Arg Ile
            20                  25                  30

Leu Thr Thr Arg Asn Gly His Thr Thr Ser Thr Thr Gln Ser Ser Val
        35                  40                  45

Gly Val Thr His Gly Tyr Ser Thr Glu Glu Asp His Val Ala Gly Pro
    50                  55                  60

Asn Thr Ser Gly Leu Glu Thr Arg Val Val Gln Ala Glu Arg Phe Tyr
65                  70                  75                  80

Lys Lys Tyr Leu Phe Asp Trp Thr Thr Asp Lys Ala Phe Gly His Leu
```

-continued

```
                85                  90                  95

Glu Lys Leu Glu Leu Pro Ser Asp His His Gly Val Phe Gly His Leu
            100                 105                 110

Val Asp Ser Tyr Ala Tyr Met Arg Asn Gly Trp Asp Val Glu Val Ser
        115                 120                 125

Ala Val Gly Asn Gln Phe Asn Gly Gly Cys Leu Leu Val Ala Met Val
    130                 135                 140

Pro Glu Trp Lys Glu Phe Asp Thr Arg Glu Lys Tyr Gln Leu Thr Leu
145                 150                 155                 160

Phe Pro His Gln Phe Ile Ser Pro Arg Thr Asn Met Thr Ala His Ile
                165                 170                 175

Thr Val Pro Tyr Leu Gly Val Asn Arg Tyr Asp Gln Tyr Lys Lys His
            180                 185                 190

Lys Pro Trp Thr Leu Val Val Met Val Val Ser Pro Leu Thr Val Asn
        195                 200                 205

Asn Thr Ser Ala Ala Gln Ile Lys Val Tyr Ala Asn Ile Ala Pro Thr
    210                 215                 220

Tyr Val His Val Ala Gly Glu Leu Pro Ser Lys Glu Arg Gly Arg Lys
225                 230                 235                 240

Arg Arg Ser Gly Ile Phe Pro Val Ala Cys Ala Asp Gly Tyr Gly Gly
                245                 250                 255

Leu Val Thr Thr Asp Pro Lys Thr Ala Asp Pro Ala Tyr Gly Lys Val
            260                 265                 270

Tyr Asn Pro Pro Arg Thr Asn Tyr Pro Gly Arg Phe Thr Asn Leu Leu
        275                 280                 285

Asp Val Ala Glu Ala Cys Pro Thr Phe Leu Cys Phe Asp Asp Gly Lys
    290                 295                 300

Pro Tyr Val Thr Thr Arg Thr Asp Asp Thr Arg Leu Leu Ala Lys Phe
305                 310                 315                 320

Asp Leu Ser Leu Ala Ala Lys His Met Ser Asn Thr Tyr Leu Ser Gly
                325                 330                 335

Ile Ala Gln Tyr Tyr Thr Gln Tyr Ser Gly Thr Ile Asn Leu His Phe
            340                 345                 350

Met Phe Thr Gly Ser Thr Asp Ser Lys Ala Arg Tyr Met Val Ala Tyr
        355                 360                 365

Ile Pro Pro Gly Val Glu Thr Pro Pro Asp Thr Pro Glu Arg Ala Ala
    370                 375                 380

His Cys Ile His Ala Glu Trp Asp Thr Gly Leu Asn Ser Lys Phe Thr
385                 390                 395                 400

Phe Ser Ile Pro Tyr Val Ser Ala Ala Asp Tyr Ala Tyr Thr Ala Ser
                405                 410                 415

Asp Thr Ala Glu Thr Ile Asn Val Gln Gly Trp Val Cys Ile Tyr Gln
            420                 425                 430

Ile Thr His Gly Lys Ala Glu Asn Asp Thr Leu Val Val Ser Val Ser
        435                 440                 445

Ala Gly Lys Asp Phe Glu Leu Arg Leu Pro Ile Asp Pro Arg Gln Gln
    450                 455                 460

Arg Gly Arg Lys Arg Arg Ser Thr Thr Ala Thr Gly Glu Ser Ala Asp
465                 470                 475                 480

Pro Val Thr Thr Thr Val Glu Asn Tyr Gly Gly Glu Thr Gln Ile Gln
                485                 490                 495

Arg Arg His His Thr Asp Ile Gly Phe Ile Met Asp Arg Phe Val Lys
            500                 505                 510
```

```
Ile Gln Ser Leu Ser Pro Thr His Val Ile Asp Leu Met Gln Thr His
        515                 520                 525

Gln His Gly Leu Val Gly Ala Leu Leu Arg Ala Ala Thr Tyr Tyr Phe
    530                 535                 540

Ser Asp Leu Glu Ile Val Val Arg His Glu Gly Asn Leu Thr Trp Val
545                 550                 555                 560

Pro Asn Gly Ala Pro Glu Ser Ala Leu Leu Asn Thr Ser Asn Pro Thr
                565                 570                 575

Ala Tyr Asn Lys Ala Pro Phe Thr Arg Leu Ala Leu Pro Tyr Thr Ala
            580                 585                 590

Pro His Arg Val Leu Ala Thr Val Tyr Asn Gly Thr Ser Lys Tyr Ala
        595                 600                 605

Val Gly Gly Ser Gly Arg Arg Gly Asp Met Gly Ser Leu Ala Ala Arg
    610                 615                 620

Val Val Lys Gln Leu Pro Ala Ser Phe Asn Tyr Gly Ala Ile Lys Ala
625                 630                 635                 640

Asp Ala Ile His Glu Leu Leu Val Arg Met Lys Arg Ala Glu Leu Tyr
                645                 650                 655

Cys Pro Arg Pro Leu Leu Ala Ile Glu Val Ser Ser Gln Asp Arg His
            660                 665                 670

Lys Gln Lys Ile Ile Ala Pro Ala Lys Gln Leu Leu Arg Gly Arg Lys
        675                 680                 685

Arg Arg Ser Asn Phe Asp Leu Leu Lys Leu Ala Gly Asp Val Glu Ser
    690                 695                 700

Asn Pro Gly
705


<210> SEQ ID NO 5
<211> LENGTH: 2409
<212> TYPE: DNA
<213> ORGANISM: Artificial Sequence
<220> FEATURE:
<223> OTHER INFORMATION: As1-Shamir-89-Long nucleic acid

<400> SEQUENCE: 5

ggatccgcca ccatggattg gacatggatt ctgttcctgg tcgccgccgc aacacgggtg      60

cattctgggg ccggacagtc ttcacctgct actgggagcc agaaccagag cggaaataca     120

gggtccatca ttaacaatta ctatatgcag cagtaccaga acagcatgga cacccagctg     180

ggcgataacg ccatctccgg cggatctaat gagggatcta ctgacaccac atcaacacac     240

actaacaata cccagaacaa tgattggttc agtagactcg ccagctccgc tttctctgga     300

ctgtttggag cactgctcgc ccggggccgc aagaggagat ccgacaagaa aaccgaggaa     360

accaccctgc tggaggatcg aatcctgaca actaggaacg gacataccac aagcactacc     420

cagtcttcag tgggagtcac ctacgggtat gctgtcgcag aagacgccgt gagtgggccc     480

aacacaagcg gcctggagac tagagtgcag caggctgaac ggttctttaa gaaacacctc     540

ttcgattgga cacctaatct ggcctttggc cattgctact atctggagct ccccaccgaa     600

cacaaggggg tgtacggctc actgatgggg agttacgcat atatgcggaa cggatgggac     660

atcgaggtga ccgcagtcgg aaaccagttc aatggcggat gtctgctcgt ggctctggtc     720

cctgagctga aggaactcga tacaaggcag aaataccagc tgactctctt ccctcatcag     780

tttattaacc ccagaacaaa tatgactgcc cacatcaacg tgccctacgt cggcattaat     840

cggtacgacc agtatgccct ccataagcct tggaccctgg tggtcatggt ggtcgctccc     900
```

```
ctgaccgtga agacaggagg gtccgagcag atcaaagtgt acatgaacgc cgctccaacc    960

tatgtgcacg tcgccggcga gctgccttca aaggaacgag gcaggaaacg gcgctctgga   1020

attgtgccag tcgcatgcgc tgacggatac ggaaacatgg tgacaactga ccccaagacc   1080

gccgatccag tctatggaaa agtgttcaac ccacccagga ccaatctccc tgggcgattc   1140

acaaactttc tggatgtggc agaggcctgt cccacattcc tgcggtttgg ggaagtgcca   1200

ttcgtcaaga ccgtgaacag cggcgaccga ctgctcgcca aatttgacgt gagcctggcc   1260

gccggccaca tgagtaacac ctacctggct ggactcgcac agtactatac ccagtatagc   1320

gggacaatga atgtgcactt catgtttact ggcccaaccg acgctaaggc aagatacatg   1380

gtcgcctatg tgcctcccgg gatgacacca cctactgacc ctgagcacgc tgcacattgc   1440

atccacagcg aatgggatac tggcctcaac tccaaattca ccttttctat tccctacctg   1500

tcagccgctg actacgccta tacagccagc gatgtggccg agaccacatc cgtccaggga   1560

tgggtgtgca tctaccagat tacccacggc aaggctgagg gagacgcact ggtggtgagc   1620

gtgagcgccg ggaaagactt cgaatttcgg ctgcccgtgg atgcacgcca gcagagagga   1680

cggaagcgaa ggtctactac cacaactggg gaatcagccg acccagtcac cacaactgtg   1740

gagaactacg gcggagaaac ccagacagca agacggctgc acaccgacgt ggccttcatc   1800

ctcgatcgct ttgtgaagct gacagccccc aaaaatatcc agactctgga cctcatgcag   1860

attccatccc atacactggt gggcgcactg ctcaggagtg ccacttacta tttcagcgac   1920

ctggaggtcg ctctcgtgca cactggacca gtcacctggg tgcctaacgg agcaccaaag   1980

gatgctctga acaatcagac caatccaaca gcctaccaga aacagcctat caccaggctg   2040

gctctcccat atacagcacc tcacagagtc ctggctaccg tgtacaacgg aaagaccgcc   2100

tacggcgaga ccacaagccg ccgaggcgac atggcagccc tggcccagcg gctctccgct   2160

cgcctgccca catctttcaa ttacggagca gtgaaggccg atactatcac cgagctgctc   2220

attaggatga aaagagccga aacctattgc cccaggccac tgctcgctct ggacactacc   2280

caggatagga gaaagcagga gatcattgcc ccagaaaaac aggtgctgcg cggccgaaaa   2340

agacggagta atttcgacct gctcaagctc gctggcgatg tggaaagtaa tcccggatga   2400

taactcgag                                                           2409
```

<210> SEQ ID NO 6
<211> LENGTH: 795
<212> TYPE: PRT
<213> ORGANISM: Artificial Sequence
<220> FEATURE:
<223> OTHER INFORMATION: As1-Shamir-89-Long amino acid

<400> SEQUENCE: 6

```
Met Asp Trp Thr Trp Ile Leu Phe Leu Val Ala Ala Ala Thr Arg Val
1               5                   10                  15

His Ser Gly Ala Gly Gln Ser Ser Pro Ala Thr Gly Ser Gln Asn Gln
            20                  25                  30

Ser Gly Asn Thr Gly Ser Ile Ile Asn Asn Tyr Tyr Met Gln Gln Tyr
        35                  40                  45

Gln Asn Ser Met Asp Thr Gln Leu Gly Asp Asn Ala Ile Ser Gly Gly
    50                  55                  60

Ser Asn Glu Gly Ser Thr Asp Thr Thr Ser Thr His Thr Asn Asn Thr
65                  70                  75                  80

Gln Asn Asn Asp Trp Phe Ser Arg Leu Ala Ser Ser Ala Phe Ser Gly
```

-continued

```
                85                  90                  95

Leu Phe Gly Ala Leu Leu Ala Arg Gly Arg Lys Arg Arg Ser Asp Lys
            100                 105                 110

Lys Thr Glu Glu Thr Thr Leu Leu Glu Asp Arg Ile Leu Thr Thr Arg
        115                 120                 125

Asn Gly His Thr Thr Ser Thr Thr Gln Ser Ser Val Gly Val Thr Tyr
    130                 135                 140

Gly Tyr Ala Val Ala Glu Asp Ala Val Ser Gly Pro Asn Thr Ser Gly
145                 150                 155                 160

Leu Glu Thr Arg Val Gln Gln Ala Glu Arg Phe Phe Lys Lys His Leu
                165                 170                 175

Phe Asp Trp Thr Pro Asn Leu Ala Phe Gly His Cys Tyr Tyr Leu Glu
            180                 185                 190

Leu Pro Thr Glu His Lys Gly Val Tyr Gly Ser Leu Met Gly Ser Tyr
        195                 200                 205

Ala Tyr Met Arg Asn Gly Trp Asp Ile Glu Val Thr Ala Val Gly Asn
    210                 215                 220

Gln Phe Asn Gly Gly Cys Leu Leu Val Ala Leu Val Pro Glu Leu Lys
225                 230                 235                 240

Glu Leu Asp Thr Arg Gln Lys Tyr Gln Leu Thr Leu Phe Pro His Gln
                245                 250                 255

Phe Ile Asn Pro Arg Thr Asn Met Thr Ala His Ile Asn Val Pro Tyr
            260                 265                 270

Val Gly Ile Asn Arg Tyr Asp Gln Tyr Ala Leu His Lys Pro Trp Thr
        275                 280                 285

Leu Val Val Met Val Val Ala Pro Leu Thr Val Lys Thr Gly Gly Ser
    290                 295                 300

Glu Gln Ile Lys Val Tyr Met Asn Ala Ala Pro Thr Tyr Val His Val
305                 310                 315                 320

Ala Gly Glu Leu Pro Ser Lys Glu Arg Gly Arg Lys Arg Arg Ser Gly
                325                 330                 335

Ile Val Pro Val Ala Cys Ala Asp Gly Tyr Gly Asn Met Val Thr Thr
            340                 345                 350

Asp Pro Lys Thr Ala Asp Pro Val Tyr Gly Lys Val Phe Asn Pro Pro
        355                 360                 365

Arg Thr Asn Leu Pro Gly Arg Phe Thr Asn Phe Leu Asp Val Ala Glu
    370                 375                 380

Ala Cys Pro Thr Phe Leu Arg Phe Gly Glu Val Pro Phe Val Lys Thr
385                 390                 395                 400

Val Asn Ser Gly Asp Arg Leu Leu Ala Lys Phe Asp Val Ser Leu Ala
                405                 410                 415

Ala Gly His Met Ser Asn Thr Tyr Leu Ala Gly Leu Ala Gln Tyr Tyr
            420                 425                 430

Thr Gln Tyr Ser Gly Thr Met Asn Val His Phe Met Phe Thr Gly Pro
        435                 440                 445

Thr Asp Ala Lys Ala Arg Tyr Met Val Ala Tyr Val Pro Pro Gly Met
    450                 455                 460

Thr Pro Pro Thr Asp Pro Glu His Ala Ala His Cys Ile His Ser Glu
465                 470                 475                 480

Trp Asp Thr Gly Leu Asn Ser Lys Phe Thr Phe Ser Ile Pro Tyr Leu
                485                 490                 495

Ser Ala Ala Asp Tyr Ala Tyr Thr Ala Ser Asp Val Ala Glu Thr Thr
            500                 505                 510
```

-continued

Ser Val Gln Gly Trp Val Cys Ile Tyr Gln Ile Thr His Gly Lys Ala
515 520 525

Glu Gly Asp Ala Leu Val Val Ser Val Ser Ala Gly Lys Asp Phe Glu
530 535 540

Phe Arg Leu Pro Val Asp Ala Arg Gln Gln Arg Gly Arg Lys Arg Arg
545 550 555 560

Ser Thr Thr Thr Thr Gly Glu Ser Ala Asp Pro Val Thr Thr Thr Val
565 570 575

Glu Asn Tyr Gly Gly Glu Thr Gln Thr Ala Arg Arg Leu His Thr Asp
580 585 590

Val Ala Phe Ile Leu Asp Arg Phe Val Lys Leu Thr Ala Pro Lys Asn
595 600 605

Ile Gln Thr Leu Asp Leu Met Gln Ile Pro Ser His Thr Leu Val Gly
610 615 620

Ala Leu Leu Arg Ser Ala Thr Tyr Tyr Phe Ser Asp Leu Glu Val Ala
625 630 635 640

Leu Val His Thr Gly Pro Val Thr Trp Val Pro Asn Gly Ala Pro Lys
645 650 655

Asp Ala Leu Asn Asn Gln Thr Asn Pro Thr Ala Tyr Gln Lys Gln Pro
660 665 670

Ile Thr Arg Leu Ala Leu Pro Tyr Thr Ala Pro His Arg Val Leu Ala
675 680 685

Thr Val Tyr Asn Gly Lys Thr Ala Tyr Gly Glu Thr Thr Ser Arg Arg
690 695 700

Gly Asp Met Ala Ala Leu Ala Gln Arg Leu Ser Ala Arg Leu Pro Thr
705 710 715 720

Ser Phe Asn Tyr Gly Ala Val Lys Ala Asp Thr Ile Thr Glu Leu Leu
725 730 735

Ile Arg Met Lys Arg Ala Glu Thr Tyr Cys Pro Arg Pro Leu Leu Ala
740 745 750

Leu Asp Thr Thr Gln Asp Arg Arg Lys Gln Glu Ile Ile Ala Pro Glu
755 760 765

Lys Gln Val Leu Arg Gly Arg Lys Arg Arg Ser Asn Phe Asp Leu Leu
770 775 780

Lys Leu Ala Gly Asp Val Glu Ser Asn Pro Gly
785 790 795

<210> SEQ ID NO 7
<211> LENGTH: 2133
<212> TYPE: DNA
<213> ORGANISM: Artificial Sequence
<220> FEATURE:
<223> OTHER INFORMATION: As1-Shamir-89-Short nucleic acid

<400> SEQUENCE: 7
ggatccgcca ccatggactg gacctggatt ctgttcctgg tggccgccgc aactcgcgtg 60
cattcagata aaaagaccga agagactaca ctcctggaag acagaatcct gaccacaaga 120
aacggccata ctaccagcac aactcagagc tccgtgggag tcacctacgg gtatgctgtc 180
gcagaggacg ccgtgtccgg accaaacaca tctggcctgg agactcgggt gcagcaggct 240
gaacgcttct ttaagaaaca cctcttcgat tggacaccta atctggcctt tggacattgc 300
tactatctgg agctccccac cgaacacaag gggtgtacg gcagtctgat ggggagctac 360
gcttatatga gaaacggctg ggacatcgag gtgaccgcag tcgggaacca gttcaatggc 420

-continued

```
ggatgtctgc tcgtggctct ggtccctgag ctgaaggaac tcgatacaag gcagaaatac    480

cagctgactc tcttccctca tcagtttatt aaccccagaa caaatatgac tgcccacatc    540

aacgtgccct acgtcggcat taatcggtac gaccagtatg cactccataa gccttggaca    600

ctggtggtca tggtggtcgc tcccctgacc gtgaagacag gggctccga gcagatcaaa    660

gtgtacatga acgccgctcc aacctatgtg cacgtcgccg gagagctgcc ttccaaggaa    720

aggggcagaa aaaggaggag cggaattgtg ccagtcgcct gcgctgacgg ctacggaaac    780

atggtgacca cagaccccaa gaccgccgat ccagtctatg ggaaagtgtt caacccaccc    840

aggaccaatc tccctggcag gttcacaaac tttctggatg tggcagaggc ctgtcccaca    900

ttcctgcggt ttggcgaagt gccattcgtc aagaccgtga acagcggaga ccgcctgctc    960

gccaaatttg atgtgagcct ggcagccggc cacatgtcca acacctacct ggccggactc   1020

gctcagtact atacccagta tagcgggaca atgaatgtgc acttcatgtt tactggccca   1080

accgacgcta aggcacggta catggtcgcc tatgtgcctc ccggcatgac accacctact   1140

gaccctgagc acgctgcaca ttgcatccac agcgaatggg atactggact caactcaaaa   1200

ttcaccttta gtattcccta cctgagcgcc gctgactacg catatacagc ctctgatgtg   1260

gccgagacta cctcagtcca ggggtgggtg tgcatctacc agattaccca cggcaaggca   1320

gagggagacg ctctcgtggt gagcgtgagc gccggcaaag acttcgagtt caggctgcca   1380

gtggatgctc gacagcagcg gggacgcaag cggcgcagta caactaccac aggggaaagc   1440

gccgatccag tcactaccac agtggagaac tacggagggg aaacccagac agctcgaagg   1500

ctgcacaccg acgtggcatt catcctcgat cgctttgtga agctgacagc cccaaaaat   1560

atccagactc tggacctcat gcagattcca tcccatactc tggtgggcgc tctgctcagg   1620

tccgcaacct actatttctc tgacctggag gtcgctctcg tgcacactgg accagtcacc   1680

tgggtgccta acggagcacc aaaggatgcc ctgaacaatc agaccaatcc aacagcctac   1740

cagaaacagc ctatcacccg cctggccctc ccatatacag ctcctcaccg agtcctggcc   1800

accgtgtaca acggaaagac cgcttatggg gagaccacca gcaggagggg cgacatggca   1860

gccctggcac agcgcctctc agcccgactg cccacaagtt tcaattacgg ggctgtgaag   1920

gcagatacta tcaccgagct gctcattaga atgaaacggg cagaaaccta ttgccccagg   1980

ccactgctcg ccctggacac aactcaggat cgccgaaagc aggagatcat tgccccagaa   2040

aaacaggtgc tgcgaggcag gaaaagacgc agtaatttcg acctcctcaa gctcgcaggc   2100

gacgtggaat ctaatcccgg atgataactc gag                                 2133
```

<210> SEQ ID NO 8
<211> LENGTH: 703
<212> TYPE: PRT
<213> ORGANISM: Artificial Sequence
<220> FEATURE:
<223> OTHER INFORMATION: As1-Shamir-89-Short amino acid

<400> SEQUENCE: 8

```
Met Asp Trp Thr Trp Ile Leu Phe Leu Val Ala Ala Ala Thr Arg Val
1               5                   10                  15

His Ser Asp Lys Lys Thr Glu Glu Thr Thr Leu Leu Glu Asp Arg Ile
            20                  25                  30

Leu Thr Thr Arg Asn Gly His Thr Thr Ser Thr Thr Gln Ser Ser Val
        35                  40                  45

Gly Val Thr Tyr Gly Tyr Ala Val Ala Glu Asp Ala Val Ser Gly Pro
    50                  55                  60
```

```
Asn Thr Ser Gly Leu Glu Thr Arg Val Gln Gln Ala Glu Arg Phe Phe
65                  70                  75                  80

Lys Lys His Leu Phe Asp Trp Thr Pro Asn Leu Ala Phe Gly His Cys
                85                  90                  95

Tyr Tyr Leu Glu Leu Pro Thr Glu His Lys Gly Val Tyr Gly Ser Leu
            100                 105                 110

Met Gly Ser Tyr Ala Tyr Met Arg Asn Gly Trp Asp Ile Glu Val Thr
        115                 120                 125

Ala Val Gly Asn Gln Phe Asn Gly Gly Cys Leu Leu Val Ala Leu Val
    130                 135                 140

Pro Glu Leu Lys Glu Leu Asp Thr Arg Gln Lys Tyr Gln Leu Thr Leu
145                 150                 155                 160

Phe Pro His Gln Phe Ile Asn Pro Arg Thr Asn Met Thr Ala His Ile
                165                 170                 175

Asn Val Pro Tyr Val Gly Ile Asn Arg Tyr Asp Gln Tyr Ala Leu His
            180                 185                 190

Lys Pro Trp Thr Leu Val Val Met Val Val Ala Pro Leu Thr Val Lys
        195                 200                 205

Thr Gly Gly Ser Glu Gln Ile Lys Val Tyr Met Asn Ala Ala Pro Thr
    210                 215                 220

Tyr Val His Val Ala Gly Glu Leu Pro Ser Lys Glu Arg Gly Arg Lys
225                 230                 235                 240

Arg Arg Ser Gly Ile Val Pro Val Ala Cys Ala Asp Gly Tyr Gly Asn
                245                 250                 255

Met Val Thr Thr Asp Pro Lys Thr Ala Asp Pro Val Tyr Gly Lys Val
            260                 265                 270

Phe Asn Pro Pro Arg Thr Asn Leu Pro Gly Arg Phe Thr Asn Phe Leu
        275                 280                 285

Asp Val Ala Glu Ala Cys Pro Thr Phe Leu Arg Phe Gly Glu Val Pro
    290                 295                 300

Phe Val Lys Thr Val Asn Ser Gly Asp Arg Leu Leu Ala Lys Phe Asp
305                 310                 315                 320

Val Ser Leu Ala Ala Gly His Met Ser Asn Thr Tyr Leu Ala Gly Leu
                325                 330                 335

Ala Gln Tyr Tyr Thr Gln Tyr Ser Gly Thr Met Asn Val His Phe Met
            340                 345                 350

Phe Thr Gly Pro Thr Asp Ala Lys Ala Arg Tyr Met Val Ala Tyr Val
        355                 360                 365

Pro Pro Gly Met Thr Pro Pro Thr Asp Pro Glu His Ala Ala His Cys
    370                 375                 380

Ile His Ser Glu Trp Asp Thr Gly Leu Asn Ser Lys Phe Thr Phe Ser
385                 390                 395                 400

Ile Pro Tyr Leu Ser Ala Ala Asp Tyr Ala Tyr Thr Ala Ser Asp Val
                405                 410                 415

Ala Glu Thr Thr Ser Val Gln Gly Trp Val Cys Ile Tyr Gln Ile Thr
            420                 425                 430

His Gly Lys Ala Glu Gly Asp Ala Leu Val Val Ser Val Ser Ala Gly
        435                 440                 445

Lys Asp Phe Glu Phe Arg Leu Pro Val Asp Ala Arg Gln Gln Arg Gly
    450                 455                 460

Arg Lys Arg Arg Ser Thr Thr Thr Thr Gly Glu Ser Ala Asp Pro Val
465                 470                 475                 480
```

```
Thr Thr Thr Val Glu Asn Tyr Gly Gly Glu Thr Gln Thr Ala Arg Arg
                485                 490                 495

Leu His Thr Asp Val Ala Phe Ile Leu Asp Arg Phe Val Lys Leu Thr
            500                 505                 510

Ala Pro Lys Asn Ile Gln Thr Leu Asp Leu Met Gln Ile Pro Ser His
        515                 520                 525

Thr Leu Val Gly Ala Leu Leu Arg Ser Ala Thr Tyr Tyr Phe Ser Asp
    530                 535                 540

Leu Glu Val Ala Leu Val His Thr Gly Pro Val Thr Trp Val Pro Asn
545                 550                 555                 560

Gly Ala Pro Lys Asp Ala Leu Asn Asn Gln Thr Asn Pro Thr Ala Tyr
                565                 570                 575

Gln Lys Gln Pro Ile Thr Arg Leu Ala Leu Pro Tyr Thr Ala Pro His
            580                 585                 590

Arg Val Leu Ala Thr Val Tyr Asn Gly Lys Thr Ala Tyr Gly Glu Thr
        595                 600                 605

Thr Ser Arg Arg Gly Asp Met Ala Ala Leu Ala Gln Arg Leu Ser Ala
    610                 615                 620

Arg Leu Pro Thr Ser Phe Asn Tyr Gly Ala Val Lys Ala Asp Thr Ile
625                 630                 635                 640

Thr Glu Leu Leu Ile Arg Met Lys Arg Ala Glu Thr Tyr Cys Pro Arg
                645                 650                 655

Pro Leu Leu Ala Leu Asp Thr Thr Gln Asp Arg Arg Lys Gln Glu Ile
            660                 665                 670

Ile Ala Pro Glu Lys Gln Val Leu Arg Gly Arg Lys Arg Arg Ser Asn
        675                 680                 685

Phe Asp Leu Leu Lys Leu Ala Gly Asp Val Glu Ser Asn Pro Gly
    690                 695                 700
```

```
<210> SEQ ID NO 9
<211> LENGTH: 2421
<212> TYPE: DNA
<213> ORGANISM: Artificial Sequence
<220> FEATURE:
<223> OTHER INFORMATION: Sat2-Long nucleic acid

<400> SEQUENCE: 9

ggatccgcca ccatggattg gacatggatt ctctttctgg tcgccgccgc aacacgggtg     60

cactcagggg ctggacagtc ttcacctgct acaggctctc agaaccagag tggaaatacc    120

gggagcatca ttaacaatta ctatatgcag cagtaccaga actccatgga cacccagctg    180

ggggataacg ccatctcagg cggaagtaat gaaggctcca ctgataccac atctacacac    240

actaacaata cccagaacaa tgactggttc agtaaactgg ctcagagcgc attttccgga    300

ctcgtgggag cactgctcgc taggggaaga aagaggagat cagataagaa aaccgaggaa    360

actaccctgc tggaggacag gatcgtgaca actagacatg gcaccacaac ttctaccaca    420

cagagctccg tcggaattac ctacgggtat gccgacgctg atagcttcag acctggcccc    480

aacacatccg gactggaaac tcgggtggag caggccgaac gcttctttaa gaaaaagctg    540

ttcgactgga cttctgataa gccttttgga accctccacg tgctggagct ccccaaagac    600

cagaagggga tctacggctc actgattgat gcatacgcct atacccgaaa cggatgggac    660

gtccaggtga ccgccacatc aactcagttc aatgggggca gtctgctcgt cgctatggtg    720

cccgagctgt cttcactcaa ggaaagagag gaattccagc tgacactcta tccacaccag    780

tttatcaacc ctcggaccaa tactaccgcc catattcagg tcccttacct gggagtgaac    840
```

```
cgacacgacc aggggaagcg gcatcaggcc tggtcactgg tggtcatggt gctgaccccc    900

ctcacaactg aggctcagat gaatagtgga acagtcgaag tgtacgcaaa catcgcccca    960

accaatgtct tcgtggcagg agagatgcct gcaaaacagc gaggacgaaa gcgacgaagc   1020

ggaatcattc cagtggcttg cgcagacggc tacggagggt ttcagaacac cgaccctaag   1080

acagccgatc ccatctacgg atatgtgtac aaccctagtc gcaatgattg ccacgggagg   1140

tatagcaacc tgctcgacgt ggccgaggct tgtcccacac tgctcaattt cgatggaaag   1200

ccatacgtgg tcaccaaaaa caatggggac aaggtcatgg cttgtttcga tgtggccttc   1260

acccacaaag tccataagaa cacttttctg gctggccccg cagactacta tacccagtac   1320

cagggcagcc tgaactatca cttcatgtac acagggccaa ctcaccataa agccaagttt   1380

atggtggctt atatcccccc aggggtcgag accgacaaac tgcccaagac accagaagat   1440

gccgctcact gctaccattc tgagtgggac accggcctga actcacagtt cacatttgct   1500

gtcccatatg tcagtgcaag cgacttcagc tacacccaca cagatactcc tgcaatggcc   1560

accacaaatg gctggatcgc tgtctaccag gtgaccgaca cacattccgc agaagcagca   1620

gtggtcgtgt ccgtgtctgc tggaccagac ctggagttca gatttcctat tgatcccgtg   1680

cgacagaggg gcagaaagcg aaggtctact acctcagccg gggaaggcgc tgacgtcgtg   1740

acaactgatc catctacaca cggcggagtg gagaaaagac ggatgcatac cgacgtcgcc   1800

ttcgtgctgg atcgctttac tcacgtgcat accaacaaga ccacattcaa tgtcgacctg   1860

atggatacaa aaaaggccct ggtgggagca ctgctcaggg ctagcaccta ctatttctgc   1920

gatctggaga tcgcctgtgt gggagaacac aagagagtct tttggcagcc aaacggagca   1980

cctcgaacta cccagctggg cgacaacccc atggtcttca gccacaatgt gactcgcttt   2040

gcaatcccct ataccgcccc acataggctg ctctccaccg tgtataacgg cgagtgtaaa   2100

tacacagtgg ccattagagg agaccgggct gtcctggctg caaagtacgc cactcacacc   2160

ctccctagca cattcaactt tggccatgtg actgccgaca aacccgtcga tgtgtactat   2220

cgcatgaagc gagctgaact gtattgccca aggcctctgc tcccagcata ccaccgagac   2280

cgcttcgatg ccccaatcgg cgtggagaaa cagctgtgta actttgacct gctcaaactc   2340

cgaggaagga agcgccgatc caacttcgac ctgctcaagc tggccggcga tgtggagtct   2400

aatcccggat gataactcga g                                             2421
```

```
<210> SEQ ID NO 10
<211> LENGTH: 799
<212> TYPE: PRT
<213> ORGANISM: Artificial Sequence
<220> FEATURE:
<223> OTHER INFORMATION: Sat2-Long amino acid

<400> SEQUENCE: 10

Met Asp Trp Thr Trp Ile Leu Phe Leu Val Ala Ala Ala Thr Arg Val
1               5                   10                  15

His Ser Gly Ala Gly Gln Ser Ser Pro Ala Thr Gly Ser Gln Asn Gln
            20                  25                  30

Ser Gly Asn Thr Gly Ser Ile Ile Asn Asn Tyr Tyr Met Gln Gln Tyr
        35                  40                  45

Gln Asn Ser Met Asp Thr Gln Leu Gly Asp Asn Ala Ile Ser Gly Gly
    50                  55                  60

Ser Asn Glu Gly Ser Thr Asp Thr Thr Ser Thr His Thr Asn Asn Thr
65                  70                  75                  80
```

-continued

```
Gln Asn Asn Asp Trp Phe Ser Lys Leu Ala Gln Ser Ala Phe Ser Gly
                85                  90                  95

Leu Val Gly Ala Leu Leu Ala Arg Gly Arg Lys Arg Arg Ser Asp Lys
            100                 105                 110

Lys Thr Glu Glu Thr Thr Leu Leu Glu Asp Arg Ile Val Thr Thr Arg
        115                 120                 125

His Gly Thr Thr Thr Ser Thr Thr Gln Ser Ser Val Gly Ile Thr Tyr
    130                 135                 140

Gly Tyr Ala Asp Ala Asp Ser Phe Arg Pro Gly Pro Asn Thr Ser Gly
145                 150                 155                 160

Leu Glu Thr Arg Val Glu Gln Ala Glu Arg Phe Phe Lys Lys Lys Leu
                165                 170                 175

Phe Asp Trp Thr Ser Asp Lys Pro Phe Gly Thr Leu His Val Leu Glu
            180                 185                 190

Leu Pro Lys Asp Gln Lys Gly Ile Tyr Gly Ser Leu Ile Asp Ala Tyr
        195                 200                 205

Ala Tyr Thr Arg Asn Gly Trp Asp Val Gln Val Thr Ala Thr Ser Thr
    210                 215                 220

Gln Phe Asn Gly Gly Ser Leu Leu Val Ala Met Val Pro Glu Leu Ser
225                 230                 235                 240

Ser Leu Lys Glu Arg Glu Glu Phe Gln Leu Thr Leu Tyr Pro His Gln
                245                 250                 255

Phe Ile Asn Pro Arg Thr Asn Thr Thr Ala His Ile Gln Val Pro Tyr
            260                 265                 270

Leu Gly Val Asn Arg His Asp Gln Gly Lys Arg His Gln Ala Trp Ser
        275                 280                 285

Leu Val Val Met Val Leu Thr Pro Leu Thr Thr Glu Ala Gln Met Asn
    290                 295                 300

Ser Gly Thr Val Glu Val Tyr Ala Asn Ile Ala Pro Thr Asn Val Phe
305                 310                 315                 320

Val Ala Gly Glu Met Pro Ala Lys Gln Arg Gly Arg Lys Arg Arg Ser
                325                 330                 335

Gly Ile Ile Pro Val Ala Cys Ala Asp Gly Tyr Gly Gly Phe Gln Asn
            340                 345                 350

Thr Asp Pro Lys Thr Ala Asp Pro Ile Tyr Gly Tyr Val Tyr Asn Pro
        355                 360                 365

Ser Arg Asn Asp Cys His Gly Arg Tyr Ser Asn Leu Leu Asp Val Ala
    370                 375                 380

Glu Ala Cys Pro Thr Leu Leu Asn Phe Asp Gly Lys Pro Tyr Val Val
385                 390                 395                 400

Thr Lys Asn Asn Gly Asp Lys Val Met Ala Cys Phe Asp Val Ala Phe
                405                 410                 415

Thr His Lys Val His Lys Asn Thr Phe Leu Ala Gly Pro Ala Asp Tyr
            420                 425                 430

Tyr Thr Gln Tyr Gln Gly Ser Leu Asn Tyr His Phe Met Tyr Thr Gly
        435                 440                 445

Pro Thr His His Lys Ala Lys Phe Met Val Ala Tyr Ile Pro Pro Gly
    450                 455                 460

Val Glu Thr Asp Lys Leu Pro Lys Thr Pro Glu Asp Ala Ala His Cys
465                 470                 475                 480

Tyr His Ser Glu Trp Asp Thr Gly Leu Asn Ser Gln Phe Thr Phe Ala
                485                 490                 495
```

```
Val Pro Tyr Val Ser Ala Ser Asp Phe Ser Tyr Thr His Thr Asp Thr
            500                 505                 510

Pro Ala Met Ala Thr Thr Asn Gly Trp Ile Ala Val Tyr Gln Val Thr
        515                 520                 525

Asp Thr His Ser Ala Glu Ala Ala Val Val Val Ser Val Ser Ala Gly
    530                 535                 540

Pro Asp Leu Glu Phe Arg Phe Pro Ile Asp Pro Val Arg Gln Arg Gly
545                 550                 555                 560

Arg Lys Arg Arg Ser Thr Thr Ser Ala Gly Glu Gly Ala Asp Val Val
                565                 570                 575

Thr Thr Asp Pro Ser Thr His Gly Gly Val Glu Lys Arg Arg Met His
            580                 585                 590

Thr Asp Val Ala Phe Val Leu Asp Arg Phe Thr His Val His Thr Asn
        595                 600                 605

Lys Thr Thr Phe Asn Val Asp Leu Met Asp Thr Lys Lys Ala Leu Val
    610                 615                 620

Gly Ala Leu Leu Arg Ala Ser Thr Tyr Tyr Phe Cys Asp Leu Glu Ile
625                 630                 635                 640

Ala Cys Val Gly Glu His Lys Arg Val Phe Trp Gln Pro Asn Gly Ala
                645                 650                 655

Pro Arg Thr Thr Gln Leu Gly Asp Asn Pro Met Val Phe Ser His Asn
            660                 665                 670

Val Thr Arg Phe Ala Ile Pro Tyr Thr Ala Pro His Arg Leu Leu Ser
        675                 680                 685

Thr Val Tyr Asn Gly Glu Cys Lys Tyr Thr Val Ala Ile Arg Gly Asp
    690                 695                 700

Arg Ala Val Leu Ala Ala Lys Tyr Ala Thr His Thr Leu Pro Ser Thr
705                 710                 715                 720

Phe Asn Phe Gly His Val Thr Ala Asp Lys Pro Val Asp Val Tyr Tyr
                725                 730                 735

Arg Met Lys Arg Ala Glu Leu Tyr Cys Pro Arg Pro Leu Leu Pro Ala
            740                 745                 750

Tyr His Arg Asp Arg Phe Asp Ala Pro Ile Gly Val Glu Lys Gln Leu
        755                 760                 765

Cys Asn Phe Asp Leu Leu Lys Leu Arg Gly Arg Lys Arg Arg Ser Asn
    770                 775                 780

Phe Asp Leu Leu Lys Leu Ala Gly Asp Val Glu Ser Asn Pro Gly
785                 790                 795
```

<210> SEQ ID NO 11
<211> LENGTH: 2145
<212> TYPE: DNA
<213> ORGANISM: Artificial Sequence
<220> FEATURE:
<223> OTHER INFORMATION: Sat2-Short nucleic acid

<400> SEQUENCE: 11

```
ggatccgcca ccatggactg gacttggatt ctgttcctgg tggctgccgc aacacgggtg     60

catagcgaca aaaagaccga agagactaca ctgctggagg acagaatcgt gaccacacgg    120

cacggcacta ccacaagcac tacccagagc tccgtgggaa ttacctacgg gtatgccgac    180

gctgattctt tcagacctgg ccccaacaca tcaggactgg aaactcgcgt ggagcaggcc    240

gaacgattct ttaagaaaaa gctgttcgac tggactagtg ataagccttt tgggaccctc    300

cacgtgctgg agctccccaa agaccagaag gggatctacg gctccctgat tgatgcatac    360
```

-continued

```
gcctataccc gaaacggatg ggacgtccag gtgaccgcca caagcactca gttcaatgga    420

ggcagcctgc tcgtcgctat ggtgccagag ctgtcttcac tcaaagaaag agaggaattc    480

cagctgacac tctatccaca ccagtttatc aaccctcgga ccaatacaac tgcccatatt    540

caggtccctt acctgggagt gaacaggcac gaccagggga agagacatca ggcctggagc    600

ctggtggtca tggtgctgac ccccctcacc acagaggctc agatgaattc cgggacagtc    660

gaagtgtacg ctaacatcgc accaaccaat gtcttcgtgg ctggcgagat gcctgcaaaa    720

cagcgcgggc gaaagaggag aagcggcatc attccagtgg cttgcgcaga cggatacggg    780

ggctttcaga acaccgaccc taagacagcc gatcccatct acggctatgt gtacaaccct    840

tcccggaatg attgccacgg ccgctattct aacctgctcg acgtggccga ggcttgtccc    900

acactgctca atttcgatgg aaagccatac gtggtcacca aaaacaatgg ggacaaggtc    960

atggcctgtt tcgatgtggc ttttacacac aaagtccata agaacacttt tctggccggc   1020

cccgctgact actataccca gtaccagggc agcctgaact atcacttcat gtacacaggg   1080

ccaactcacc ataaagcaaa gtttatggtg gcctatatcc ccccaggcgt cgagaccgac   1140

aaactgccca agacaccaga agatgccgct cactgctacc atagtgagtg ggataccgga   1200

ctgaacagcc agttcacatt tgccgtccca tatgtcagtg ctagcgactt ctcttacacc   1260

cacacagata ctcctgcaat ggccactacc aatggctgga tcgccgtcta ccaggtgacc   1320

gacacacatt cagctgaagc agcagtggtc gtgtccgtgt ctgcaggacc agacctggag   1380

ttcaggtttc ctattgatcc cgtgaggcag agaggacgaa agcgacgatc aacaactagt   1440

gcaggcgaag gagccgacgt cgtgaccaca gatccatcca cacacggagg ggtggagaaa   1500

cgaaggatgc ataccgacgt cgccttcgtg ctggatcgct ttactcacgt gcataccaac   1560

aagactacct tcaatgtcga cctgatggat accaaaaagg ctctcgtggg agcactgctc   1620

agggcctcta cctactattt ctgcgatctg gagatcgcct gtgtggggga acacaagcga   1680

gtcttttggc agccaaacgg agcacctcga acaactcagc tgggcgacaa ccccatggtc   1740

ttctctcaca atgtgactcg ctttgctatc ccctataccg caccacatag gctgctctca   1800

acagtgtata acggcgagtg taaatacacc gtggcaattc gaggagaccg agcagtcctg   1860

gctgcaaagt acgccactca caccctccct tccacattca actttggcca tgtgactgcc   1920

gacaaacccg tcgatgtgta ctatcgaatg aagagggctg aactgtattg cccaagacct   1980

ctgctccccg cttaccaccg cgaccgattc gatgcaccaa tcggagtgga gaaacagctg   2040

tgtaactttg acctgctcaa actcaggggg agaaagagac ggtcaaactt cgacctgctc   2100

aagctggccg gcgatgtgga gagtaatccc ggatgataac tcgag                   2145
```

<210> SEQ ID NO 12
<211> LENGTH: 707
<212> TYPE: PRT
<213> ORGANISM: Artificial Sequence
<220> FEATURE:
<223> OTHER INFORMATION: Sat2-Short amino acid

<400> SEQUENCE: 12

```
Met Asp Trp Thr Trp Ile Leu Phe Leu Val Ala Ala Ala Thr Arg Val
1               5                   10                  15

His Ser Asp Lys Lys Thr Glu Glu Thr Thr Leu Leu Glu Asp Arg Ile
            20                  25                  30

Val Thr Thr Arg His Gly Thr Thr Thr Ser Thr Thr Gln Ser Ser Val
        35                  40                  45
```

-continued

```
Gly Ile Thr Tyr Gly Tyr Ala Asp Ala Asp Ser Phe Arg Pro Gly Pro
    50                  55                  60

Asn Thr Ser Gly Leu Glu Thr Arg Val Glu Gln Ala Glu Arg Phe Phe
65                  70                  75                  80

Lys Lys Lys Leu Phe Asp Trp Thr Ser Asp Lys Pro Phe Gly Thr Leu
                85                  90                  95

His Val Leu Glu Leu Pro Lys Asp Gln Lys Gly Ile Tyr Gly Ser Leu
            100                 105                 110

Ile Asp Ala Tyr Ala Tyr Thr Arg Asn Gly Trp Asp Val Gln Val Thr
        115                 120                 125

Ala Thr Ser Thr Gln Phe Asn Gly Gly Ser Leu Leu Val Ala Met Val
    130                 135                 140

Pro Glu Leu Ser Ser Leu Lys Glu Arg Glu Glu Phe Gln Leu Thr Leu
145                 150                 155                 160

Tyr Pro His Gln Phe Ile Asn Pro Arg Thr Asn Thr Thr Ala His Ile
                165                 170                 175

Gln Val Pro Tyr Leu Gly Val Asn Arg His Asp Gln Gly Lys Arg His
            180                 185                 190

Gln Ala Trp Ser Leu Val Val Met Val Leu Thr Pro Leu Thr Thr Glu
        195                 200                 205

Ala Gln Met Asn Ser Gly Thr Val Glu Val Tyr Ala Asn Ile Ala Pro
    210                 215                 220

Thr Asn Val Phe Val Ala Gly Glu Met Pro Ala Lys Gln Arg Gly Arg
225                 230                 235                 240

Lys Arg Arg Ser Gly Ile Ile Pro Val Ala Cys Ala Asp Gly Tyr Gly
                245                 250                 255

Gly Phe Gln Asn Thr Asp Pro Lys Thr Ala Asp Pro Ile Tyr Gly Tyr
            260                 265                 270

Val Tyr Asn Pro Ser Arg Asn Asp Cys His Gly Arg Tyr Ser Asn Leu
        275                 280                 285

Leu Asp Val Ala Glu Ala Cys Pro Thr Leu Leu Asn Phe Asp Gly Lys
    290                 295                 300

Pro Tyr Val Val Thr Lys Asn Asn Gly Asp Lys Val Met Ala Cys Phe
305                 310                 315                 320

Asp Val Ala Phe Thr His Lys Val His Lys Asn Thr Phe Leu Ala Gly
                325                 330                 335

Pro Ala Asp Tyr Tyr Thr Gln Tyr Gln Gly Ser Leu Asn Tyr His Phe
            340                 345                 350

Met Tyr Thr Gly Pro Thr His His Lys Ala Lys Phe Met Val Ala Tyr
        355                 360                 365

Ile Pro Pro Gly Val Glu Thr Asp Lys Leu Pro Lys Thr Pro Glu Asp
    370                 375                 380

Ala Ala His Cys Tyr His Ser Glu Trp Asp Thr Gly Leu Asn Ser Gln
385                 390                 395                 400

Phe Thr Phe Ala Val Pro Tyr Val Ser Ala Ser Asp Phe Ser Tyr Thr
                405                 410                 415

His Thr Asp Thr Pro Ala Met Ala Thr Thr Asn Gly Trp Ile Ala Val
            420                 425                 430

Tyr Gln Val Thr Asp Thr His Ser Ala Glu Ala Ala Val Val Val Ser
        435                 440                 445

Val Ser Ala Gly Pro Asp Leu Glu Phe Arg Phe Pro Ile Asp Pro Val
    450                 455                 460

Arg Gln Arg Gly Arg Lys Arg Arg Ser Thr Thr Ser Ala Gly Glu Gly
```

```
465                 470                 475                 480

Ala Asp Val Val Thr Thr Asp Pro Ser Thr His Gly Gly Val Glu Lys
                485                 490                 495

Arg Arg Met His Thr Asp Val Ala Phe Val Leu Asp Arg Phe Thr His
            500                 505                 510

Val His Thr Asn Lys Thr Thr Phe Asn Val Asp Leu Met Asp Thr Lys
        515                 520                 525

Lys Ala Leu Val Gly Ala Leu Leu Arg Ala Ser Thr Tyr Tyr Phe Cys
    530                 535                 540

Asp Leu Glu Ile Ala Cys Val Gly Glu His Lys Arg Val Phe Trp Gln
545                 550                 555                 560

Pro Asn Gly Ala Pro Arg Thr Thr Gln Leu Gly Asp Asn Pro Met Val
                565                 570                 575

Phe Ser His Asn Val Thr Arg Phe Ala Ile Pro Tyr Thr Ala Pro His
            580                 585                 590

Arg Leu Leu Ser Thr Val Tyr Asn Gly Glu Cys Lys Tyr Thr Val Ala
        595                 600                 605

Ile Arg Gly Asp Arg Ala Val Leu Ala Ala Lys Tyr Ala Thr His Thr
    610                 615                 620

Leu Pro Ser Thr Phe Asn Phe Gly His Val Thr Ala Asp Lys Pro Val
625                 630                 635                 640

Asp Val Tyr Tyr Arg Met Lys Arg Ala Glu Leu Tyr Cys Pro Arg Pro
                645                 650                 655

Leu Leu Pro Ala Tyr His Arg Asp Arg Phe Asp Ala Pro Ile Gly Val
            660                 665                 670

Glu Lys Gln Leu Cys Asn Phe Asp Leu Leu Lys Leu Arg Gly Arg Lys
        675                 680                 685

Arg Arg Ser Asn Phe Asp Leu Leu Lys Leu Ala Gly Asp Val Glu Ser
    690                 695                 700

Asn Pro Gly
705


<210> SEQ ID NO 13
<211> LENGTH: 5357
<212> TYPE: DNA
<213> ORGANISM: Artificial Sequence
<220> FEATURE:
<223> OTHER INFORMATION: A24cruzeiro-Long in pVAX nucleic acid

<400> SEQUENCE: 13

gactcttcgc gatgtacggg ccagatatac gcgttgacat tgattattga ctagttatta      60

atagtaatca attacggggt cattagttca tagcccatat atggagttcc gcgttacata     120

acttacggta aatggcccgc ctggctgacc gcccaacgac ccccgcccat tgacgtcaat     180

aatgacgtat gttcccatag taacgccaat agggactttc cattgacgtc aatgggtgga     240

gtatttacgg taaactgccc acttggcagt acatcaagtg tatcatatgc caagtacgcc     300

ccctattgac gtcaatgacg gtaaatggcc cgcctggcat tatgcccagt acatgacctt     360

atgggacttt cctacttggc agtacatcta cgtattagtc atcgctatta ccatggtgat     420

gcggttttgg cagtacatca atgggcgtgg atagcggttt gactcacggg gatttccaag     480

tctccacccc attgacgtca atgggagttt gttttggcac caaaatcaac gggactttcc     540

aaaatgtcgt aacaactccg ccccattgac gcaaatgggc ggtaggcgtg tacggtggga     600

ggtctatata agcagagctc tctggctaac tagagaaccc actgcttact ggcttatcga     660
```

-continued

```
aattaatacg actcactata gggagaccca agctggctag cgtttaaact taagcttggt    720
accgagctcg gatccgccac catggattgg acatggattc tgttcctggt ggctgctgct    780
actagagtgc attcaggggc cggacagtct tcacccgcaa ccggatcaca gaaccagagt    840
ggaaataccg ggagcatcat taacaattac tatatgcagc agtaccagaa cagcatggac    900
acacagctgg gggataacgc catcagcggc ggcagcaatg agggctccac agataccaca    960
tctactcaca ctaccaatac ccagaacaat gactggttct ctaaactggc aagctccgcc   1020
ttcaccggcc tctttggagc tctgctcgca aggggaagaa agaggagaag cgataagaaa   1080
acagaggaaa ccaccctgct ggaggacaga atcctgacca caagaaacgg gcacactacc   1140
agcacaactc agtcttcagt gggcgtcaca cacggatact caactgagga agaccatgtg   1200
gccgggccaa ataccagtgg cctggagaca cgagtggtcc aggctgaaag gttctacaag   1260
aaatatctgt ttgactggac cacagataag gccttcggcc acctggagaa actggaactc   1320
ccctcagacc accacggcgt gttcggccat ctggtcgata gctacgccta tatgagaaac   1380
ggatgggacg tggaggtctc cgctgtgggc aaccagttca atggcggatg cctgctcgtg   1440
gctatggtgc ccgagtggaa ggaatttgat accagggaaa aataccagct gacactcttc   1500
ccacaccagt ttatctctcc tagaactaac atgaccgccc atattaccgt gccttatctg   1560
ggcgtcaatc ggtacgacca gtataagaaa cacaaacctt ggaccctggt ggtcatggtg   1620
gtcagtcccc tcacagtgaa caatactagc gccgctcaga tcaaggtcta cgccaacatt   1680
gctccaacct atgtgcacgt cgcaggagag ctgccttcca aggaacgggg acgcaaacgg   1740
cgctctggga tcttcccagt ggcatgtgct gacggatacg gagggctggt cactaccgac   1800
cctaagaccg cagatcccgc ctacggaaaa gtgtataacc cacccaggac taattaccca   1860
gggcggttca ccaacctgct cgatgtggca gaggcctgcc ccaccttcct gtgctttgac   1920
gatggcaagc catacgtgac aactcggaca gacgatactc gcctgctcgc caagtttgac   1980
ctgagcctcg cagccaaaca catgtcaaac acctacctga gtggaatcgc ccagtactat   2040
actcagtatt ccgggaccat taatctgcat ttcatgttta ccggctctac agactcaaag   2100
gctcgctaca tggtggcata tatccctccc ggcgtcgaga ccccacctga tacacctgaa   2160
agggctgcac actgcatcca tgccgagtgg gacacaggac tgaacagcaa gttcactttt   2220
tccattccct acgtgtctgc cgctgactac gcttataccg catccgatac tgccgaaacc   2280
attaacgtgc agggatgggt ctgtatctac cagattactc acgggaaagc cgagaatgac   2340
accctggtgg tctccgtgtc tgctggcaag gacttcgaac tgcgcctccc tatcgatccc   2400
cgacagcagc gaggcaggaa gcgaaggagc accacagcca ccggagagtc cgctgaccct   2460
gtgactacca cagtcgagaa ctacggcgga gaaacacaga ttcagagacg gcaccatact   2520
gacatcggat tcattatgga tagatttgtg aagatccagt cactgagtcc cacccacgtg   2580
attgatctca tgcagacaca ccagcatgga ctggtggggg ccctgctccg agcagcaacc   2640
tactacttca gcgacctgga gatcgtggtc cgccatgaag gcaacctgac atgggtgcca   2700
aatggagccc ctgagtcagc tctgctcaac actagtaatc ccaccgcata caacaaagcc   2760
cccttcaccc ggctggcact cccctataca gccccacacc gcgtgctggc cacagtctac   2820
aatggcactt ctaagtatgc tgtgggcggc agcggcagga ggggcgacat ggggtccctc   2880
gctgcacggg tggtcaagca gctgccagct tctttcaact acggagcaat caaagctgac   2940
gcaattcacg agctgctcgt gcgcatgaag cgagcagaac tgtattgccc caggccactg   3000
ctcgctatcg aggtgagtag ccaggacaga cataagcaga aaatcattgc ccccgctaag   3060
```

-continued cagctgctca gaggccggaa gagacgatct aattttgacc tgctcaagct cgccggagac 3120
gtggaatcta atcctggatg ataactcgag tctagagggc ccgtttaaac ccgctgatca 3180
gcctcgactg tgccttctag ttgccagcca tctgttgttt gcccctcccc cgtgccttcc 3240
ttgaccctgg aaggtgccac tcccactgtc ctttcctaat aaaatgagga aattgcatcg 3300
cattgtctga gtaggtgtca ttctattctg gggggtgggg tggggcagga cagcaagggg 3360
gaggattggg aagacaatag caggcatgct ggggatgcgg tgggctctat ggcttctact 3420
gggcggtttt atggacagca agcgaaccgg aattgccagc tggggcgccc tctggtaagg 3480
ttgggaagcc ctgcaaagta aactggatgg ctttcttgcc gccaaggatc tgatggcgca 3540
ggggatcaag ctctgatcaa gagacaggat gaggatcgtt tcgcatgatt gaacaagatg 3600
gattgcacgc aggttctccg gccgcttggg tggagaggct attcggctat gactgggcac 3660
aacagacaat cggctgctct gatgccgccg tgttccggct gtcagcgcag gggcgcccgg 3720
ttctttttgt caagaccgac ctgtccggtg ccctgaatga actgcaagac gaggcagcgc 3780
ggctatcgtg gctggccacg acgggcgttc cttgcgcagc tgtgctcgac gttgtcactg 3840
aagcgggaag ggactggctg ctattgggcg aagtgccggg gcaggatctc ctgtcatctc 3900
accttgctcc tgccgagaaa gtatccatca tggctgatgc aatgcggcgg ctgcatacgc 3960
ttgatccggc tacctgccca ttcgaccacc aagcgaaaca tcgcatcgag cgagcacgta 4020
ctcggatgga agccggtctt gtcgatcagg atgatctgga cgaagagcat caggggctcg 4080
cgccagccga actgttcgcc aggctcaagg cgagcatgcc cgacggcgag gatctcgtcg 4140
tgacccatgg cgatgcctgc ttgccgaata tcatggtgga aaatggccgc ttttctggat 4200
tcatcgactg tggccggctg ggtgtggcgg accgctatca ggacatagcg ttggctaccc 4260
gtgatattgc tgaagagctt ggcggcgaat gggctgaccg cttcctcgtg ctttacggta 4320
tcgccgctcc cgattcgcag cgcatcgcct tctatcgcct tcttgacgag ttcttctgaa 4380
ttattaacgc ttacaatttc ctgatgcggt attttctcct tacgcatctg tgcggtattt 4440
cacaccgcat caggtggcac ttttcgggga aatgtgcgcg gaacccctat ttgtttattt 4500
ttctaaatac attcaaatat gtatccgctc atgagacaat aaccctgata aatgcttcaa 4560
taatagcacg tgctaaaact tcatttttaa tttaaaagga tctaggtgaa gatccttttt 4620
gataatctca tgaccaaaat cccttaacgt gagttttcgt tccactgagc gtcagacccc 4680
gtagaaaaga tcaaaggatc ttcttgagat cctttttttc tgcgcgtaat ctgctgcttg 4740
caaacaaaaa aaccaccgct accagcggtg gtttgtttgc cggatcaaga gctaccaact 4800
ctttttccga aggtaactgg cttcagcaga gcgcagatac caaatactgt tcttctagtg 4860
tagccgtagt taggccacca cttcaagaac tctgtagcac cgcctacata cctcgctctg 4920
ctaatcctgt taccagtggc tgctgccagt ggcgataagt cgtgtcttac cgggttggac 4980
tcaagacgat agttaccgga taaggcgcag cggtcgggct gaacgggggg ttcgtgcaca 5040
cagcccagct tggagcgaac gacctacacc gaactgagat acctacagcg tgagctatga 5100
gaaagcgcca cgcttcccga agggagaaag gcggacaggt atccggtaag cggcagggtc 5160
ggaacaggag agcgcacgag ggagcttcca gggggaaacg cctggtatct ttatagtcct 5220
gtcgggtttc gccacctctg acttgagcgt cgatttttgt gatgctcgtc aggggggcgg 5280
agcctatgga aaaacgccag caacgcggcc tttttacggt tcctggcctt ttgctggcct 5340
tttgctcaca tgttctt 5357

<210> SEQ ID NO 14
<211> LENGTH: 5081
<212> TYPE: DNA
<213> ORGANISM: Artificial Sequence
<220> FEATURE:
<223> OTHER INFORMATION: A24cruzeiro-Short in pVAX nucleic acid

<400> SEQUENCE: 14
gactcttcgc gatgtacggg ccagatatac gcgttgacat tgattattga ctagttatta 60
atagtaatca attacggggt cattagttca tagcccatat atggagttcc gcgttacata 120
acttacggta aatggcccgc ctggctgacc gcccaacgac ccccgcccat tgacgtcaat 180
aatgacgtat gttcccatag taacgccaat agggactttc cattgacgtc aatgggtgga 240
gtatttacgg taaactgccc acttggcagt acatcaagtg tatcatatgc caagtacgcc 300
ccctattgac gtcaatgacg gtaaatggcc cgcctggcat tatgcccagt acatgacctt 360
atgggacttt cctacttggc agtacatcta cgtattagtc atcgctatta ccatggtgat 420
gcggttttgg cagtacatca atgggcgtgg atagcggttt gactcacggg gatttccaag 480
tctccacccc attgacgtca atgggagttt gttttggcac caaaatcaac gggactttcc 540
aaaatgtcgt aacaactccg ccccattgac gcaaatgggc ggtaggcgtg tacggtggga 600
ggtctatata agcagagctc tctggctaac tagagaaccc actgcttact ggcttatcga 660
aattaatacg actcactata gggagaccca agctggctag cgtttaaact taagcttggt 720
accgagctcg gatccgccac catggactgg acctggattc tgttcctcgt cgccgccgca 780
acacgggtgc attcagacaa aaagaccgaa gagactacac tcctggagga tagaatcctg 840
accacacgga acggccacac tacctccaca actcagagct ccgtgggcgt cacacacgga 900
tacagcactg aggaagacca tgtggccggg ccaaatacct ccggcctgga gacaagggtg 960
gtccaggctg aaagattcta caagaagtat ctcttcgact ggaccacaga taaggccttc 1020
ggacacctgg agaaactgga actcccctct gaccaccacg gcgtgttcgg ccatctggtc 1080
gattcatacg cctatatgag gaacggatgg gacgtggagg tctccgctgt gggcaaccag 1140
ttcaatggcg gatgcctgct cgtggctatg gtgcccgagt ggaaggaatt tgataccagg 1200
gaaaaatacc agctgacact cttcccacac cagtttatct ctcctagaac taacatgacc 1260
gcccatatta cagtgcctta tctgggcgtc aatcggtacg accagtataa gaaacacaaa 1320
ccttggaccc tggtggtcat ggtggtgagc cccctgacag tgaacaatac ttctgccgct 1380
cagatcaagg tctacgcaaa cattgcccca acctatgtgc acgtcgccgg cgagctgcct 1440
tcaaaggaac gcggacgaaa aaggagaagt gggatcttcc cagtggcatg tgctgacgga 1500
tacggcggac tggtcactac cgaccctaag accgctgatc ccgcatacgg gaaagtgtat 1560
aacccaccca ggactaatta cccaggccgc ttcaccaatc tgctcgatgt ggcagaggcc 1620
tgccccacct tcctgtgctt tgacgatggc aagccatacg tgacaactcg cacagacgat 1680
actcgactgc tcgccaagtt tgacctgagc ctcgcagcca aacacatgag caacacctac 1740
ctgtccggaa tcgcccagta ctatactcag tatagcggga ccattaatct gcatttcatg 1800
tttaccggct caacagacag taaagcccgc tacatggtgg cttatatccc tcccggagtc 1860
gagaccccac ctgatacacc tgaaagggct gcacactgca tccatgccga gtgggacaca 1920
gggctgaact ctaagttcac tttttcaatt ccctacgtga gtgccgctga ctacgcctat 1980
accgccagcg atactgccga gaccatcaac gtgcagggat gggtctgtat ctaccagatt 2040
actcacggga aagccgagaa tgacaccctg gtggtgagcg tgagcgccgg aaaggacttc 2100

-continued

```
gaactgcgac tccctatcga tccaaggcag cagaggggca gaaagcggcg ctctaccaca   2160
gcaaccggag agtcagccga ccctgtgact accacagtcg agaactacgg aggggaaaca   2220
cagattcagc gaaggcacca taccgacatc gggttcatta tggatagatt tgtgaagatc   2280
cagtccctgt ctcccacaca cgtgattgat ctcatgcaga cccaccagca tggactggtg   2340
ggggccctgc tccgagcagc aacatactac ttcagcgacc tggagatcgt ggtccgccat   2400
gaaggcaacc tgacctgggt gccaaatgga gcacctgaga gcgccctgct caacacttcc   2460
aatcccaccg cttacaacaa agcacccttc accagactgg ctctccccta tacagcacca   2520
caccgggtgc tggcaacagt ctacaatggg actagtaagt atgcagtggg cggaagcggc   2580
agacggggag atatggggtc cctcgctgca cgggtggtca agcagctgcc agcctctttc   2640
aactacggcg ctatcaaagc tgacgcaatt cacgagctgc tcgtgcgaat gaagagggct   2700
gaactgtatt gcccccgccc actgctcgca atcgaggtgt cttcacagga ccgacataag   2760
cagaaaatca ttgcccccgc taagcagctg ctcaggggca ggaaaagacg cagtaatttc   2820
gacctcctca agctcgcagg cgacgtggaa tctaaccccg gctgataact cgagtctaga   2880
gggcccgttt aaacccgctg atcagcctcg actgtgcctt ctagttgcca gccatctgtt   2940
gtttgcccct cccccgtgcc ttccttgacc ctggaaggtg ccactcccac tgtcctttcc   3000
taataaaatg aggaaattgc atcgcattgt ctgagtaggt gtcattctat tctggggggt   3060
ggggtggggc aggacagcaa gggggaggat tgggaagaca atagcaggca tgctggggat   3120
gcggtgggct ctatggcttc tactgggcgg ttttatggac agcaagcgaa ccggaattgc   3180
cagctggggc gccctctggt aaggttggga agccctgcaa agtaaactgg atggctttct   3240
tgccgccaag gatctgatgg cgcaggggat caagctctga tcaagagaca ggatgaggat   3300
cgtttcgcat gattgaacaa gatggattgc acgcaggttc tccggccgct tgggtggaga   3360
ggctattcgg ctatgactgg gcacaacaga caatcggctg ctctgatgcc gccgtgttcc   3420
ggctgtcagc gcaggggcgc ccggttcttt ttgtcaagac cgacctgtcc ggtgccctga   3480
atgaactgca agacgaggca gcgcggctat cgtggctggc cacgacgggc gttccttgcg   3540
cagctgtgct cgacgttgtc actgaagcgg gaagggactg gctgctattg ggcgaagtgc   3600
cggggcagga tctcctgtca tctcaccttg ctcctgccga gaaagtatcc atcatggctg   3660
atgcaatgcg gcggctgcat acgcttgatc cggctacctg cccattcgac caccaagcga   3720
aacatcgcat cgagcgagca cgtactcgga tggaagccgg tcttgtcgat caggatgatc   3780
tggacgaaga gcatcagggg ctcgcgccag ccgaactgtt cgccaggctc aaggcgagca   3840
tgcccgacgg cgaggatctc gtcgtgaccc atggcgatgc ctgcttgccg aatatcatgg   3900
tggaaaatgg ccgcttttct ggattcatcg actgtggccg gctgggtgtg gcggaccgct   3960
atcaggacat agcgttggct acccgtgata ttgctgaaga gcttggcggc gaatgggctg   4020
accgcttcct cgtgctttac ggtatcgccg ctcccgattc gcagcgcatc gccttctatc   4080
gccttcttga cgagttcttc tgaattatta acgcttacaa tttcctgatg cggtattttc   4140
tccttacgca tctgtgcggt atttcacacc gcatcaggtg gcacttttcg gggaaatgtg   4200
cgcggaaccc ctatttgttt atttttctaa atacattcaa atatgtatcc gctcatgaga   4260
caataaccct gataaatgct tcaataatag cacgtgctaa aacttcattt ttaatttaaa   4320
aggatctagg tgaagatcct ttttgataat ctcatgacca aaatccctta acgtgagttt   4380
tcgttccact gagcgtcaga ccccgtagaa aagatcaaag gatcttcttg agatcctttt   4440
```

-continued

```
tttctgcgcg taatctgctg cttgcaaaca aaaaaaccac cgctaccagc ggtggtttgt   4500

ttgccggatc aagagctacc aactcttttt ccgaaggtaa ctggcttcag cagagcgcag   4560

ataccaaata ctgttcttct agtgtagccg tagttaggcc accacttcaa gaactctgta   4620

gcaccgccta catacctcgc tctgctaatc ctgttaccag tggctgctgc cagtggcgat   4680

aagtcgtgtc ttaccgggtt ggactcaaga cgatagttac cggataaggc gcagcggtcg   4740

ggctgaacgg ggggttcgtg cacacagccc agcttggagc gaacgaccta caccgaactg   4800

agatacctac agcgtgagct atgagaaagc gccacgcttc ccgaagggag aaaggcggac   4860

aggtatccgg taagcggcag ggtcggaaca ggagagcgca cgagggagct tccaggggga   4920

aacgcctggt atctttatag tcctgtcggg tttcgccacc tctgacttga gcgtcgattt   4980

ttgtgatgct cgtcaggggg gcggagccta tggaaaaacg ccagcaacgc ggccttttta   5040

cggttcctgg ccttttgctg gccttttgct cacatgttct t                        5081
```

<210> SEQ ID NO 15
<211> LENGTH: 5345
<212> TYPE: DNA
<213> ORGANISM: Artificial Sequence
<220> FEATURE:
<223> OTHER INFORMATION: As1-Shamir-89-Long in pVAX nucleic acid

<400> SEQUENCE: 15

```
gactcttcgc gatgtacggg ccagatatac gcgttgacat tgattattga ctagttatta     60

atagtaatca attacggggt cattagttca tagcccatat atggagttcc gcgttacata    120

acttacggta aatggcccgc ctggctgacc gcccaacgac ccccgcccat tgacgtcaat    180

aatgacgtat gttcccatag taacgccaat agggactttc cattgacgtc aatgggtgga    240

gtatttacgg taaactgccc acttggcagt acatcaagtg tatcatatgc caagtacgcc    300

ccctattgac gtcaatgacg gtaaatggcc cgcctggcat tatgcccagt acatgacctt    360

atgggacttt cctacttggc agtacatcta cgtattagtc atcgctatta ccatggtgat    420

gcggttttgg cagtacatca atgggcgtgg atagcggttt gactcacggg gatttccaag    480

tctccacccc attgacgtca atgggagttt gttttggcac caaaatcaac gggactttcc    540

aaaatgtcgt aacaactccg ccccattgac gcaaatgggc ggtaggcgtg tacggtggga    600

ggtctatata agcagagctc tctggctaac tagagaaccc actgcttact ggcttatcga    660

aattaatacg actcactata gggagaccca agctggctag cgtttaaact taagcttggt    720

accgagctcg gatccgccac catggattgg acatggattc tgttcctggt cgccgccgca    780

acacgggtgc attctggggc cggacagtct tcacctgcta ctgggagcca gaaccagagc    840

ggaaatacag ggtccatcat taacaattac tatatgcagc agtaccagaa cagcatggac    900

acccagctgg gcgataacgc catctccggc ggatctaatg agggatctac tgacaccaca    960

tcaacacaca ctaacaatac ccagaacaat gattggttca gtagactcgc cagctccgct   1020

ttctctggac tgtttggagc actgctcgcc cggggccgca agaggagatc cgacaagaaa   1080

accgaggaaa ccaccctgct ggaggatcga atcctgacaa ctaggaacgg acataccaca   1140

agcactaccc agtcttcagt gggagtcacc tacgggtatg ctgtcgcaga agacgccgtg   1200

agtgggccca acacaagcgg cctggagact agagtgcagc aggctgaacg gttctttaag   1260

aaacacctct tcgattggac acctaatctg gcctttggcc attgctacta tctggagctc   1320

cccaccgaac acaagggggt gtacggctca ctgatgggga gttacgcata tatgcggaac   1380

ggatgggaca tcgaggtgac cgcagtcgga aaccagttca atggcggatg tctgctcgtg   1440
```

-continued

```
gctctggtcc ctgagctgaa ggaactcgat acaaggcaga aataccagct gactctcttc   1500
cctcatcagt ttattaaccc cagaacaaat atgactgccc acatcaacgt gccctacgtc   1560
ggcattaatc ggtacgacca gtatgccctc cataagcctt ggaccctggt ggtcatggtg   1620
gtcgctcccc tgaccgtgaa gacaggaggg tccgagcaga tcaaagtgta catgaacgcc   1680
gctccaacct atgtgcacgt cgccggcgag ctgccttcaa aggaacgagg caggaaacgg   1740
cgctctggaa ttgtgccagt cgcatgcgct gacggatacg gaaacatggt gacaactgac   1800
cccaagaccg ccgatccagt ctatggaaaa gtgttcaacc cacccaggac caatctccct   1860
gggcgattca caaactttct ggatgtggca gaggcctgtc ccacattcct gcggtttggg   1920
gaagtgccat tcgtcaagac cgtgaacagc ggcgaccgac tgctcgccaa atttgacgtg   1980
agcctggccg ccggccacat gagtaacacc tacctggctg gactcgcaca gtactatacc   2040
cagtatagcg ggacaatgaa tgtgcacttc atgtttactg gcccaaccga cgctaaggca   2100
agatacatgg tcgcctatgt gcctcccggg atgacaccac ctactgaccc tgagcacgct   2160
gcacattgca tccacagcga atgggatact ggcctcaact ccaaattcac cttttctatt   2220
ccctacctgt cagccgctga ctacgcctat acagccagcg atgtggccga gaccacatcc   2280
gtccagggat gggtgtgcat ctaccagatt acccacggca aggctgaggg agacgcactg   2340
gtggtgagcg tgagcgccgg gaaagacttc gaatttcggc tgcccgtgga tgcacgccag   2400
cagagaggac ggaagcgaag gtctactacc acaactgggg aatcagccga cccagtcacc   2460
acaactgtgg agaactacgg cggagaaacc cagacagcaa gacggctgca caccgacgtg   2520
gccttcatcc tcgatcgctt tgtgaagctg acagccccca aaaatatcca gactctggac   2580
ctcatgcaga ttccatccca tacactggtg ggcgcactgc tcaggagtgc cacttactat   2640
ttcagcgacc tggaggtcgc tctcgtgcac actggaccag tcacctgggt gcctaacgga   2700
gcaccaaagg atgctctgaa caatcagacc aatccaacag cctaccagaa acagcctatc   2760
accaggctgg ctctcccata tacagcacct cacagagtcc tggctaccgt gtacaacgga   2820
aagaccgcct acggcgagac cacaagccgc cgaggcgaca tggcagccct ggcccagcgg   2880
ctctccgctc gcctgcccac atctttcaat tacggagcag tgaaggccga tactatcacc   2940
gagctgctca ttaggatgaa aagagccgaa acctattgcc ccaggccact gctcgctctg   3000
gacactaccc aggataggag aaagcaggag atcattgccc cagaaaaaca ggtgctgcgc   3060
ggccgaaaaa gacggagtaa tttcgacctg ctcaagctcg ctggcgatgt ggaaagtaat   3120
cccggatgat aactcgagtc tagagggccc gtttaaaccc gctgatcagc ctcgactgtg   3180
ccttctagtt gccagccatc tgttgtttgc ccctcccccg tgccttcctt gaccctggaa   3240
ggtgccactc ccactgtcct ttcctaataa aatgaggaaa ttgcatcgca ttgtctgagt   3300
aggtgtcatt ctattctggg gggtggggtg gggcaggaca gcaaggggga ggattgggaa   3360
gacaatagca ggcatgctgg ggatgcggtg ggctctatgg cttctactgg gcggttttat   3420
ggacagcaag cgaaccggaa ttgccagctg gggcgccctc tggtaaggtt gggaagccct   3480
gcaaagtaaa ctggatggct ttcttgccgc caaggatctg atggcgcagg ggatcaagct   3540
ctgatcaaga gacaggatga ggatcgtttc gcatgattga acaagatgga ttgcacgcag   3600
gttctccggc cgcttgggtg gagaggctat tcggctatga ctgggcacaa cagacaatcg   3660
gctgctctga tgccgccgtg ttccggctgt cagcgcaggg gcgcccggtt ctttttgtca   3720
agaccgacct gtccggtgcc ctgaatgaac tgcaagacga ggcagcgcgg ctatcgtggc   3780
```

```
tggccacgac gggcgttcct tgcgcagctg tgctcgacgt tgtcactgaa gcgggaaggg   3840
actggctgct attgggcgaa gtgccggggc aggatctcct gtcatctcac cttgctcctg   3900
ccgagaaagt atccatcatg gctgatgcaa tgcggcggct gcatacgctt gatccggcta   3960
cctgcccatt cgaccaccaa gcgaaacatc gcatcgagcg agcacgtact cggatggaag   4020
ccggtcttgt cgatcaggat gatctggacg aagagcatca ggggctcgcg ccagccgaac   4080
tgttcgccag gctcaaggcg agcatgcccg acggcgagga tctcgtcgtg acccatggcg   4140
atgcctgctt gccgaatatc atggtggaaa atggccgctt ttctggattc atcgactgtg   4200
gccggctggg tgtggcggac cgctatcagg acatagcgtt ggctacccgt gatattgctg   4260
aagagcttgg cggcgaatgg gctgaccgct tcctcgtgct ttacggtatc gccgctcccg   4320
attcgcagcg catcgccttc tatcgccttc ttgacgagtt cttctgaatt attaacgctt   4380
acaatttcct gatgcggtat tttctcctta cgcatctgtg cggtatttca caccgcatca   4440
ggtggcactt ttcggggaaa tgtgcgcgga acccctattt gtttattttt ctaaatacat   4500
tcaaatatgt atccgctcat gagacaataa ccctgataaa tgcttcaata atagcacgtg   4560
ctaaaacttc atttttaatt taaaaggatc taggtgaaga tcctttttga taatctcatg   4620
accaaaatcc cttaacgtga gttttcgttc cactgagcgt cagaccccgt agaaaagatc   4680
aaaggatctt cttgagatcc tttttttctg cgcgtaatct gctgcttgca aacaaaaaaa   4740
ccaccgctac cagcggtggt ttgtttgccg gatcaagagc taccaactct ttttccgaag   4800
gtaactggct tcagcagagc gcagatacca aatactgttc ttctagtgta gccgtagtta   4860
ggccaccact tcaagaactc tgtagcaccg cctacatacc tcgctctgct aatcctgtta   4920
ccagtggctg ctgccagtgg cgataagtcg tgtcttaccg ggttggactc aagacgatag   4980
ttaccggata aggcgcagcg gtcgggctga acggggggtt cgtgcacaca gcccagcttg   5040
gagcgaacga cctacaccga actgagatac ctacagcgtg agctatgaga aagcgccacg   5100
cttcccgaag ggagaaaggc ggacaggtat ccggtaagcg gcagggtcgg aacaggagag   5160
cgcacgaggg agcttccagg gggaaacgcc tggtatcttt atagtcctgt cgggtttcgc   5220
cacctctgac ttgagcgtcg atttttgtga tgctcgtcag gggggcggag cctatggaaa   5280
aacgccagca acgcggcctt tttacggttc ctggcctttt gctggccttt tgctcacatg   5340
ttctt                                                               5345
```

<210> SEQ ID NO 16
<211> LENGTH: 5069
<212> TYPE: DNA
<213> ORGANISM: Artificial Sequence
<220> FEATURE:
<223> OTHER INFORMATION: As1-Shamir-89-Short in pVAX nucleic acid

<400> SEQUENCE: 16

```
gactcttcgc gatgtacggg ccagatatac gcgttgacat tgattattga ctagttatta     60
atagtaatca attacggggt cattagttca tagcccatat atggagttcc gcgttacata    120
acttacggta aatggcccgc ctggctgacc gcccaacgac ccccgcccat tgacgtcaat    180
aatgacgtat gttcccatag taacgccaat agggactttc cattgacgtc aatgggtgga    240
gtatttacgg taaactgccc acttggcagt acatcaagtg tatcatatgc caagtacgcc    300
ccctattgac gtcaatgacg gtaaatggcc cgcctggcat tatgcccagt acatgacctt    360
atgggacttt cctacttggc agtacatcta cgtattagtc atcgctatta ccatggtgat    420
gcggttttgg cagtacatca atgggcgtgg atagcggttt gactcacggg gatttccaag    480
```

-continued

```
tctccacccc attgacgtca atgggagttt gttttggcac caaaatcaac gggactttcc    540
aaaatgtcgt aacaactccg ccccattgac gcaaatgggc ggtaggcgtg tacggtggga    600
ggtctatata agcagagctc tctggctaac tagagaaccc actgcttact ggcttatcga    660
aattaatacg actcactata gggagaccca agctggctag cgtttaaact taagcttggt    720
accgagctcg gatccgccac catggactgg acctggattc tgttcctggt ggccgccgca    780
actcgcgtgc attcagataa aaagaccgaa gagactacac tcctggaaga cagaatcctg    840
accacaagaa acggccatac taccagcaca actcagagct ccgtgggagt cacctacggg    900
tatgctgtcg cagaggacgc cgtgtccgga ccaaacacat ctggcctgga gactcgggtg    960
cagcaggctg aacgcttctt taagaaacac ctcttcgatt ggacacctaa tctggccttt   1020
ggacattgct actatctgga gctccccacc gaacacaagg gggtgtacgg cagtctgatg   1080
gggagctacg cttatatgag aaacggctgg gacatcgagg tgaccgcagt cgggaaccag   1140
ttcaatggcg gatgtctgct cgtggctctg gtccctgagc tgaaggaact cgatacaagg   1200
cagaaatacc agctgactct cttccctcat cagtttatta accccagaac aaatatgact   1260
gcccacatca acgtgcccta cgtcggcatt aatcggtacg accagtatgc actccataag   1320
ccttggacac tggtggtcat ggtggtcgct cccctgaccg tgaagacagg gggctccgag   1380
cagatcaaag tgtacatgaa cgccgctcca acctatgtgc acgtcgccgg agagctgcct   1440
tccaaggaaa ggggcagaaa aaggaggagc ggaattgtgc cagtcgcctg cgctgacggc   1500
tacggaaaca tggtgaccac agaccccaag accgccgatc cagtctatgg gaaagtgttc   1560
aacccaccca ggaccaatct ccctggcagg ttcacaaact ttctggatgt ggcagaggcc   1620
tgtcccacat tcctgcggtt tggcgaagtg ccattcgtca agaccgtgaa cagcggagac   1680
cgcctgctcg ccaaatttga tgtgagcctg gcagccggcc acatgtccaa cacctacctg   1740
gccggactcg ctcagtacta tacccagtat agcgggacaa tgaatgtgca cttcatgttt   1800
actggcccaa ccgacgctaa ggcacggtac atggtcgcct atgtgcctcc cggcatgaca   1860
ccacctactg accctgagca cgctgcacat tgcatccaca gcgaatggga tactggactc   1920
aactcaaaat tcacctttag tattccctac ctgagcgccg ctgactacgc atatacagcc   1980
tctgatgtgg ccgagactac ctcagtccag ggtgggtgt gcatctacca gattacccac   2040
ggcaaggcag agggagacgc tctcgtggtg agcgtgagcg ccggcaaaga cttcgagttc   2100
aggctgccag tggatgctcg acagcagcgg ggacgcaagc ggcgcagtac aactaccaca   2160
ggggaaagcg ccgatccagt cactaccaca gtggagaact acggagggga aacccagaca   2220
gctcgaaggc tgcacaccga cgtggcattc atcctcgatc gctttgtgaa gctgacagcc   2280
cccaaaaata tccagactct ggacctcatg cagattccat cccatactct ggtgggcgct   2340
ctgctcaggt ccgcaaccta ctatttctct gacctggagg tcgctctcgt gcacactgga   2400
ccagtcacct gggtgcctaa cggagcacca aaggatgccc tgaacaatca gaccaatcca   2460
acagcctacc agaaacagcc tatcacccgc ctggccctcc catatacagc tcctcaccga   2520
gtcctggcca ccgtgtacaa cggaaagacc gcttatgggg agaccaccag caggaggggc   2580
gacatggcag ccctggcaca gcgcctctca gcccgactgc ccacaagttt caattacggg   2640
gctgtgaagg cagatactat caccgagctg ctcattagaa tgaaacgggc agaaacctat   2700
tgccccaggc cactgctcgc cctggacaca actcaggatc gccgaaagca ggagatcatt   2760
gccccagaaa aacaggtgct gcgaggcagg aaaagacgca gtaatttcga cctcctcaag   2820
```

-continued

```
ctcgcaggcg acgtggaatc taatcccgga tgataactcg agtctagagg gcccgtttaa   2880
acccgctgat cagcctcgac tgtgccttct agttgccagc catctgttgt ttgcccctcc   2940
cccgtgcctt ccttgaccct ggaaggtgcc actcccactg tcctttccta ataaaatgag   3000
gaaattgcat cgcattgtct gagtaggtgt cattctattc tggggggtgg ggtggggcag   3060
gacagcaagg gggaggattg ggaagacaat agcaggcatg ctggggatgc ggtgggctct   3120
atggcttcta ctgggcggtt ttatggacag caagcgaacc ggaattgcca gctggggcgc   3180
cctctggtaa ggttgggaag ccctgcaaag taaactggat ggctttcttg ccgccaagga   3240
tctgatggcg caggggatca agctctgatc aagagacagg atgaggatcg tttcgcatga   3300
ttgaacaaga tggattgcac gcaggttctc cggccgcttg ggtggagagg ctattcggct   3360
atgactgggc acaacagaca atcggctgct ctgatgccgc cgtgttccgg ctgtcagcgc   3420
aggggcgccc ggttcttttt gtcaagaccg acctgtccgg tgccctgaat gaactgcaag   3480
acgaggcagc gcggctatcg tggctggcca cgacgggcgt tccttgcgca gctgtgctcg   3540
acgttgtcac tgaagcggga agggactggc tgctattggg cgaagtgccg gggcaggatc   3600
tcctgtcatc tcaccttgct cctgccgaga aagtatccat catggctgat gcaatgcggc   3660
ggctgcatac gcttgatccg gctacctgcc cattcgacca ccaagcgaaa catcgcatcg   3720
agcgagcacg tactcggatg gaagccggtc ttgtcgatca ggatgatctg gacgaagagc   3780
atcaggggct cgcgccagcc gaactgttcg ccaggctcaa ggcgagcatg cccgacggcg   3840
aggatctcgt cgtgacccat ggcgatgcct gcttgccgaa tatcatggtg gaaaatggcc   3900
gcttttctgg attcatcgac tgtggccggc tgggtgtggc ggaccgctat caggacatag   3960
cgttggctac ccgtgatatt gctgaagagc ttggcggcga atgggctgac cgcttcctcg   4020
tgctttacgg tatcgccgct cccgattcgc agcgcatcgc cttctatcgc cttcttgacg   4080
agttcttctg aattattaac gcttacaatt tcctgatgcg gtattttctc cttacgcatc   4140
tgtgcggtat ttcacaccgc atcaggtggc acttttcggg gaaatgtgcg cggaacccct   4200
atttgtttat ttttctaaat acattcaaat atgtatccgc tcatgagaca ataaccctga   4260
taaatgcttc aataatagca cgtgctaaaa cttcattttt aatttaaaag gatctaggtg   4320
aagatccttt ttgataatct catgaccaaa atcccttaac gtgagttttc gttccactga   4380
gcgtcagacc ccgtagaaaa gatcaaagga tcttcttgag atcctttttt tctgcgcgta   4440
atctgctgct tgcaaacaaa aaaaccaccg ctaccagcgg tggtttgttt gccggatcaa   4500
gagctaccaa ctctttttcc gaaggtaact ggcttcagca gagcgcagat accaaatact   4560
gttcttctag tgtagccgta gttaggccac cacttcaaga actctgtagc accgcctaca   4620
tacctcgctc tgctaatcct gttaccagtg gctgctgcca gtggcgataa gtcgtgtctt   4680
accgggttgg actcaagacg atagttaccg gataaggcgc agcggtcggg ctgaacgggg   4740
ggttcgtgca cacagcccag cttggagcga acgacctaca ccgaactgag atacctacag   4800
cgtgagctat gagaaagcgc cacgcttccc gaagggagaa aggcggacag gtatccggta   4860
agcggcaggg tcggaacagg agagcgcacg agggagcttc caggggggaaa cgcctggtat   4920
ctttatagtc ctgtcgggtt tcgccacctc tgacttgagc gtcgattttt gtgatgctcg   4980
tcaggggggc ggagcctatg gaaaaacgcc agcaacgcgg cctttttacg gttcctggcc   5040
ttttgctggc cttttgctca catgttctt                                     5069
```

<210> SEQ ID NO 17
<211> LENGTH: 86

<212> TYPE: PRT
<213> ORGANISM: Artificial Sequence
<220> FEATURE:
<223> OTHER INFORMATION: As1-ShamirVP4 amino acid

<400> SEQUENCE: 17

```
Met Gly Ala Gly Gln Ser Ser Pro Ala Thr Gly Ser Gln Asn Gln Ser
1               5                   10                  15

Gly Asn Thr Gly Ser Ile Ile Asn Asn Tyr Tyr Met Gln Gln Tyr Gln
            20                  25                  30

Asn Ser Met Asp Thr Gln Leu Gly Asp Asn Ala Ile Ser Gly Gly Ser
        35                  40                  45

Asn Glu Gly Ser Thr Asp Thr Thr Ser Thr His Thr Asn Asn Thr Gln
    50                  55                  60

Asn Asn Asp Trp Phe Ser Arg Leu Ala Ser Ser Ala Phe Ser Gly Leu
65                  70                  75                  80

Phe Gly Ala Leu Leu Ala
                85
```

<210> SEQ ID NO 18
<211> LENGTH: 86
<212> TYPE: PRT
<213> ORGANISM: Artificial Sequence
<220> FEATURE:
<223> OTHER INFORMATION: As1- cruzeiroVP4 amino acid

<400> SEQUENCE: 18

```
Met Gly Ala Gly Gln Ser Ser Pro Ala Thr Gly Ser Gln Asn Gln Ser
1               5                   10                  15

Gly Asn Thr Gly Ser Ile Ile Asn Asn Tyr Tyr Met Gln Gln Tyr Gln
            20                  25                  30

Asn Ser Met Asp Thr Gln Leu Gly Asp Asn Ala Ile Ser Gly Gly Ser
        35                  40                  45

Asn Glu Gly Ser Thr Asp Thr Thr Ser Thr His Thr Thr Asn Thr Gln
    50                  55                  60

Asn Asn Asp Trp Phe Ser Lys Leu Ala Ser Ser Ala Phe Thr Gly Leu
65                  70                  75                  80

Phe Gly Ala Leu Leu Ala
                85
```

<210> SEQ ID NO 19
<211> LENGTH: 219
<212> TYPE: PRT
<213> ORGANISM: Artificial Sequence
<220> FEATURE:
<223> OTHER INFORMATION: FMDV-As1- shamirVP2 amino acid

<400> SEQUENCE: 19

```
Met Asp Lys Lys Thr Glu Glu Thr Thr Leu Leu Glu Asp Arg Ile Leu
1               5                   10                  15

Thr Thr Arg Asn Gly His Thr Thr Ser Thr Thr Gln Ser Ser Val Gly
            20                  25                  30

Val Thr Tyr Gly Tyr Ala Val Ala Glu Asp Ala Val Ser Gly Pro Asn
        35                  40                  45

Thr Ser Gly Leu Glu Thr Arg Val Gln Gln Ala Glu Arg Phe Phe Lys
    50                  55                  60

Lys His Leu Phe Asp Trp Thr Pro Asn Leu Ala Phe Gly His Cys Tyr
65                  70                  75                  80

Tyr Leu Glu Leu Pro Thr Glu His Lys Gly Val Tyr Gly Ser Leu Met
```

```
                85                  90                  95

Gly Ser Tyr Ala Tyr Met Arg Asn Gly Trp Asp Ile Glu Val Thr Ala
            100                 105                 110

Val Gly Asn Gln Phe Asn Gly Gly Cys Leu Leu Val Ala Leu Val Pro
        115                 120                 125

Glu Leu Lys Glu Leu Asp Thr Arg Gln Lys Tyr Gln Leu Thr Leu Phe
    130                 135                 140

Pro His Gln Phe Ile Asn Pro Arg Thr Asn Met Thr Ala His Ile Asn
145                 150                 155                 160

Val Pro Tyr Val Gly Ile Asn Arg Tyr Gly Gln Tyr Ala Leu His Lys
                165                 170                 175

Pro Trp Thr Leu Val Val Met Val Val Ala Pro Leu Thr Val Lys Thr
            180                 185                 190

Gly Gly Ser Glu Gln Ile Lys Val Tyr Met Asn Ala Ala Pro Thr Tyr
        195                 200                 205

Val His Val Ala Gly Glu Leu Pro Ser Lys Glu
    210                 215


<210> SEQ ID NO 20
<211> LENGTH: 219
<212> TYPE: PRT
<213> ORGANISM: Artificial Sequence
<220> FEATURE:
<223> OTHER INFORMATION: As1- cruzeiroVP2 amino acid

<400> SEQUENCE: 20

Met Asp Lys Lys Thr Glu Glu Thr Thr Leu Leu Glu Asp Arg Ile Leu
1               5                   10                  15

Thr Thr Arg Asn Gly His Thr Thr Ser Thr Thr Gln Ser Ser Val Gly
            20                  25                  30

Val Thr His Gly Tyr Ser Thr Glu Glu Asp His Val Ala Gly Pro Asn
        35                  40                  45

Thr Ser Gly Leu Glu Thr Arg Val Val Gln Ala Glu Arg Phe Tyr Lys
    50                  55                  60

Lys Tyr Leu Phe Asp Trp Thr Thr Asp Lys Ala Phe Gly His Leu Glu
65                  70                  75                  80

Lys Leu Glu Leu Pro Ser Asp His His Gly Val Phe Gly His Leu Val
                85                  90                  95

Asp Ser Tyr Ala Tyr Met Arg Asn Gly Trp Asp Val Glu Val Ser Ala
            100                 105                 110

Val Gly Asn Gln Phe Asn Gly Gly Cys Leu Leu Val Ala Met Val Pro
        115                 120                 125

Glu Trp Lys Glu Phe Asp Thr Arg Glu Lys Tyr Gln Leu Thr Leu Phe
    130                 135                 140

Pro His Gln Phe Ile Ser Pro Arg Thr Asn Met Thr Ala His Ile Thr
145                 150                 155                 160

Val Pro Tyr Leu Gly Val Asn Arg Tyr Asp Gln Tyr Lys Lys His Lys
                165                 170                 175

Pro Trp Thr Leu Val Val Met Val Val Ser Pro Leu Thr Val Asn Asn
            180                 185                 190

Thr Ser Ala Ala Gln Ile Lys Val Tyr Ala Asn Ile Ala Pro Thr Tyr
        195                 200                 205

Val His Val Ala Gly Glu Leu Pro Ser Lys Glu
    210                 215
```

```
<210> SEQ ID NO 21
<211> LENGTH: 17
<212> TYPE: PRT
<213> ORGANISM: Artificial Sequence
<220> FEATURE:
<223> OTHER INFORMATION: As1- shamir2A amino acid

<400> SEQUENCE: 21

Met Asn Phe Asp Leu Leu Lys Leu Ala Gly Asp Val Glu Ser Asn Pro
1               5                   10                  15

Gly


<210> SEQ ID NO 22
<211> LENGTH: 17
<212> TYPE: PRT
<213> ORGANISM: Artificial Sequence
<220> FEATURE:
<223> OTHER INFORMATION: As1- cruzeiro2A amino acid

<400> SEQUENCE: 22

Met Asn Phe Asp Leu Leu Lys Leu Ala Gly Asp Val Glu Ser Asn Pro
1               5                   10                  15

Gly


<210> SEQ ID NO 23
<211> LENGTH: 220
<212> TYPE: PRT
<213> ORGANISM: Artificial Sequence
<220> FEATURE:
<223> OTHER INFORMATION: As1- shamirVP3 amino acid

<400> SEQUENCE: 23

Met Gly Ile Val Pro Val Ala Cys Ala Asp Gly Tyr Gly Asn Met Val
1               5                   10                  15

Thr Thr Asp Pro Lys Thr Ala Asp Pro Val Tyr Gly Lys Val Phe Asn
            20                  25                  30

Pro Pro Arg Thr Asn Leu Pro Gly Arg Phe Thr Asn Phe Leu Asp Val
        35                  40                  45

Ala Glu Ala Cys Pro Thr Phe Leu Arg Phe Gly Glu Val Pro Phe Val
    50                  55                  60

Lys Thr Val Asn Ser Gly Asp Arg Leu Leu Ala Lys Phe Asp Val Ser
65                  70                  75                  80

Leu Ala Ala Gly His Met Ser Asn Thr Tyr Leu Ala Gly Leu Ala Gln
                85                  90                  95

Tyr Tyr Thr Gln Tyr Ser Gly Thr Met Asn Val His Phe Met Phe Thr
            100                 105                 110

Gly Pro Thr Asp Ala Lys Ala Arg Tyr Met Val Ala Tyr Val Pro Pro
        115                 120                 125

Gly Met Thr Pro Pro Thr Asp Pro Glu His Ala Ala His Cys Ile His
    130                 135                 140

Ser Glu Trp Asp Thr Gly Leu Asn Ser Lys Phe Thr Phe Ser Ile Pro
145                 150                 155                 160

Tyr Leu Ser Ala Ala Asp Tyr Ala Tyr Thr Ala Ser Asp Val Ala Glu
                165                 170                 175

Thr Thr Ser Val Gln Gly Trp Val Cys Ile Tyr Gln Ile Thr His Gly
            180                 185                 190

Lys Ala Glu Gly Asp Ala Leu Val Val Ser Val Ser Ala Gly Lys Asp
        195                 200                 205

Phe Glu Phe Arg Leu Pro Val Asp Ala Arg Gln Gln
```

210 215 220

<210> SEQ ID NO 24
<211> LENGTH: 222
<212> TYPE: PRT
<213> ORGANISM: Artificial Sequence
<220> FEATURE:
<223> OTHER INFORMATION: As1- cruzeiroVP3 amino acid

<400> SEQUENCE: 24

Met Gly Ile Phe Pro Val Ala Cys Ala Asp Gly Tyr Gly Gly Leu Val
1 5 10 15

Thr Thr Asp Pro Lys Thr Ala Asp Pro Ala Tyr Gly Lys Val Tyr Asn
20 25 30

Pro Pro Arg Thr Asn Tyr Pro Gly Arg Phe Thr Asn Leu Leu Asp Val
35 40 45

Ala Glu Ala Cys Pro Thr Phe Leu Cys Phe Asp Asp Gly Lys Pro Tyr
50 55 60

Val Thr Thr Arg Thr Asp Asp Thr Arg Leu Leu Ala Lys Phe Asp Leu
65 70 75 80

Ser Leu Ala Ala Lys His Met Ser Asn Thr Tyr Leu Ser Gly Ile Ala
85 90 95

Gln Tyr Tyr Thr Gln Tyr Ser Gly Thr Ile Asn Leu His Phe Met Phe
100 105 110

Thr Gly Ser Thr Asp Ser Lys Ala Arg Tyr Met Val Ala Tyr Ile Pro
115 120 125

Pro Gly Val Glu Thr Pro Pro Asp Thr Pro Glu Arg Ala Ala His Cys
130 135 140

Ile His Ala Glu Trp Asp Thr Gly Leu Asn Ser Lys Phe Thr Phe Ser
145 150 155 160

Ile Pro Tyr Val Ser Ala Ala Asp Tyr Ala Tyr Thr Ala Ser Asp Thr
165 170 175

Ala Glu Thr Ile Asn Val Gln Gly Trp Val Cys Ile Tyr Gln Ile Thr
180 185 190

His Gly Lys Ala Glu Asn Asp Thr Leu Val Val Ser Val Ser Ala Gly
195 200 205

Lys Asp Phe Glu Leu Arg Leu Pro Ile Asp Pro Arg Gln Gln
210 215 220

<210> SEQ ID NO 25
<211> LENGTH: 212
<212> TYPE: PRT
<213> ORGANISM: Artificial Sequence
<220> FEATURE:
<223> OTHER INFORMATION: As1- shamirVP1 amino acid

<400> SEQUENCE: 25

Met Thr Thr Thr Thr Gly Glu Ser Ala Asp Pro Val Thr Thr Thr Val
1 5 10 15

Glu Asn Tyr Gly Gly Glu Thr Gln Thr Ala Arg Arg Leu His Thr Asp
20 25 30

Val Ala Phe Ile Leu Asp Arg Phe Val Lys Leu Thr Ala Pro Lys Asn
35 40 45

Ile Gln Thr Leu Asp Leu Met Gln Ile Pro Ser His Thr Leu Val Gly
50 55 60

Ala Leu Leu Arg Ser Ala Thr Tyr Tyr Phe Ser Asp Leu Glu Val Ala
65 70 75 80

```
Leu Val His Thr Gly Pro Val Thr Trp Val Pro Asn Gly Ala Pro Lys
                85                  90                  95

Asp Ala Leu Asn Asn Gln Thr Asn Pro Thr Ala Tyr Gln Lys Gln Pro
            100                 105                 110

Ile Thr Arg Leu Ala Leu Pro Tyr Thr Ala Pro His Arg Val Leu Ala
        115                 120                 125

Thr Val Tyr Asn Gly Lys Thr Ala Tyr Gly Glu Thr Thr Ser Arg Arg
    130                 135                 140

Gly Asp Met Ala Ala Leu Ala Gln Arg Leu Ser Ala Arg Leu Pro Thr
145                 150                 155                 160

Ser Phe Asn Tyr Gly Ala Val Lys Ala Asp Thr Ile Thr Glu Leu Leu
                165                 170                 175

Ile Arg Met Lys Arg Ala Glu Thr Tyr Cys Pro Arg Pro Leu Leu Ala
            180                 185                 190

Leu Asp Thr Thr Gln Asp Arg Arg Lys Gln Glu Ile Ile Ala Pro Glu
        195                 200                 205

Lys Gln Val Leu
    210


<210> SEQ ID NO 26
<211> LENGTH: 214
<212> TYPE: PRT
<213> ORGANISM: Artificial Sequence
<220> FEATURE:
<223> OTHER INFORMATION: As1- cruzeiroVP1 amino acid

<400> SEQUENCE: 26

Met Thr Thr Ala Thr Gly Glu Ser Ala Asp Pro Val Thr Thr Thr Val
1               5                   10                  15

Glu Asn Tyr Gly Gly Glu Thr Gln Ile Gln Arg Arg His His Thr Asp
            20                  25                  30

Ile Gly Phe Ile Met Asp Arg Phe Val Lys Ile Gln Ser Leu Ser Pro
        35                  40                  45

Thr His Val Ile Asp Leu Met Gln Thr His Gln His Gly Leu Val Gly
    50                  55                  60

Ala Leu Leu Arg Ala Ala Thr Tyr Tyr Phe Ser Asp Leu Glu Ile Val
65                  70                  75                  80

Val Arg His Glu Gly Asn Leu Thr Trp Val Pro Asn Gly Ala Pro Glu
                85                  90                  95

Ser Ala Leu Leu Asn Thr Ser Asn Pro Thr Ala Tyr Asn Lys Ala Pro
            100                 105                 110

Phe Thr Arg Leu Ala Leu Pro Tyr Thr Ala Pro His Arg Val Leu Ala
        115                 120                 125

Thr Val Tyr Asn Gly Thr Ser Lys Tyr Ala Val Gly Gly Ser Gly Arg
    130                 135                 140

Arg Gly Asp Met Gly Ser Leu Ala Ala Arg Val Val Lys Gln Leu Pro
145                 150                 155                 160

Ala Ser Phe Asn Tyr Gly Ala Ile Lys Ala Asp Ala Ile His Glu Leu
                165                 170                 175

Leu Val Arg Met Lys Arg Ala Glu Leu Tyr Cys Pro Arg Pro Leu Leu
            180                 185                 190

Ala Ile Glu Val Ser Ser Gln Asp Arg His Lys Gln Lys Ile Ile Ala
        195                 200                 205

Pro Ala Lys Gln Leu Leu
    210
```

<210> SEQ ID NO 27
<211> LENGTH: 7
<212> TYPE: PRT
<213> ORGANISM: Artificial Sequence
<220> FEATURE:
<223> OTHER INFORMATION: proteolytic cleavage site

<400> SEQUENCE: 27

Arg Gly Arg Lys Arg Arg Ser
1 5

<210> SEQ ID NO 28
<211> LENGTH: 756
<212> TYPE: DNA
<213> ORGANISM: Artificial Sequence
<220> FEATURE:
<223> OTHER INFORMATION: consensus Protease C3 nucleic acid

<400> SEQUENCE: 28
tactgcgtga agaagcccgt ggccctgaag gtgaaggcca agaacaccct gatcgtgacc 60
gagagcggcg cccccccac cgacctgcag aagatggtga tgggcaacac caagcccgtg 120
gagctgatcc tggacggcaa gaccgtggcc atctgctgcg ccaccggcgt gttcggcacc 180
gcctacctgg tgccccgcca cctgttcgcc gagaagtacg acaagatcat gctggacggc 240
cgcgccatga ccgacagcga ctaccgcgtg ttcgagttcg agatcaaggt gaagggccag 300
gacatgctga gcgacgccgc cctgatggtg ctgcaccgcg gcaaccgcgt gcgcgacatc 360
accaagcact tccgcgacac cgcccgcatg aagaagggca cccccgtggt gggcgtgatc 420
aacaacgccg acgtgggccg cctgatcttc agcggcgagg ccctgaccta caaggacatc 480
gtggtgtgca tggacggcga caccatgccc ggcctgttcg cctacaaggc cgccaccaag 540
gccggctact gcggcggcgc cgtgctggcc aaggacggcg ccgacacctt catcgtgggc 600
acccacagcg ccggcggccg caacggcgtg ggctactgca gctgcgtgag ccgcagcatg 660
ctgctgaaga tgaaggccca catcgacccc gagccccacc acgagggcct gatcgtggac 720
acccgcgacg tggaggagcg cgtgcacgtg atgtga 756

<210> SEQ ID NO 29
<211> LENGTH: 251
<212> TYPE: PRT
<213> ORGANISM: Artificial Sequence
<220> FEATURE:
<223> OTHER INFORMATION: Amino Acid sequence of Consensus Protease C3

<400> SEQUENCE: 29

Tyr Cys Val Lys Lys Pro Val Ala Leu Lys Val Lys Ala Lys Asn Thr
1 5 10 15

Leu Ile Val Thr Glu Ser Gly Ala Pro Pro Thr Asp Leu Gln Lys Met
20 25 30

Val Met Gly Asn Thr Lys Pro Val Glu Leu Ile Leu Asp Gly Lys Thr
35 40 45

Val Ala Ile Cys Cys Ala Thr Gly Val Phe Gly Thr Ala Tyr Leu Val
50 55 60

Pro Arg His Leu Phe Ala Glu Lys Tyr Asp Lys Ile Met Leu Asp Gly
65 70 75 80

Arg Ala Met Thr Asp Ser Asp Tyr Arg Val Phe Glu Phe Glu Ile Lys
85 90 95

Val Lys Gly Gln Asp Met Leu Ser Asp Ala Ala Leu Met Val Leu His
100 105 110

-continued

```
Arg Gly Asn Arg Val Arg Asp Ile Thr Lys His Phe Arg Asp Thr Ala
        115                 120                 125

Arg Met Lys Lys Gly Thr Pro Val Val Gly Val Ile Asn Asn Ala Asp
    130                 135                 140

Val Gly Arg Leu Ile Phe Ser Gly Glu Ala Leu Thr Tyr Lys Asp Ile
145                 150                 155                 160

Val Val Cys Met Asp Gly Asp Thr Met Pro Gly Leu Phe Ala Tyr Lys
                165                 170                 175

Ala Ala Thr Lys Ala Gly Tyr Cys Gly Gly Ala Val Leu Ala Lys Asp
            180                 185                 190

Gly Ala Asp Thr Phe Ile Val Gly Thr His Ser Ala Gly Gly Arg Asn
        195                 200                 205

Gly Val Gly Tyr Cys Ser Cys Val Ser Arg Ser Met Leu Leu Lys Met
    210                 215                 220

Lys Ala His Ile Asp Pro Glu Pro His His Glu Gly Leu Ile Val Asp
225                 230                 235                 240

Thr Arg Asp Val Glu Glu Arg Val His Val Met
                245                 250
```